(12) United States Patent
Takahashi et al.

(10) Patent No.: US 8,691,120 B2
(45) Date of Patent: Apr. 8, 2014

(54) CHROMENE COMPOUND

(75) Inventors: Toshiaki Takahashi, Shunan (JP); Junji Takenaka, Shunan (JP); Junji Momoda, Shunan (JP); Mitsuyoshi Sando, Shunan (JP); Kazuhiro Teranishi, Shunan (JP)

(73) Assignee: Tokuyama Corporation, Shunan-Shi (JP)

( * ) Notice: Subject to any disclaimer, the term of this patent is extended or adjusted under 35 U.S.C. 154(b) by 12 days.

(21) Appl. No.: 13/496,689

(22) PCT Filed: Sep. 15, 2010

(86) PCT No.: PCT/JP2010/066467
§ 371 (c)(1),
(2), (4) Date: Mar. 16, 2012

(87) PCT Pub. No.: WO2011/034202
PCT Pub. Date: Mar. 24, 2011

(65) Prior Publication Data
US 2012/0170098 A1    Jul. 5, 2012

(30) Foreign Application Priority Data
Sep. 18, 2009   (JP) .................. 2009-217583

(51) Int. Cl.
- G02B 5/23 (2006.01)
- F21V 9/00 (2006.01)
- G02B 5/02 (2006.01)
- G02C 7/10 (2006.01)
- G02F 1/361 (2006.01)
- G03B 11/00 (2006.01)
- G02F 1/03 (2006.01)
- G02F 1/07 (2006.01)

(52) U.S. Cl.
USPC ............ 252/586; 252/582; 359/241; 544/79; 544/129; 544/141; 544/143; 544/150; 544/154; 546/15; 548/407; 549/330; 549/382; 549/406; 549/502; 564/114; 564/426; 568/325; 568/633

(58) Field of Classification Search
USPC ............ 252/586, 582; 359/241; 544/79, 129, 544/141, 143, 150, 154; 546/15; 548/407; 549/330, 382, 502, 406; 564/114, 426; 568/633, 325
See application file for complete search history.

(56) References Cited

U.S. PATENT DOCUMENTS

| | | | |
|---|---|---|---|
| 6,146,554 A | 11/2000 | Melzig et al. | |
| 6,296,785 B1 | 10/2001 | Nelson et al. | |
| 6,723,859 B2 | 4/2004 | Kawabata et al. | |
| 6,774,202 B2 | 8/2004 | Lee | |
| 7,008,568 B2 | 3/2006 | Qin | |
| 7,521,004 B2 | 4/2009 | Momoda et al. | |
| 7,556,750 B2 | 7/2009 | Xiao et al. | |
| 8,147,726 B2 | 4/2012 | Kasai et al. | |
| 2003/0096117 A1 | 5/2003 | Kawabata et al. | |
| 2005/0263745 A1 | 12/2005 | Momoda et al. | |
| 2007/0215844 A1* | 9/2007 | Momoda et al. | 252/582 |
| 2007/0278461 A1 | 12/2007 | Petrovskaia et al. | |

FOREIGN PATENT DOCUMENTS

| | | |
|---|---|---|
| EP | 1184379 A1 | 3/2002 |
| EP | 1674460 A1 | 6/2006 |
| JP | 2005-112772 A | 4/2005 |
| JP | 2005-187420 A | 7/2005 |
| WO | WO 99/15518 A1 | 4/1999 |
| WO | WO 01/05854 A1 | 1/2001 |
| WO | WO 01/19813 A1 | 3/2001 |
| WO | WO 01/60811 A1 | 8/2001 |
| WO | WO 01/60881 A2 | 8/2001 |
| WO | WO 03/044022 A3 | 5/2003 |
| WO | WO 2005/028465 A1 | 3/2005 |
| WO | WO 2006/110219 A1 | 10/2006 |
| WO | WO 2007/140071 A1 | 12/2007 |
| WO | WO 2009/136668 A1 | 11/2009 |

OTHER PUBLICATIONS

Extended European Search Report for European Application No. 10817314.7 dated Feb. 4, 2013.
International Preliminary Report on Patentability and Written Opinion of the International Searching Authority for International Application No. PCT/JP2010/066467 dated Apr. 19, 2012.
International Search Report issued in PCT/JP2010/066467, dated Oct. 26, 2010.

* cited by examiner

*Primary Examiner* — Bijan Ahvazi
(74) *Attorney, Agent, or Firm* — Birch, Stewart, Kolasch & Birch, LLP

(57) ABSTRACT

A photochromic chromene compound having an indeno(2,1-f)naphtho(1,2-b)pyran structure as its basic skeleton, an aryl group or a heteroaryl group at the 6-position carbon atom of the structure and an electron donor group having a Hammett constant $\sigma_p$ of not more than −0.1 at the 7-position carbon atom.

16 Claims, No Drawings

CHROMENE COMPOUND

TECHNICAL FIELD

The present invention relates to a photochromic chromene compound, and use and an intermediate thereof. More specifically, it relates to a chromene compound which is useful as a photochromic compound for photochromic spectacle lenses, and use and an intermediate thereof.

BACKGROUND ART

Photochromism is the reversible function of a certain compound that it changes its color swiftly upon exposure to light including ultraviolet light such as sunlight or light from a mercury lamp and returns to its original color when it is put in the dark by stopping its exposure to light. A compound having this property is called "photochromic compound" and used as a material for photochromic plastic lenses.

For the photochromic compound used for this purpose, the following properties are required: (I) the degree of coloration at a visible light range before ultraviolet light is applied (to be referred to as "initial coloration" hereinafter) should be low, (II) the degree of coloration upon exposure to ultraviolet light (to be referred to as "color optical density" hereinafter) should be high, (III) the speed from the time when the application of ultraviolet light is started to the time when the color optical density reaches saturation (to be referred to as "color development sensitivity" hereinafter) should be high; (IV) the speed from the stoppage of the application of ultraviolet light to the time when the compound returns to its original state (to be referred to as "fading speed" hereinafter) should be high, (V) the repeat durability of this reversible function should be high, and (VI) the solubility in a monomer composition which will become a host material after curing of the photochromic compound should be high so that its dispersibility in the host material in use becomes high.

As the photochromic compound which can satisfy these requirements, there are known chromene compounds having an indeno(2,1-f)naphtho(1,2-b)pyran structure as the basic skeleton (refer to a pamphlet of International Laid-Open WO99/15518 and a pamphlet of International Laid-Open WO01/60811).

It is preferred that a photochromic plastic lens comprising the photochromic compound should develop a color of a neutral tint such as gray or brown. A color of a neutral tint is obtained by mixing together several different kinds of photochromic compounds which develop different colors, for example, a yellow to red photochromic compound (yellow compound) having a maximum absorption at 430 to 530 nm and a purple to blue photochromic compound (blue compound) having a maximum absorption at 550 to 650 nm.

However, when color control is carried out by this method, various problems occur due to the difference in photochromic properties between the compounds which have been mixed together. For example, when the repeat durability of the yellow compound is lower than that of the blue compound and the photochromic plastic lens is used for a long time, there occurs a problem that the developed color gradually changes to a color of a strong blue tint.

Further, when the color development sensitivity and fading speed of the yellow compound are lower than those of the blue compound, there arises a problem that color during development has a strong blue tint and color during fading has a strong yellow tint.

It is considered that this problem can be solved by using a single compound which has two or more absorption maximums at the time of exposure and develops a color of a neutral tint (double peak compound). It is known that the yellow compound is generally inferior to the blue compound in durability. Therefore, a compound having a higher yellow color optical density (having a maximum absorption wavelength at 430 to 530 nm) than the blue color optical density (having a maximum absorption wavelength at 550 to 650 nm) is desired as the double peak compound (the ratio of the yellow color optical density to the blue color optical density in the double peak compound may be referred to as "double peak characteristic" hereinafter).

As the photochromic compound having two absorption maximums at the time of color development (double peak compound), there have been known compounds having an indeno(2,1-f)naphtho(1,2-b)pyran structure as the basic skeleton and represented by the following formulas (A) to (C).

However, these compounds have room for the improvement of the following points. That is, a chromene compound represented by the following formula (A) (refer to a pamphlet of International Laid-Open WO01/19813) has low color development sensitivity, low fading speed and low repeat durability though its double peak characteristic is high.

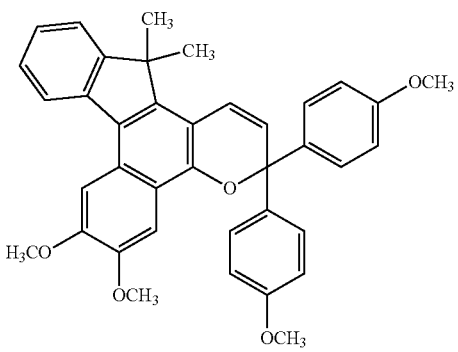

(A)

A chromene compound represented by the following formula (B) (refer to a pamphlet of International Laid-Open WO03/044022) has low double peak characteristic with a smaller absorption at 430 to 530 nm than an absorption at 550 to 650 nm.

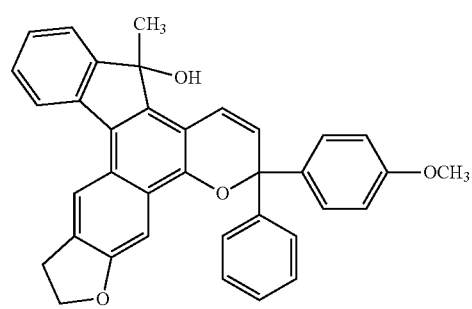

(B)

A chromene compound represented by the following formula (C) (refer to a pamphlet of International Laid-Open WO05/028465) has large initial coloration as the end of its absorption spectrum (to be referred to as "absorption end" hereinafter) goes beyond 420 nm into the visible range though it has excellent double peak characteristic and practical levels of color optical density and fading speed.

(C)

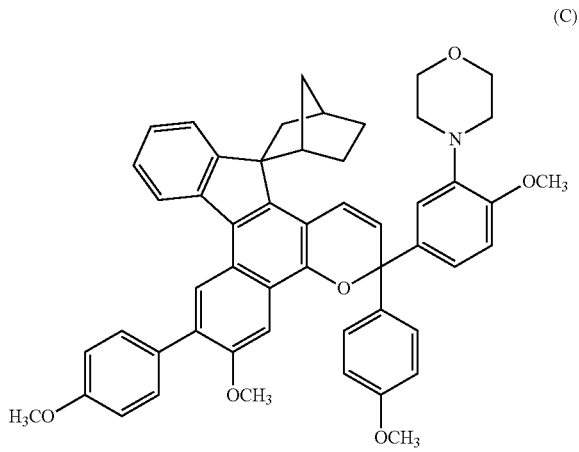 [SMILES: COc1ccc(-c2cc3c4c(c5c(c3cc2OC)OC(c2ccc(OC)cc2)(c2ccc(OC)c(N3CCOCC3)c2)C=C5)C2(CC3CCC2C3)c2ccccc2-4)cc1]

DISCLOSURE OF THE INVENTION

It is therefore an object of the present invention to provide a chromene compound which develops a color of a neutral tint, has little initial coloration, high color optical density, high color development sensitivity, high fading speed and excellent durability of photochromic properties and can be dissolved in a monomer composition which will become the substrate of an optical article in a high concentration.

It is another object of the present invention to provide a novel naphthol compound for the manufacture of the chromene compound of the present invention.

Other objects and advantages of the present invention will become apparent from the following description.

It is known that a compound having a substituent having high electron donating ability bonded to the 6-position and 7-position of an indeno(2,1-f)naphtho(1,2-b)pyran structure exhibits high double peak characteristic. The substituent having high electron donating ability as used herein is a substituent bonded to the 6-position and the 7-position via an oxygen atom or a nitrogen atom. However, although the above compound has high double peak characteristic, it has defects such as low fading speed, large color development by heat at room temperature under no exposure (this color development will be referred to as "initial coloration by thermochromism" hereinafter) and low durability. Particularly when the electron donating abilities of the 6-position and 7-position substituents are further increased, the above defects become more marked.

Then, the inventors of the present invention have conducted intensive studies to solve the above problems and have found that a chromene compound which has an aryl group or heteroaryl group introduced into the 6-position and an electron donor substituent having a Hammett constant $\sigma_p$ of not more than –0.1 introduced into the 7-position has excellent characteristic properties such as fading speed, initial coloration by thermochromism and durability while retaining high double peak characteristic. Even when the electron donating ability of the 7-position substituent is increased, the obtained chromene compound is characterized in that the reductions of fading speed, initial coloration by thermochromism and durability are extremely small. Further, the absorption end of the above compound is existent at an appropriate range (not too short wavelength range and not a visible range), the color development sensitivity is high and the initial coloration due to the absorption end is little. Therefore, they could find a photochromic compound which satisfies all the requirements for a photochromic plastic lens material and accomplished the present invention. The Hammett constant $\sigma_p$ is defined based on the Hammett equation that quantifies the electric effect of a substituent bonded to an π electron system on the basis of the dissociation constant Ka of p-substituted benzoic acid. A substituent having a $\sigma_p$ of 0 is a hydrogen atom, and a substituent having a $\sigma_p$ of less than 0 is a substituent having higher electron donating ability than a hydrogen atom.

Although the reason for obtaining such an unexpected effect is unknown, it is presumed that this is due to a resonance effect between the 6-position aryl group or heteroaryl group and the indeno(2,1-f)naphtho(1,2-b)pyran skeleton.

Firstly, the present invention is a chromene compound having a skeleton represented by the following formula (1).

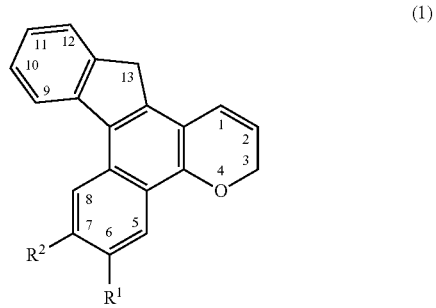

(1)

In the above formula, $R^1$ is an aryl group or a heteroaryl group. $R^2$ is an electron donor group having a Hammett constant $\sigma_p$ of not more than –0.1.

Secondly, the present invention is a photochromic curable composition comprising the above chromene compound of the present invention and polymerizable monomers.

Thirdly, the present invention is a photochromic optical article having a polymer molded product containing the chromene compound of the present invention dispersed therein as a constituent member.

In the fourth place, the present invention is an optical article having an optical substrate all or part of at least one surface of which is coated with a polymer film containing the chromene compound of the present invention dispersed therein as a constituent member.

In the fifth place, the present invention is a naphthol compound which is a raw material compound for the production of the chromene compound of the present invention.

BEST MODE FOR CARRYING OUT THE INVENTION

The chromene compound of the present invention has an indeno(2,1-f)naphtho(1,2-b)pyran structure represented by the above formula (1) as the basic skeleton. The chromene compound of the present invention has an aryl group or a heteroaryl group at the 6-position of the basic skeleton and an electron donor group having a Hammett constant $\sigma_p$ of not more than –0.1 at the 7-position, thereby making it possible to develop a dark color of a neutral tint by itself while retaining excellent photochromic properties. A description is first given of $R^1$ and $R^2$ in the formula (1).

<$R^1$>

$R^1$ which is a substituent bonded to the 6-position of the indeno(2,1-f)naphtho(1,2-b)pyran structure is an aryl group or a heteroaryl group.

The aryl group is preferably an aryl group having 6 to 14 carbon atoms. Preferred examples of the aryl group include phenyl group, 1-naphthyl group, 2-naphthyl group, 1-phenanthryl group, 2-phenanthryl group, 1-anthryl group and 9-anthryl group.

The heteroaryl group is preferably a heteroaryl group having 4 to 12 carbon atoms. The heteroaryl group is a group which forms a carbon-carbon bond together with the 6-position carbon atom. Preferred examples of the heteroaryl group include thienyl group, furyl group, pyrrolinyl group, pyridyl group, benzothienyl group, benzofuryl group and benzopyrrolinyl group.

The hydrogen atoms, preferably 1 to 4 hydrogen atoms of the above aryl group or the above heteroaryl group may be substituted by a hydroxyl group, alkyl group, haloalkyl group, cycloalkyl group, alkoxy group, amino group, heterocyclic group having a ring member nitrogen atom and bonded to an aryl group or a heteroaryl group bonded thereto via the nitrogen atom, cyano group, nitro group, formyl group, hydroxycarbonyl group, alkylcarbonyl group, alkoxycarbonyl group, halogen atom, aralkyl group, aralkoxy group, aryl group or aryloxy group. A description is subsequently given of these substituents.

<Substituent of $R^1$>

The alkyl group is preferably an alkyl group having 1 to 6 carbon atoms. Preferred examples of the alkyl group include methyl group, ethyl group, n-propyl group, isopropyl group, n-butyl group, sec-butyl group, tert-butyl group, pentyl group and hexyl group.

The haloalkyl group is preferably an alkyl group having 1 to 6 carbon atoms and substituted by a fluorine atom, chlorine atom or bromine atom. Preferred examples of the haloalkyl group include trifluoromethyl group, pentafluoroethyl group, chloromethyl group, 2-chloroethyl group and bromomethyl group.

The cycloalkyl group is preferably a cycloalkyl group having 3 to 8 carbon atoms. Preferred examples of the cycloalkyl group include cyclopropyl group, cyclobutyl group, cyclopentyl group and cyclohexyl group.

The alkoxy group is preferably an alkoxy group having 1 to 6 carbon atoms. Preferred examples of the alkoxy group include methoxy group, ethoxy group, n-propoxy group, isopropoxy group, n-butoxy group, sec-butoxy group and tert-butoxy group.

The amino group is not limited to amino group (—NH$_2$), and one or two hydrogen atoms thereof may be substituted. Examples of the substituent of the amino group include alkyl group having 1 to 6 carbon atoms, alkoxy group having 1 to 6 carbon atoms, cycloalkyl group having 3 to 8 carbon atoms, aryl group having 6 to 10 carbon atoms and heteroaryl group having 4 to 12 carbon atoms. Examples of these substituents are the same as those enumerated for $R^1$ and its substituent. Preferred examples of the amino group include amino group, methylamino group, dimethylamino group, ethylamino group, diethylamino group, phenylamino group and diphenylamino group.

Preferred examples of the heterocyclic group having a ring member nitrogen atom and bonded to an aryl group or a heteroaryl group bonded thereto via the nitrogen atom include morpholino group, piperidino group, pyrrolidinyl group, piperazino group, N-methylpiperazino group and indolinyl group. Further, the heterocyclic group may have a substituent having a Hammett constant $\sigma_p$ of less than 0. Examples of the substituent include alkyl groups such as methyl group. Preferred examples of the heterocyclic group having a substituent include 2,6-dimethylmorpholino group, 2,6-dimethylpiperidino group and 2,2,6,6-tetramethylpiperidino group.

The alkylcarbonyl group is preferably an alkylcarbonyl group having 2 to 7 carbon atoms. Preferred examples thereof include acetyl group and ethylcarbonyl group.

The alkoxycarbonyl group is preferably an alkoxycarbonyl group having 2 to 7 carbon atoms. Preferred examples thereof include methoxycarbonyl group and ethoxycarbonyl group.

Examples of the halogen atom are fluorine atom, chlorine atom, bromine atom and iodine atom.

The aralkyl group is preferably an aralkyl group having 7 to 11 carbon atoms. Preferred examples of the aralkyl group include benzyl group, phenylethyl group, phenylpropyl group, phenylbutyl group and naphthylmethyl group.

The aralkoxy group is preferably an aralkoxy group having 7 to 11 carbon atoms. Preferred examples of the aralkoxy group include benzyloxy group and naphthylmethoxy group.

The aryl group is preferably an aryl group having 6 to 10 carbon atoms. Preferred examples of the aryl group include phenyl group, 1-naphthyl group and 2-naphthyl group.

The aryloxy group is preferably an aryloxy group having 6 to 10 carbon atoms. Preferred examples of the aryloxy group include phenoxy group, 1-naphthoxy group and 2-naphthoxy group.

<Preferred $R^1$>

Out of the groups $R^1$, an aryl group having 6 to 14 carbon atoms is preferred because it provides a compound having excellent double peak characteristic. To obtain especially excellent double peak characteristic and high color optical density, 1 to 4 hydrogen atoms of the aryl group are substituted preferably by a substituent having a Hammett constant $\sigma_p$ of −1.00 or more to less than 0, particularly preferably by a substituent having a Hammett constant $\sigma_p$ of −1.00 or more to less than −0.2. Stated more specifically, an aryl group substituted by at least one group selected from the group consisting of hydroxyl group, alkoxy group, amino group, heterocyclic group having a ring member nitrogen atom and bonded to an aryl group bonded thereto via the nitrogen atom, aralkoxy group and aryloxy group is such an example. An aryl group substituted by at least one group selected from the group consisting of hydroxyl group, alkoxy group, amino group, heterocyclic group having a ring member nitrogen atom and bonded to an aryl group bonded thereto via the nitrogen atom and aryloxy group is more preferred, and an aryl group substituted by at least one group selected from the group consisting of alkoxy group, amino group and heterocyclic group having a ring member nitrogen atom and bonded to an aryl group bonded thereto via the nitrogen atom is particularly preferred. Particularly preferred examples of the aryl group include 4-methoxyphenyl group, 2,4-dimethoxyphenyl group, 4-(N,N-dimethylamino)phenyl group and 4-morphpolinophenyl group.

<$R^2$>

In the present invention, $R^2$ is an electron donor group having a Hammett constant $\sigma_p$ of not more than −0.1.

Examples of $R^2$ which is an electron donor group having a $\sigma_p$ of not more than −0.1 include hydroxyl group ($\sigma_p$=−0.37), alkyl group, cycloalkyl group, alkoxy group, aryloxy group, aralkyl group, aralkoxy group, amino group and heterocyclic group having a ring member nitrogen atom and bonded to the 7-position carbon atom of a benzene ring bonded thereto via the nitrogen atom.

A detailed description is given of the above electron donor group having a $\sigma_p$ of not more than −0.1.

The alkyl group is generally a group having a Hammett constant $\sigma_p$ of −0.2 to −0.1. In the present invention, an alkyl group having 1 to 6 carbon atoms is particularly preferred. 1 to 13 hydrogen atoms, particularly preferably 1 to 4 hydrogen atoms of the alkyl group may be substituted by the above hydroxyl group, alkoxy group, amino group or heterocyclic group having a ring member nitrogen atom and bonded to an alkyl group bonded thereto via the nitrogen atom described for the substituent of $R^1$. The above heterocyclic group substituting the alkyl group is identical to the heterocyclic group substituting the aryl group or the heteroaryl group described in <substituent of $R^1$>. The substituent having a ring member nitrogen atom and bonded via the nitrogen atom is synonymous hereinbelow. Preferred examples of the alkyl group include methyl group ($\sigma_p=-0.10$), ethyl group ($\sigma_p=-0.20$), n-propyl group ($\sigma_p=-0.12$), isopropyl group, n-butyl group, sec-butyl group, tert-butyl group ($\sigma_p=-0.15$), pentyl group and hexyl group. Preferred examples of the substituted alkyl group include hydroxymethyl group, methoxymethyl group, N,N-dimethylaminomethyl group and morpholinomethyl group.

The above cycloalkyl group is generally a group having a $\sigma_p$ of −0.2 to −0.1. In the present invention, a cycloalkyl group having 3 to 20 carbon atoms is particularly preferred. Further, 1 to 39 hydrogen atoms, particularly preferably 1 to 20 hydrogen atoms of the cycloalkyl group may be substituted by the above hydroxyl group, alkoxy group, amino group, heterocyclic group having a ring member nitrogen atom and bonded to a cycloalkyl group bonded thereto via the nitrogen atom or halogen atom described for the substituent of $R^1$. Preferred examples of the cycloalkyl group include cyclopropyl group, cyclobutyl group, cyclopentyl group and cyclohexyl group ($\sigma_p=-0.16$). Preferred examples of the substituted cycloalkyl group include 4-hydroxycyclohexyl group, 4-methoxycyclohexyl group and 4-morpholinocyclohexyl group.

The above alkoxy group is generally a group having a $\sigma_p$ of −0.3 to −0.2. In the present invention, an alkoxy group having 1 to 15 carbon atoms is particularly preferred. Further, 1 to 31 hydrogen atoms, particularly preferably 1 to 10 hydrogen atoms of the alkoxy group may be substituted by the above hydroxyl group, alkoxy group, amino group, heterocyclic group having a ring member nitrogen atom and bonded to an alkoxy group bonded thereto via the nitrogen atom or halogen atom described for the substituent of $R^1$. Preferred examples of the alkoxy group include methoxy group ($\sigma_p=-0.28$), ethoxy group ($\sigma_p=-0.21$), n-propoxy group ($\sigma_p=-0.26$), isopropoxy group, n-butoxy group, sec-butoxy group, tert-butoxy group, cyclopropyloxy group, cyclobutyloxy group, cyclopentyloxy group, cyclohexyloxy group, norbornyloxy group, 1-adamantyloxy group and 2-adamantyloxy group. Examples of the substituted alkoxy group include methoxymethoxy group, N,N-dimethylaminomethoxy group and morpholinomethoxy group.

The above amino group is generally a group having a $\sigma_p$ of −1.0 to −0.5. The preferred amino group may be either an amino group (—NH$_2$) ($\sigma_p=-0.66$) or a substituted amino group. The substituent of the amino group is selected from alkyl group having 1 to 6 carbon atoms, haloalkyl group having 1 to 6 carbon atoms, alkoxy group having 1 to 15 carbon atoms, cycloalkyl group having 3 to 15 carbon atoms, halogen atom, aryl group having 6 to 10 carbon atoms and heteroaryl group having 4 to 12 carbon atoms. Examples of the haloalkyl group, aryl group and heteroaryl group are the same as those enumerated for the substituent of $R^1$. Examples of the other groups are the same as those enumerated for the substituent of $R^2$. Preferred examples of the amino group having one or two substituents include monoalkylamino groups such as methylamino group ($\sigma_p=-0.77$) and ethylamino group; dialkylamino groups such as dimethylamino group ($\sigma_p=-0.83$) and diethylamio group; monoarylamino groups such as phenylamino group ($\sigma_p=-0.11$); diarylamino groups such as diphenylamino group; halogenoamino groups such as difluoroamino group; and haloalkylamino groups such as bis(trifluoromethyl)amino group.

The heterocyclic group having a ring member nitrogen atom and bonded to the 7-position carbon atom via the nitrogen atom is generally a group having a $\sigma_p$ of −1.0 to −0.4. Preferred examples of the heterocyclic group include morpholino group ($\sigma_p=-0.50$), piperidino group ($\sigma_p=-0.83$), pyrrolidinyl group, piperazino group, N-methylpiperazino group and indolinyl group. Further, the heterocyclic group may have an alkyl group having 1 to 6 carbon atoms, haloalkyl group having 1 to 6 carbon atoms, alkoxy group having 1 to 15 carbon atoms, cycloalkyl group having 3 to 15 carbon atoms, halogen atom, aryl group having 6 to 10 carbon atoms or heteroaryl group having 4 to 12 carbon atoms as a substituent. Examples of the haloalkyl group, aryl group and heteroaryl group are the same as those enumerated for the substituent of $R^1$. Examples of the other groups are the same as those enumerated for the substituent of $R^2$. Examples of the substituent include alkyl groups such as methyl group. Examples of the heterocyclic group having a substituent include 2,6-dimethylmorpholino group, 2,6-dimethylpiperidino group, 2,2,6,6-tetramethylpiperidino group, 2-fluoromorpholino group and 2,6-difluoromorpholino group.

The aryloxy group is generally a group having a $\sigma_p$ of −0.5 to −0.2. In the present invention, an aryloxy group having 6 to 10 carbon atoms is particularly preferred. Preferred examples of the aryloxy group include phenoxy group ($\sigma_p=-0.32$) and 1-naphthoxy group.

The aralkyl group is generally a group having a $\sigma_p$ of not more than −0.1. In the present invention, an aralkyl group having 7 to 11 carbon atoms is particularly preferred. Preferred examples of the aralkyl group include benzyl group, phenylethyl group, phenylpropyl group, phenylbutyl group and naphthylmethyl group.

The aralkoxy group generally is generally a group having a $\sigma_p$ of not more than −0.1. In the present invention, an aralkoxy group having 7 to 11 carbon atoms is particularly preferred. Preferred examples of the aralkoxy group include benzyloxy group and naphthylmethoxy group.

One or more hydrogen atoms on the benzene ring of each of the aryloxy group, aralkyl group and aralkoxy group may be substituted by an alkyl group having 1 to 6 carbon atoms, cycloalkyl group having 3 to 15 carbon atoms, alkoxy group having 1 to 15 carbon atoms, amino group or heterocyclic group having a ring member nitrogen atom and bonded to a benzene ring bonded thereto via the nitrogen atom. Examples of these substituents are the same as those enumerated for $R^2$. The aryloxy group, aralkyl group and aralkoxy group substituted by these substituents have a $\sigma_p$ of not more than −0.1 as well.

<Preferred $R^2$>

The group $R^2$ is preferably a substituent having a $\sigma_p$ of not more than −0.2 because a combination of it and the above $R^1$ provides a compound having excellent double peak characteristic and high color optical density. $R^2$ is preferably selected from hydroxyl group, alkoxy group, aryloxy group, amino group and heterocyclic group having a ring member nitrogen atom and bonded to the 7-position carbon atom via the nitrogen atom. Preferred examples of $R^2$ include hydroxyl group, methoxy group, phenoxy group, morpholino group, piperidino group and dimethylamino group. $R^2$ is preferably a substituent having a $\sigma_p$ of −0.6 to −0.2 because it reduces initial coloration by thermochromism and increases the fading speed. The substituent is more preferably an alkoxy group, aryloxy group, amino group or heterocyclic group having a ring member nitrogen atom and bonded to the 7-position carbon atom via the nitrogen atom, all of which have a $\sigma_p$ of –0.6 to –0.2. The substituent is particularly preferably a methoxy group, phenoxy group, difluoroamino group or morpholino group.

<Preferred Chromene Compound>

Out of the chromene compounds of the present invention, a chromene compound represented by the following formula (2) is preferred as it develops a color of a neutral tint and has little initial coloration, high color optical density, high fading speed and high durability.

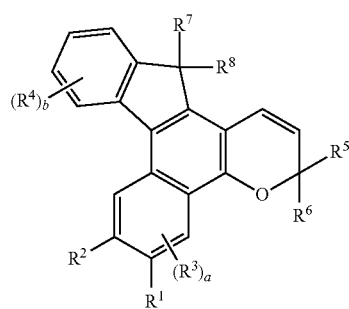

(2)

The substituents $R^1$ to $R^8$ of the chromene compound represented by the above formula (2) will be described hereinbelow.

<$R^1$>

In the above formula (2), $R^1$ is an aryl group or a heteroaryl group. Examples of these groups are the same as those enumerated above. Preferred examples thereof are the same as above.

<$R^2$>

In the above formula (2), $R^2$ is an electron donor group having a $\sigma_p$ of not more than –0.1. Examples of $R^2$ are the same as those enumerated above. Preferred examples thereof are the same as above.

<$R^3$ and $R^4$>

$R^3$ and $R^4$ are each independently a hydroxyl group, alkyl group, haloalkyl group, cycloalkyl group, alkoxy group, amino group, heterocyclic group having a ring member nitrogen atom and bonded to a benzene ring bonded thereto via the nitrogen atom, cyano group, nitro group, formyl group, hydroxycarbonyl group, alkylcarbonyl group, alkoxycarbonyl group, halogen atom, aralkyl group, aralkoxy group, aryl group or aryloxy group.

Out of these, $R^3$ and $R^4$ are each preferably an alkyl group having 1 to 6 carbon atoms, haloalkyl group having 1 to 6 carbon atoms, cycloalkyl group having 3 to 15 carbon atoms, alkoxy group having 1 to 15 carbon atoms, amino group, heterocyclic group having a ring member nitrogen atom and bonded to a benzene ring bonded thereto via the nitrogen atom, alkylcarbonyl group having 2 to 7 carbon atoms, alkoxycarbonyl group having 2 to 7 carbon atoms, halogen atom, aralkyl group having 7 to 11 carbon atoms, aralkoxy group having 7 to 11 carbon atoms, aryl group having 6 to 10 carbon atoms or aryloxy group having 6 to 10 carbon atoms. Examples of $R^3$ and $R^4$ are the same as those enumerated for $R^1$, the substituent of $R^1$ and $R^2$.

$R^3$ particularly preferably has a stereoscopically small substituent to provide high fading speed. Therefore, particularly preferred $R^3$ is a hydrogen atom ("a" is 0).

Meanwhile, $R^4$ is preferably a hydrogen atom ("b" is 0) or an electron absorbing group as a high fading speed is obtained. When the group $R^4$ is an electron absorbing group, the group $R^4$ is preferably bonded to the 11-position carbon atom to further accelerate the fading speed. The preferred electron absorbing group is a cyano group or a haloalkyl group having 1 to 6 carbon atoms, as exemplified by cyano group and trifluoromethyl group.

"a" is an integer of 0 to 2 and indicates the number of $R^3$'s. When "a" is 2, two $R^3$'s may be the same or different. "b" is an integer of 0 to 4 and indicates the number of $R^4$'s. When "b" is an integer of 2 to 4, a plurality of $R^4$'s may be the same or different. When there are a plurality of $R^3$'s and a plurality of $R^4$'s, preferred $R^3$'s and $R^4$'s are the same as those enumerated above.

<$R^5$ and $R^6$>

$R^5$ and $R^6$ are each independently a group represented by the following formula (3), group represented by the following formula (4), aryl group, heteroaryl group or alkyl group.

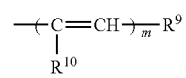

(3)

(4)

In the above formula (3), $R^9$ is an aryl group or a heteroaryl group. Examples of the aryl group and the heteroaryl group are the same as those enumerated for $R^1$.

$R^{10}$ is a hydrogen atom, alkyl group or halogen atom. Examples of the alkyl group include methyl group, ethyl group and propyl group. Examples of the halogen atom are fluorine atom, chlorine atom, bromine atom and iodine atom.

"m" is an integer of 1 to 3. "m" is preferably 1 from the viewpoint of the acquisition of raw materials.

Preferred examples of the group represented by the above formula (3) include phenyl-ethenyl group, (4-(N,N-dimethylamino)phenyl)-ethenyl group, (4-morpholinophenyl)-ethenyl group, (4-piperidinophenyl)-ethenyl group, (4-methoxyphenyl)-ethenyl group, (2-methoxyphenyl)-ethenyl group, phenyl-1-methylethenyl group, (4-methoxyphenyl)-1-methylethenyl group, phenyl-1-fluoroethenyl group, (4-(N,N-dimethylamino)phenyl)-1-fluoroethenyl group, 2-thienyl-ethenyl group, 2-furyl-ethenyl group, 2-(N-methyl)pyrrolinyl-ethenyl group, 2-benzothienyl-ethenyl group, 2-benzofuranyl-ethenyl group and 2-(N-methyl)indolyl-ethenyl group.

In the above formula (4), $R^{11}$ is an aryl group or a heteroaryl group. Examples of these groups are the same as those enumerated for $R^9$. "n" is an integer of 1 to 3. "n" is preferably 1 from the viewpoint of the easy acquisition of raw materials.

Preferred examples of the group represented by the above formula (4) include phenyl-ethynyl group, (4-(N,N-dimethylamino)phenyl)-ethynyl group, (4-morpholinophenyl)-ethynyl group, (4-piperidinophenyl)-ethynyl group, (4-methoxyphenyl)-ethynyl group, (4-methylphenyl)-ethynyl group, (2-methoxyphenyl)-ethynyl group, 2-thienyl-ethynyl group, 2-furyl-ethynyl group, 2-(N-methyl)pyrrolinyl-ethynyl group, 2-benzothienyl-ethynyl group, 2-benzofuranyl-ethynyl group and 2-(N-methyl)indolyl-ethynyl group.

Examples of the aryl group and the heteroaryl group represented by $R^5$ and $R^6$ are the same as those enumerated for $R^1$. Examples of the alkyl group are the same as those enumerated for the substituent of $R^1$.

$R^5$ and $R^6$ can be bonded together to form an aliphatic hydrocarbon ring together with the carbon atom bonded thereto.

Preferred examples of the aliphatic hydrocarbon ring include adamantane ring, bicyclononane ring, norbornane ring and fluorene ring.

To obtain excellent photochromic properties (double peak characteristic and fading speed), at least one of $R^5$ and $R^6$, preferably both are each desirably an aryl group or a heteroaryl group. Further, at least one of $R^5$ and $R^6$, preferably both are each desirably any one of the following groups (i) to (iv):
(i) aryl group or heteroaryl group having an alkyl group or an alkoxy group as a substituent
(ii) aryl group or heteroaryl group having an amino group as a substituent
(iii) aryl group or heteroaryl group having a heterocyclic group having a ring member nitrogen atom and bonded to an aryl group or a heteroaryl group via the nitrogen atom as a substituent In the above aryl groups (i) to (iii), the substitution positions and the total number of the substituents are not particularly limited. To obtain excellent photochromic properties, when the aryl group is a phenyl group, the substitution position is preferably the 3-position or the 4-position and the number of the substituents is preferably 1 to 2. Examples of the aryl group include 4-methylphenyl group, 4-methoxyphenyl group, 3,4-dimethoxyphenyl group, 4-n-propoxyphenyl group, 4-(N,N-dimethylamino)phenyl group, 4-(N,N-diethylamino)phenyl group, 4-(N,N-diphenylamino)phenyl group, 4-morpholinophenyl group, 4-piperidinophenyl group, 3-(N,N-dimethylamino)phenyl group and 4-(2,6-dimethylpiperidino)phenyl group.

In the above heteroaryl groups (i) to (iii), the substitution positions and the total number of the substituents are not particularly limited. The number of the substituents is preferably 1. Preferred examples of the heteroaryl group include 4-methoxythienyl group, 4-(N,N-dimethylamino)thienyl group, 4-methylfuryl group, 4-(N,N-diethylamino)furyl group, 4-(N,N-diphenylamino)thienyl group, 4-morpholinopyrrolinyl group, 6-piperidinobenzothienyl group and 6-(N,N-dimethylamino)benzofuryl group.

<$R^7$ and $R^8$>

$R^7$ and $R^8$ are each independently a hydrogen atom, hydroxyl group, alkyl group, haloalkyl group, cycloalkyl group, alkoxy group, amino group, heterocyclic group having a ring member nitrogen atom and bonded to the 13-position carbon atom via the nitrogen atom, cyano group, nitro group, formyl group, hydroxycarbonyl group, alkylcarbonyl group, alkoxycarbonyl group, halogen atom, aralkyl group, aralkoxy group, aryl group or aryloxy group.

Out of these, $R^7$ and $R^8$ are each preferably an alkyl group having 1 to 6 carbon atoms, haloalkyl group having 1 to 6 carbon atoms, cycloalkyl group having 3 to 15 carbon atoms, alkoxy group having 1 to 15 carbon atoms, amino group, heterocyclic group having a ring member nitrogen atom and bonded to the 13-position carbon atom bonded thereto via the nitrogen atom, alkylcarbonyl group having 2 to 7 carbon atoms, alkoxycarbonyl group having 2 to 7 carbon atoms, halogen atom, aralkyl, group having 7 to 11 carbon atoms, aralkoxy group having 7 to 11 carbon atoms, aryl group having 6 to 10 carbon atoms or aryloxy group having 6 to 10 carbon atoms. Examples of $R^7$ and $R^8$ are the same as those enumerated for $R^1$, the substituent of $R^1$ and $R^2$.

$R^7$ and $R^8$ may be bonded together to form an aliphatic ring having 3 to 20 ring member carbon atoms, condensed polycyclic ring having an aromatic ring or an aromatic hetero ring condensed to the above aliphatic ring, hetero ring having 3 to 20 ring member atoms, or condensed polycyclic ring having an aromatic ring or an aromatic hetero ring condensed to the above hetero ring together with the 13-position carbon atom bonded thereto.

Examples of the aliphatic ring having 3 to 20 ring member carbon atoms include cyclopentane ring, cyclohexane ring, cyclooctane ring, cycloheptane ring, norbornane ring, bicyclononane ring and adamantane ring.

Examples of the condensed polycyclic ring having an aromatic ring or an aromatic hetero ring condensed to the above aliphatic ring include phenanthrene ring.

Examples of the hetero ring having 3 to 20 ring member atoms include dihydrothiophene ring, dihydrofuran ring, tetrahydrofuran ring and dihydropyridine ring.

Examples of the condensed polycyclic ring having an aromatic ring or an aromatic hetero ring condensed to the above hetero ring include dihydrobenzofuran ring and dihydrobenzothiophene ring.

<Particularly Preferred $R^7$ and $R^8$>

In the present invention, examples of substituents of $R^7$ and $R^8$ are each preferably a hydroxyl group, alkyl group or alkoxy group, or form a ring together with the 13-position carbon atom bonded thereto. An example of the alkyl group is a methyl group and an example of the alkoxy group is a methoxy group. Out of these preferred substituents, $R^7$ and $R^8$ preferably form a ring together with the 13-position carbon atom to accelerate the fading speed and reduce initial coloration by thermochromism while retaining high color optical density and double peak characteristic. $R^7$ and $R^8$ preferably form the above aliphatic ring or the above condensed polycyclic ring having an aromatic ring or an aromatic hetero ring condensed to the above aliphatic ring as the fading speed becomes especially high. $R^7$ and $R^8$ particularly preferably form the above aliphatic ring as the fading speed becomes the highest and initial coloration by thermochromism reduces.

The particularly preferred aliphatic ring formed by $R^7$ and $R^8$ is an aliphatic hydrocarbon ring, and the aliphatic hydrocarbon ring preferably has 3 to 20 ring member carbon atoms. This aliphatic hydrocarbon ring may have at least one substituent selected from the group consisting of alkyl group having 1 to 6 carbon atoms, haloalkyl group having 1 to 6 carbon atoms, cycloalkyl group having 3 to 15 carbon atoms, alkoxy group having 1 to 15 carbon atoms, amino group, aralkyl group having 7 to 11 carbon atoms, aryl group having 6 to 10 carbon atoms and halogen atom. This substituted aliphatic hydrocarbon ring is also preferred. Examples of the alkyl group, haloalkyl group, cycloalkyl group, alkoxy group, amino group, aralkyl group, aryl group and halogen atom are the same as those enumerated for $R^1$, the substituent of $R^1$ and $R^2$.

More preferred examples of the aliphatic hydrocarbon ring include monocyclo rings such as cyclopentane ring, cyclohexane ring, cycloheptane ring, cyclooctane ring and cyclononane ring, bicyclo rings such as norbornane ring and bicyclononane ring, and tricyclo rings such as adamantane ring. Aliphatic hydrocarbon rings having at least one lower alkyl group with 4 or less carbon atoms such as methyl group are also preferred. Out of these, a monocyclo ring exhibits a particularly excellent effect as it reduces initial coloration by thermochromism while retaining high color optical density, high double peak characteristic and high fading speed.

In the present invention, the most preferred examples of the ring formed by bonding together the groups $R^7$ and $R^8$ together with the 13-position carbon atom bonded thereto are rings represented by the following formulas. In the following formulas, the carbon atom at a position denoted by 13 is the 13-position carbon atom of the above pyran structure.

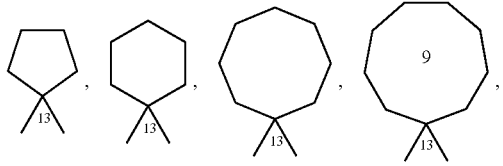

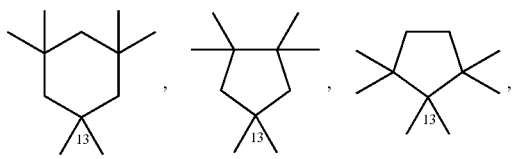

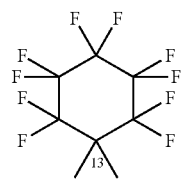

Out of the above monocyclo rings, cyclooctane ring, cyclononane ring and 3,3,5,5-tetramethylcyclohexane ring are most preferred.

(Preferred Examples of Chromene Compound)

In the present invention, particularly preferred examples of the chromene compound are the following compounds.

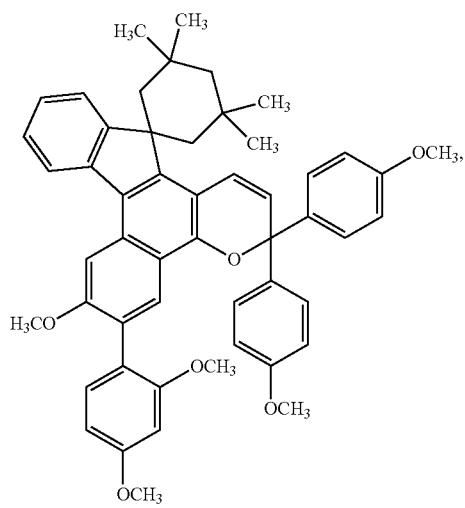

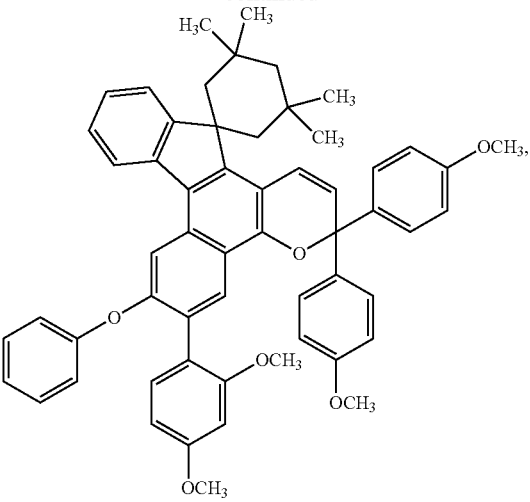

-continued

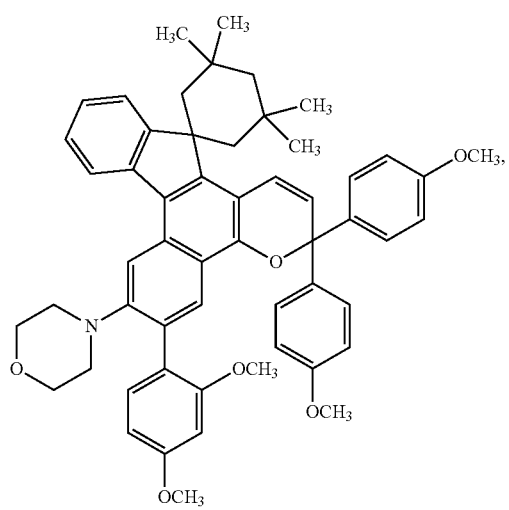

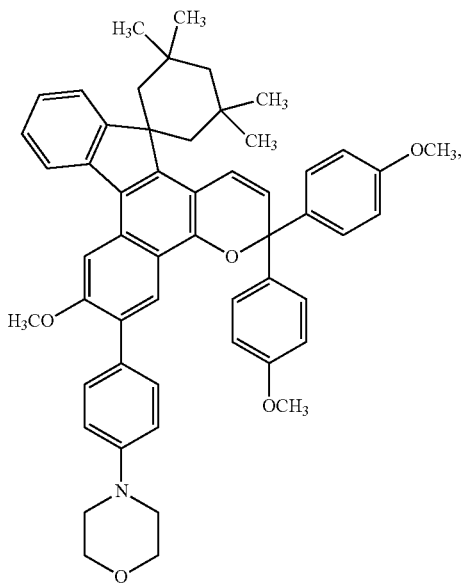

-continued

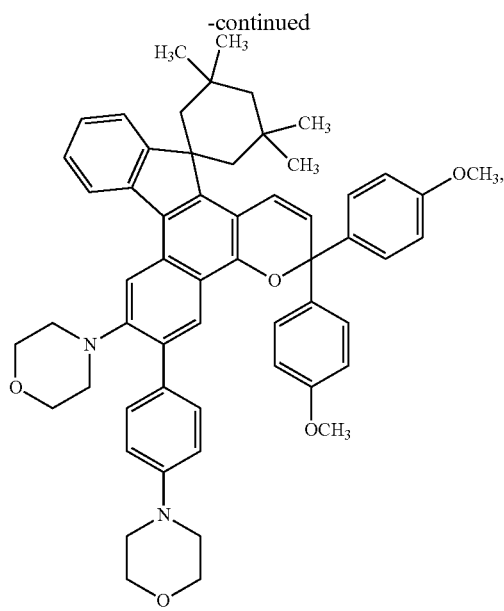

(Identification of Chromene Compound)

In general, the chromene compound of the present invention is existent as an achromatic, light yellow or light green solid or viscous liquid at normal temperature and normal pressure and can be confirmed by the following means (1) to (3).

(1) When the proton nuclear magnetic resonance spectrum ($^1$H-NMR) of the chromene compound is measured, peaks based on an aromatic proton and the proton of an alkene appear at δ of around 5.0 to 9.0 ppm and peaks based on the protons of an alkyl group and an alkylene group appear at δ of around 1.0 to 4.0 ppm. By comparing these spectral intensities relatively, the number of the protons of each bond can be known.

(2) The composition of a corresponding product can be determined by elemental analysis.

(3) When the $^{13}$C-nuclear magnetic resonance spectrum ($^{13}$C-NMR) of the chromene compound is measured, a peak based on the carbon of an aromatic hydrocarbon group appears at δ of around 110 to 160 ppm, peaks based on the carbons of an alkene and an alkyne appear at δ of around 80 to 140 ppm, and peaks based on the carbons of an alkyl group and an alkylene group appear at δ of around 20 to 80 ppm.

(Production of Chromene Compound)

The chromene compound of the present invention may be produced by any synthesis method. For example, the chromene compound represented by the above formula (2) can be advantageously produced by the following method. In the following description, symbols in the formulas are as defined in the above formulas unless otherwise stated.

The chromene compound can be advantageously produced by reacting a naphthol compound represented by the following formula (5) with a propargyl alcohol compound represented by the following formula (6) in the presence of an acid catalyst.

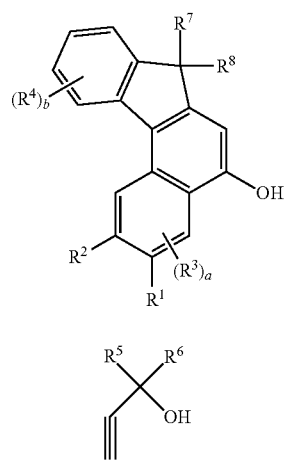

The reaction ratio of the naphthol compound to the propargyl alcohol compound is preferably selected from a range of 1:10 to 10:1 (molar ratio). The acid catalyst is preferably selected from sulfuric acid, benzenesulfonic acid, p-toluenesulfonic acid and acid alumina. The acid catalyst is preferably used in an amount of 0.1 to 10 parts by weight based on 100 parts by weight of the total of the naphthol compound and the propargyl alcohol compound. The reaction temperature is preferably 0 to 200° C. An aprotic organic solvent such as N-methylpyrrolidone, dimethyl formamide, tetrahydrofuran, benzene or toluene is preferably used as the solvent. The method of purifying the product obtained by the above reaction is not particularly limited. For example, the product is subjected to silica gel column purification and further purified by re-crystallization.

The naphthol compound represented by the above formula (5) is provided as a novel compound by the present invention.

Preferred examples of the naphthol compound represented by the above formula (5) are compounds represented by the following formulas.

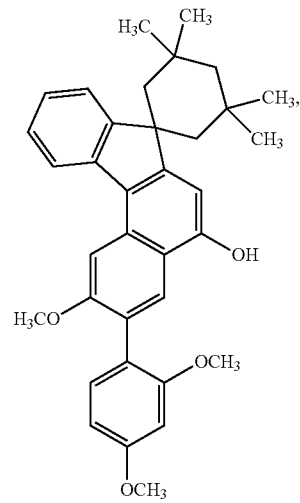

-continued

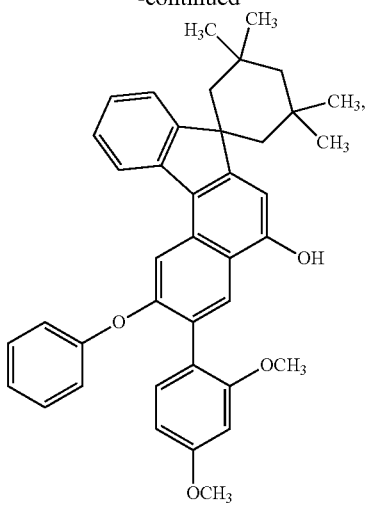

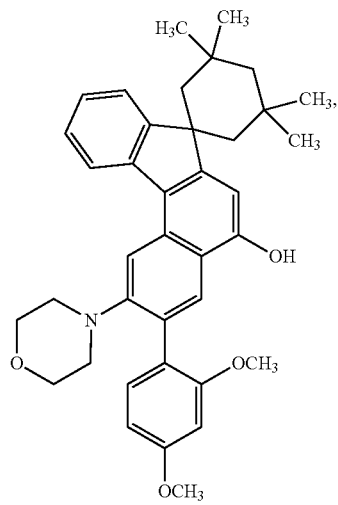

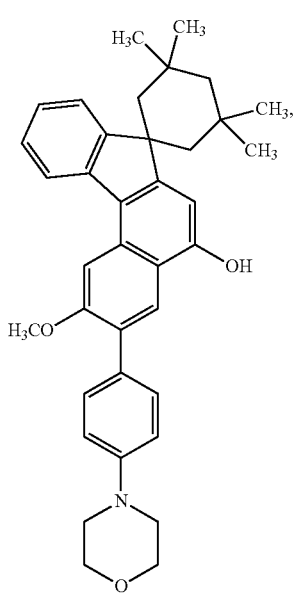

-continued

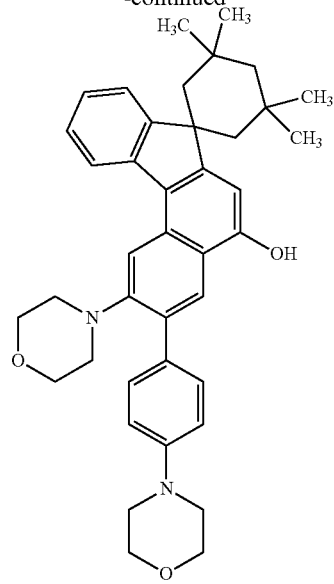

Ordinary naphthol compounds can be synthesized based on reaction methods described in research papers such as a pamphlet of International Laid-Open WO01/60881 and a pamphlet of International Laid-Open WO05/028465.

The naphthol compound represented by the above formula (5) can be synthesized as follows, for example.

First of all, a carboxylic acid represented by the following formula (7) may be purchased as a commercially available product or may be synthesized based on the following documents ($R^3$ and "a" are as defined in the above formula (2). $X^1$ is a chlorine atom, bromine atom, iodine atom or the same group as $R^1$ in the formula (2). $X^2$ is a chlorine atom, bromine atom, iodine atom or the same group as $R^2$ in the formula (2)).

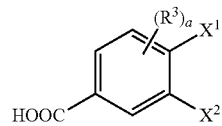

(7)

For example, a carboxylic acid represented by the following formula (8) can be purchased as a commercially available product.

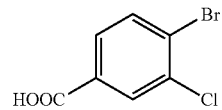

(8)

For example, a carboxylic acid represented by the following formula (9) can be synthesized based on a reaction method described in research papers such as Journal of the Chemical Society. 20-27; 1927.

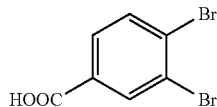
(9)

The compound (7) is converted into acid chloride by using thionyl chloride or oxalyl chloride, the acid chloride is reacted with a Grignard reagent to produce a compound represented by the following formula (10) ($R^4$ and "b" are as defined in the above formula (2)), and then when $X^1$ and $X^2$ are each a chlorine atom, bromine atom or iodine atom, they are converted into desired $R^1$ and $R^2$ by making use of a Suzuki-Miura reaction or a Buchwald-Hartwig cross-coupling reaction to obtain a compound represented by the following formula (11).

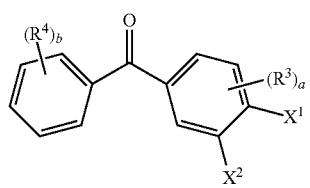
(10)

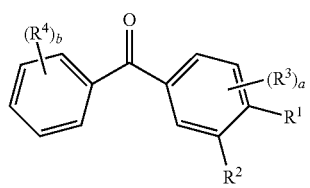
(11)

The above compound (11) is subjected to a Stobbe reaction and a cyclization reaction to obtain a compound represented by the following formula (12).

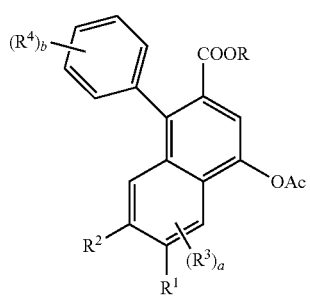
(12)

In the compound of the formula (12), R is a group derived from a diester compound used in the Stobbe reaction. Then, the compound (12) is hydrolyzed by using an alkali or acid to obtain a carboxylic acid represented by the following formula (13).

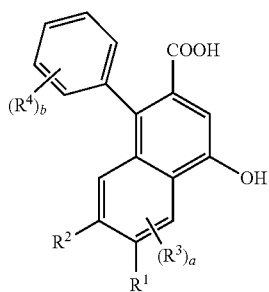
(13)

The carboxylic acid is benzylated by using a base such as potassium carbonate and benzyl chloride and then hydrolyzed by using an alkali or acid to obtain a benzyl protected carboxylic acid represented by the following formula (14).

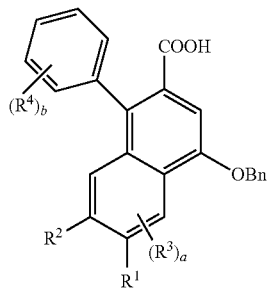
(14)

The benzyl protected carboxylic acid is converted into an amine by a method such as Curtius rearrangement, Hofmann rearrangement or Lossen rearrangement, and a diazonium salt is prepared from the amine by a method known per se. This diazonium salt is converted into a bromide through a Sandmeyer reaction or the like, and the obtained bromide is reacted with magnesium or lithium to prepare an organic metal compound. This organic metal compound is reacted with a ketone represented by the following formula (15) ($R^7$ and $R^8$ are as defined in the above formula (2)) at −80 to 70° C. in an organic solvent for 10 minutes to 4 hours and then subjected to a debenzylation reaction with hydrogen and palladium carbon to obtain an alcohol represented by the following formula (16).

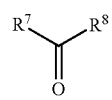
(15)

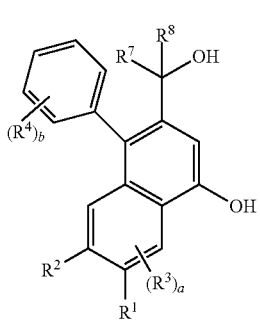

(16)

The Friedel-Crafts reaction of this alcohol is carried out at 10 to 120° C. for 10 minutes to 2 hours under a neutral to acid condition to synthesize a naphthol compound of interest represented by the above formula (5). In the above reaction, the reaction ratio of the above organic metal compound to the ketone represented by the above formula (15) is preferably selected from a range of 1:10 to 10:1 (molar ratio). The reaction temperature is preferably −80 to 70° C. An aprotic organic solvent such as diethyl ether, tetrahydrofuran, benzene or toluene is preferably used as the solvent. The Friedel-Crafts reaction of the alcohol represented by the above formula (16) under the neutral to acid condition is preferably carried out by using an acid catalyst such as acetic acid, hydrochloric acid, sulfuric acid, benzenesulfonic acid, p-toluenesulfonic acid or acid alumina. The acid catalyst is preferably used in an amount of 0.1 to 10 parts by weight based on 100 parts by weight of the alcohol of the above formula (16). For this reaction, an aprotic organic solvent such as tetrahydrofuran, benzene or toluene is used.

The propargyl alcohol compound represented by the above formula (6) can be easily synthesized, for example, by reacting a ketone compound corresponding to the above formula (6) with a metal acetylene compound such as lithium acetylide.

The chromene compound of the present invention which is synthesized as described above dissolves well in an ordinary organic solvent such as toluene, chloroform or tetrahydrofuran. When the chromene compound represented by the above formula (1) is dissolved in this solvent, the obtained solution is generally almost achromatic and transparent and shows an excellent photochromic function that it develops a color swiftly upon exposure to sunlight or ultraviolet light and reversibly returns to its original achromatic state swiftly by blocking the light.

(Combination with Another Photochromic Compound>

Although the chromene compound of the present invention develops a color of a neutral tint by itself, it may be used in combination with another photochromic compound to obtain various colors required as a photochromic lens. Any known compound may be used without restrictions as the photochromic compound to be combined with. Examples of the photochromic compound include fulgide, fulgimide, spirooxazine and chromene. Out of these, a chromene compound is particularly preferred because it can keep a color uniform at the time of color development and fading, can suppress a color shift at the time of color development due to the deterioration of photochromic properties and further can reduce initial coloration.

That is, by combining the chromene compound of the present invention with another chromene compound which has high color development sensitivity, a high fading speed and little initial coloration like the above chromene compound, a photochromic composition which keeps a color uniform at the time of color development and fading and provides high transparency can be obtained.

To provide high transparency, the chromene compound to be combined with preferably has a transmittance by thermochromism of not less than 75% and an absorption end of an ultraviolet absorption curve at 380 to 430 nm. Further, a chromene compound having a transmittance by thermochromism of not less than 85% and an absorption end of an ultraviolet absorption curve at 380 to 420 nm is particularly preferred, and a chromene compound having a transmittance by thermochromism of not less than 88% and an absorption end of an ultraviolet absorption curve at 380 to 410 nm is most preferred. The transmittance by thermochromism and the absorption end of the ultraviolet absorption curve are values measured by methods described in the following examples.

These preferred chromene compounds to be combined with include chromene compounds represented by the following formulas (17) and (18).

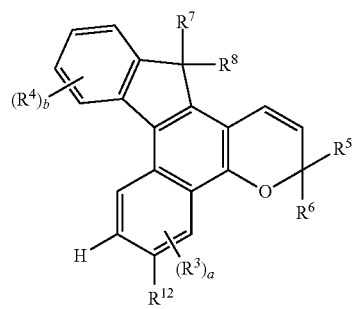

(17)

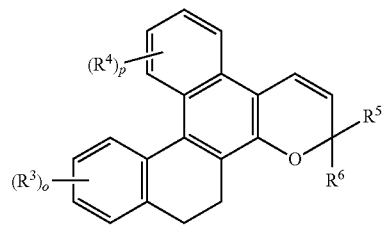

(18)

In the above formula (17), $R^3$, $R^4$, $R^5$, $R^6$, $R^7$, $R^8$, "a" and "b" are as defined in the above formula (2), and $R^{12}$ is a hydrogen atom, hydroxyl group, alkyl group, haloalkyl group, cycloalkyl group, alkoxy group, amino group, heterocyclic group having a ring member nitrogen atom and bonded to a benzene ring bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group. Specific examples of the chromene compound of the above formula (17) include compounds described in a pamphlet of International Laid-Open WO2001/60811.

In the above formula (18), $R^3$, $R^4$, $R^5$ and $R^6$ are as defined in the above formula (2), and "o" and "p" are each independently an integer of 0 to 4. Specific examples of the chromene compound of the above formula (18) include compounds described in a pamphlet of International Laid-Open WO2009/136668.

To obtain a photochromic composition comprising the chromene compound of the present invention and another photochromic compound, the ratio of these chromene compounds may be suitably determined according to a desired color. In this case, it is preferred that the amount of the chromene compound of the present invention or another chromene compound should be 0.001 to 10 parts by mass based on 100 parts by mass of the total of all the polymerizable monomers. Stated more specifically, more preferably, in the case of a thin film such as a coating film (for example, a thin film having a thickness of about 100 μm), color should be controlled by using 0.001 to 5.0 parts by mass of the chromene compound of the present invention and 0.001 to 5.0 parts by mass of another chromene compound based on 100 parts by mass of the coating film or all of the polymerizable monomers which provide the coating film. In the case of a thick cured material (having a thickness of 1 mm or more, for example), color should be controlled by using 0.001 to 0.5 part by mass of the chromene compound of the present invention and 0.001 to 0.5 part by mass of another chromene compound based on 100 parts by mass of the thick cured material or all of the polymerizable monomers which provide the thick cured material.

(Stabilizer to be Combined with)

Although the chromene compound of the present invention has high durability as it is, its durability can be further enhanced by using the following ultraviolet absorbent, optical stabilizer or antioxidant. As the ultraviolet absorbent may be used known ultraviolet absorbents such as benzophenone-based compounds, benzotriazole-based compounds, cyanoacrylate-based compounds, triazine-based compounds and benzoate-based compounds. Cyanoacrylate-based compounds and benzophenone-based compounds are particularly preferred. When the above ultraviolet absorbent is used in an amount of 0.001 to 5 parts by mass based on 100 parts by mass of the total of all the polymerizable monomers including the chromene compound of the present invention, it produces an effect. Known hindered amines may be used as the optical stabilizer, and known hindered phenols may be used as the antioxidant. When the above optical stabilizer and antioxidant are each used in an amount of 0.01 to 10 parts by mass based on 100 parts by mass of the total of all the polymerizable monomers including the chromene compound of the present invention, they produce an effect.

(Use of Chromene Compound)

A photochromic composition comprising the chromene compound of the present invention and a chromene compound represented by the above formula (1) (17) or (18) exhibits the same photochromic properties even in a polymer solid matrix. The polymer solid matrix is not particularly limited if the chromene compound of the present invention can be uniformly dispersed therein. Examples of the polymer compound optically preferred for the polymer solid matrix include thermoplastic resins such as methyl polyacrylate, ethyl polyacrylate, methyl polymethacrylate, ethyl polymethacrylate, polystyrene, polyacrylonitrile, polyvinyl alcohol, polyacrylamide, poly(2-hydroxyethylmethacrylate), polydimethylsiloxane and polycarbonate.

A photochromic composition can also be prepared by mixing the photochromic composition comprising the chromene compound of the present invention and the chromene compound represented by the above formula (1), (17) or (18) with various polymerizable monomers before polymerization to prepare a photochromic curable composition and polymerizing and curing it. That is, a cured material containing the photochromic composition uniformly dispersed therein can be obtained by polymerizing and curing the photochromic curable composition comprising the photochromic composition of the present invention and various polymerizable monomers.

A photochromic curable composition which is prepared by mixing together the photochromic composition comprising the chromene compound represented by the above formula (1), (17) or (18) with the following polymerizable monomers (A1), (A2) and (A3) and provides a cured material having an L scale Rockwell hardness of not less than 60 is particularly preferred because it exhibits excellent photochromic properties such as high color optical density and high fading speed and obtains excellent substrate properties such as high hardness and high heat resistance:

(A1) a polymerizable monomer which has an L scale Rockwell hardness of a polymer obtained by homopolymerizing it of not more than 40, (A2) a trifunctional or higher functional radically polymerizable monomer which has an L scale Rockwell hardness of a polymer obtained by homopolymerizing it of not less than 60, and (A3) a bifunctional radically polymerizable monomer having an L scale Rockwell hardness of a polymer obtained by homopolymerizing it of not less than 60.

Examples of the component (A1) include acrylate compounds and methacrylate compounds such as glycidyl acrylate, glycidyl methacrylate, β-methylglycidyl methacrylate, bisphenol A-monoglycidyl ether-methacrylate, 4-glycidyloxy methacrylate, 3-(glycidyl-2-oxyethoxy)-2-hydroxypropyl methacrylate, 3-(glycidyloxy-1-isopropyloxy)-2-hydroxypropyl acrylate and 3-glycidyloxy-2-hydroxypropyloxy)-2-hydroxypropyl acrylate, and polyalkylene glycol compounds such as polyethylene glycol diacrylate; examples of the component (A2) include polyacrylate and polymethacrylate compounds such as trimethylolpropane trimethacrylate, urethane acrylates such as urethane oligomer tetramethacrylate, and polyester acrylates such as polyester oligomer hexaacrylate; and examples of the component (A3) include polyacrylate and polymethacrylate compounds such as ethylene glycol diacrylate, diethylene glycol dimethacrylate, triethylene glycol dimethacrylate, tetraethylene glycol dimethacrylate, ethylene glycol bisglycidyl methacrylate, bisphenol A dimethacrylate, 2,2-bis(4-methacryloyloxyethoxyphenyl)propane and 2,2-bis(3,5-dibromo-4-methacryloyloxyethoxyphenyl)propane, all of which are polymerizable monomers described in a pamphlet of International Laid-Open WO2001/05854. The term "L scale Rockwell hardness" means hardness measured in accordance with JIS-B7726, and it can be easily judged whether the above hardness condition is satisfied or not by measuring the homopolymer of each monomer.

Copolymers obtained by copolymerizing the above polymerizable monomers with polymerizable monofunctional monomers may also be used as the above polymer matrix. The polymerizable monofunctional monomers include unsaturated carboxylic acids such as acrylic acid, methacrylic acid and maleic anhydride; polyallyl compounds such as diallyl phthalate, diallyl terephthalate, diallyl isophthalate, diallyl tartarate, diallyl epoxysuccinate, diallyl fumarate, diallyl chlorendate, diallyl hexaphthalate, diallyl carbonate, allyl diglycol carbonate and trimethylolpropane triallyl carbonate; polythioacrylate and polythiomethacrylate compounds such as 1,2-bis(methacryloylthio)ethane, bis(2-acryloylthioethyl) ether and 1,4-bis(methacryloylthiomethyl)benzene; acrylate and methacrylate compounds such as methyl acrylate, methyl methacrylate, benzyl methacrylate, phenyl methacrylate and 2-hydroxyethyl methacrylate; fumarate compounds such as diethyl fumarate and diphenyl fumarate; thioacrylate and thiomethacrylate compounds such as methyl thioacrylate, benzyl thioacrylate and benzyl thiomethacrylate; and vinyl compounds such as styrene, chlorostyrene, methyl styrene, vinyl naphthalene, α-methylene dimer and bromostyrene. These monomers may be used alone or in combination of two or more, and the amount of the monomer may be suitably determined according to its use purpose.

The method of dispersing the chromene compound of the present invention into the above polymer solid matrix is not particularly limited, and commonly used methods may be employed. The methods include one in which the above thermoplastic resin and the chromene compound are kneaded together while they are molten to disperse the chromene compound into the resin, one in which the chromene compound is dissolved in the above polymerizable monomers and a polymerization catalyst is added to polymerize the polymerizable monomers by heat or light so as to disperse the chromene compound into the resin, and one in which the surfaces of the above thermoplastic resin and the above thermosetting resin are dyed with the chromene compound to disperse the chromene compound into the resins.

(Other Applications of Chromene Compound of the Present Invention)

The chromene compound of the present invention can be used as a photochromic material in a wide range of fields such as recording materials as substitutes for silver halide photosensitive materials, copy materials, printing photosensitive materials, recording materials for cathode ray tubes, photosensitive materials for lasers and photosensitive materials for holography. The photochromic material comprising the chromene compound of the present invention may also be used as a photochromic plastic lens material, optical filter material, display material or material for actinometers and ornaments.

For instance, when the chromene compound of the present invention is used in a photochromic lens, a method in which uniform light control performance is obtained, for example, a method in which a polymer film containing the photochromic material of the present invention uniformly dispersed therein is sandwiched between lenses, a method in which the chromene compound of the present invention is dispersed into the above polymerizable monomers and the polymerizable monomers are polymerized by a predetermined technique, or a method in which the chromene compound of the present invention is dissolved in, for example, silicone oil, the resulting solution is impregnated into the surface of a lens at 150 to 200° C. over 10 to 60 minutes, and the surface is further coated with a curable substance to obtain a photochromic lens may be employed. Further, a method in which the above polymer film is formed on the surface of a lens and the surface is coated with a curable substance to obtain a photochromic lens is also employed.

Further, a coating agent composed of a polymerization curable composition comprising the chromene compound of the present invention may be applied to the surface of a lens substrate, and the coating film may be cured. At this point, the lens substrate may be subjected to a surface treatment with an alkaline solution or a plasma treatment in advance, and a primer may be further applied to improve adhesion between the substrate and the coating film (by carrying out the above surface treatment or without the surface treatment).

EXAMPLES

The following examples are provided for the purpose of further illustrating the present invention but are in no way to be taken as limiting.

Example 1

1.20 g (2.3 mmol) of a naphthol compound represented by the following formula (19) and 0.80 g (3.0 mmol) of a propargyl alcohol compound represented by the following formula (20) were dissolved in 70 ml of toluene, 0.022 g of p-toluenesulfonic acid was further added to the resulting solution, and the obtained mixture was stirred under reflux by heating for 1 hour.

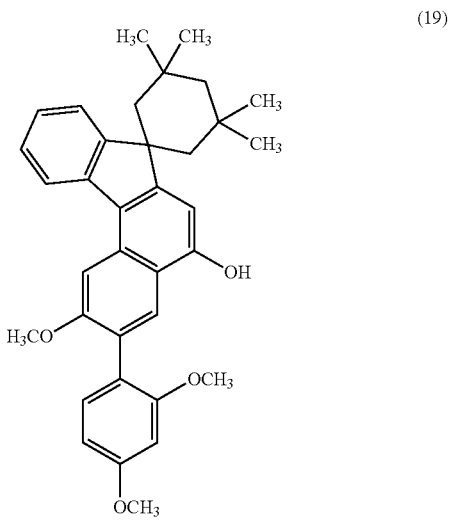

(19)

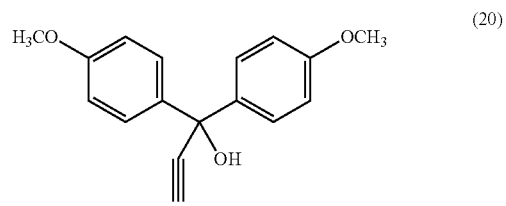

(20)

After the reaction, the solvent was removed, and the obtained product was purified by chromatography on silica gel to obtain 1.35 g of a white powder product. The yield rate was 76%.

The elemental analysis values of this product were 80.70% of C, 6.79% of H and 12.51% of O which were almost equal to the calculated values of $C_{52}H_{52}O_6$ (C: 80.80%, H: 6.78%, O: 12.42%).

When the proton nuclear magnetic resonance spectrum of the product was measured, it showed 18H peaks based on the methyl proton of a tetramethylcyclohexane ring and a methylene proton at δ of around 1.0 to 3.0 ppm, a 15H peak based on the methyl proton of a methoxy group at δ of around 2.3 to 4.5 ppm and 19H peaks based on an aromatic proton and the proton of an alkene at δ of around 5.6 to 9.0 ppm. Further, when the $^{13}C$-nuclear magnetic resonance spectrum was measured, it showed a peak based on the carbon of an aromatic ring at δ of around 110 to 160 ppm, a peak based on the carbon of an alkene at δ of around 80 to 140 ppm and a peak based on the carbon of an alkyl at δ of around 20 to 60 ppm.

It was confirmed from the above results that the isolated product was a compound represented by the following formula (21).

27

(21)

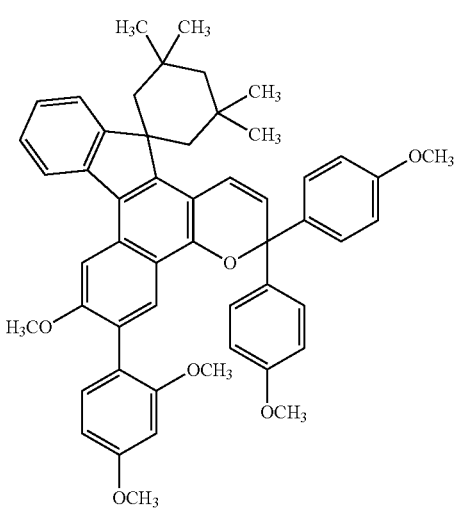

28

Examples 2 to 15

Chromene compounds shown in Table 1 (Examples 2 to 15) were synthesized in the same manner as in Example 1. When the structures of the obtained products were analyzed by using the same structure confirming means as in Example 1, it was confirmed that they were compounds represented by structural formulas shown in Table 1. Table 2 shows the elemental analysis values, calculated values obtained from the structural formulas of the compounds and characteristic $^1$H-NMR spectra of these compounds.

TABLE 1

| Example No. | Raw materials | | Product | Yield rate % |
|---|---|---|---|---|
| | Naphthol derivative | Propargyl alcohol derivative | | |
| 2 | | | | 70 |
| 3 | | | | 69 |

TABLE 1-continued
| Example No. | Naphthol derivative | Propargyl alcohol derivative | Product | Yield rate % |
|---|---|---|---|---|
| 4 | 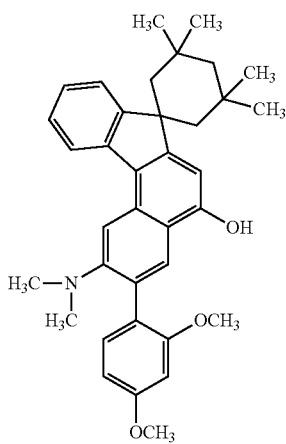 | 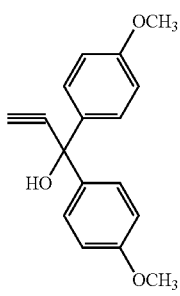 [SMILES: C#CC(O)(c1ccc(OC)cc1)c1ccc(OC)cc1] | 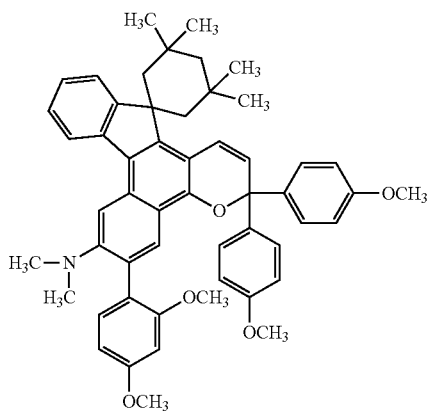 [SMILES: COc1ccc(C2(c3ccc(OC)cc3)C=Cc3c4c(c5cc(N(C)C)c(-c6ccc(OC)cc6OC)cc5c3O2)-c2ccccc2C42CC(C)(C)CC(C)(C)C2)cc1] | 70 |
| 5 | 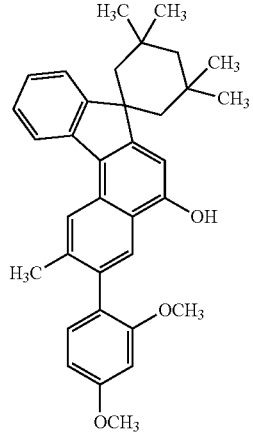 [SMILES: COc1ccc(-c2cc3c(O)cc4c(c3cc2C)-c2ccccc2C42CC(C)(C)CC(C)(C)C2)c(OC)c1] | 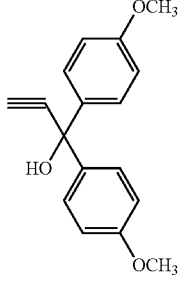 [SMILES: C#CC(O)(c1ccc(OC)cc1)c1ccc(OC)cc1] | 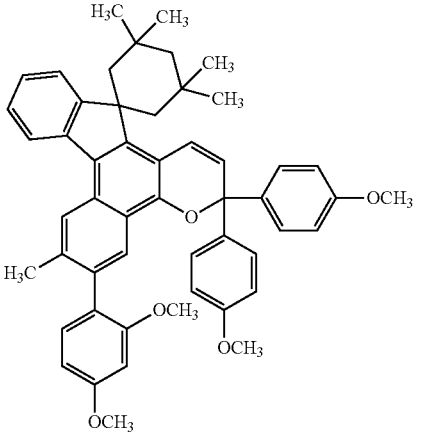 [SMILES: COc1ccc(C2(c3ccc(OC)cc3)C=Cc3c4c(c5cc(C)c(-c6ccc(OC)cc6OC)cc5c3O2)-c2ccccc2C42CC(C)(C)CC(C)(C)C2)cc1] | 73 |
| 6 | 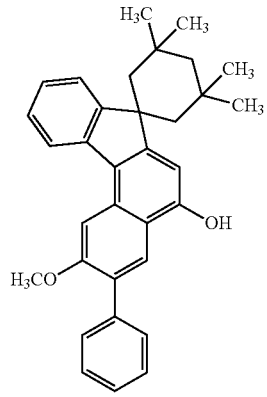 [SMILES: COc1cc2c3c(cc(O)c2cc1-c1ccccc1)C1(CC(C)(C)CC(C)(C)C1)c1ccccc1-3] | 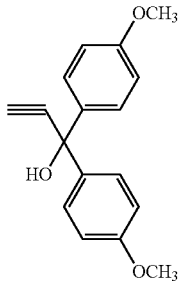 | 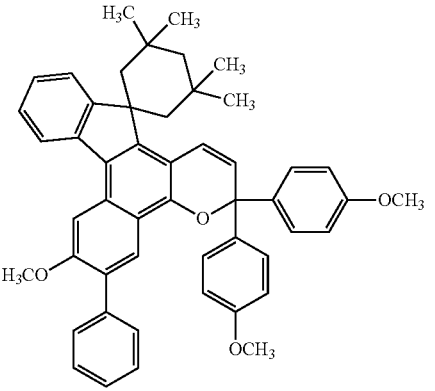 [SMILES: COc1ccc(C2(c3ccc(OC)cc3)C=Cc3c4c(c5cc(OC)c(-c6ccccc6)cc5c3O2)-c2ccccc2C42CC(C)(C)CC(C)(C)C2)cc1] | 71 |

TABLE 1-continued
| Example No. | Naphthol derivative | Propargyl alcohol derivative | Product | Yield rate % |
|---|---|---|---|---|
| 7 | 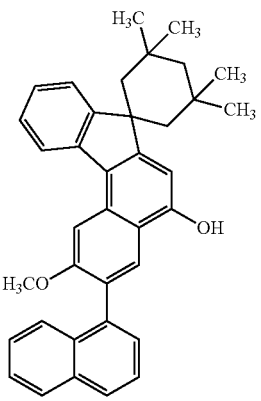 [SMILES: COc1cc2c3c(cc(O)c2cc1-c1cccc2ccccc12)C1(CC(C)(C)CC(C)(C)C1)c1ccccc1-3] | 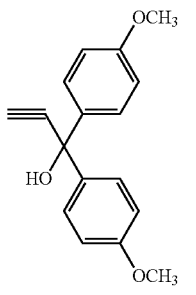 [SMILES: C#CC(O)(c1ccc(OC)cc1)c1ccc(OC)cc1] | 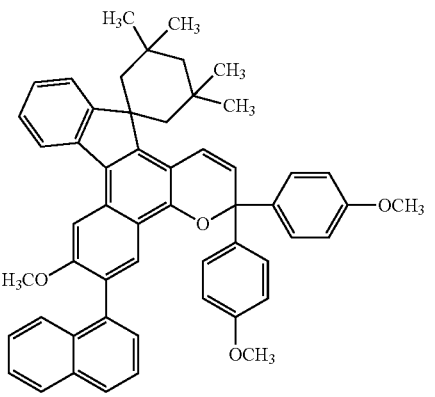 [SMILES: COc1ccc(C2(c3ccc(OC)cc3)C=Cc3c4c(c5cc(OC)c(-c6cccc7ccccc67)cc5c3O2)-c2ccccc2C42CC(C)(C)CC(C)(C)C2)cc1] | 75 |
| 8 | 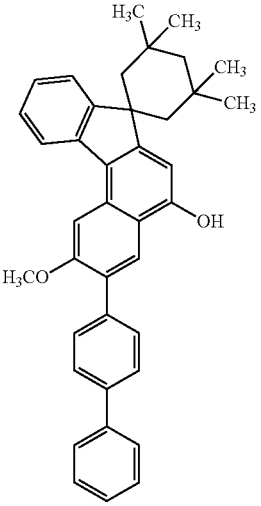 [SMILES: COc1cc2c3c(cc(O)c2cc1-c1ccc(-c2ccccc2)cc1)C1(CC(C)(C)CC(C)(C)C1)c1ccccc1-3] | 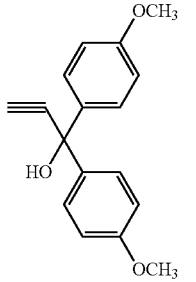 [SMILES: C#CC(O)(c1ccc(OC)cc1)c1ccc(OC)cc1] | 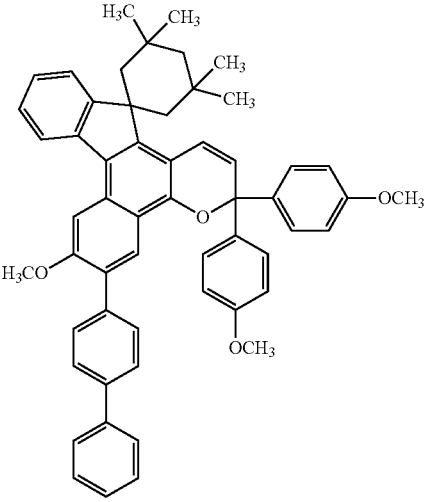 [SMILES: COc1ccc(C2(c3ccc(OC)cc3)C=Cc3c4c(c5cc(OC)c(-c6ccc(-c7ccccc7)cc6)cc5c3O2)-c2ccccc2C42CC(C)(C)CC(C)(C)C2)cc1] | 75 |
| 9 | 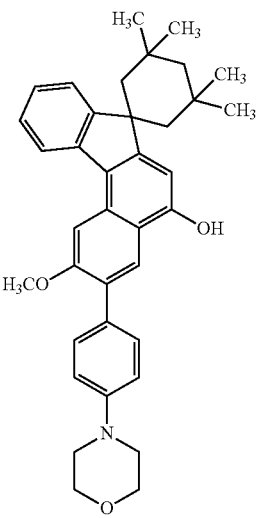 [SMILES: COc1cc2c3c(cc(O)c2cc1-c1ccc(N2CCOCC2)cc1)C1(CC(C)(C)CC(C)(C)C1)c1ccccc1-3] | 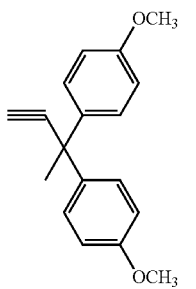 [SMILES: C#CC(C)(c1ccc(OC)cc1)c1ccc(OC)cc1] | 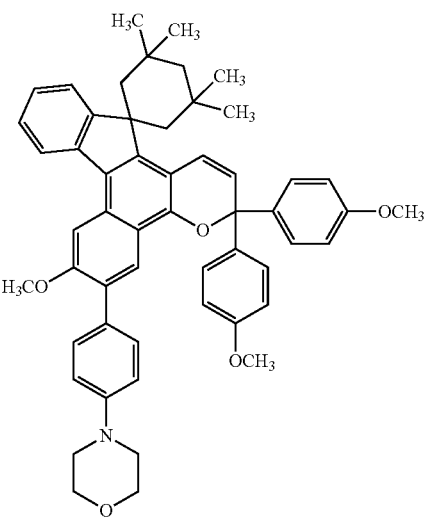 [SMILES: COc1ccc(C2(c3ccc(OC)cc3)C=Cc3c4c(c5cc(OC)c(-c6ccc(N7CCOCC7)cc6)cc5c3O2)-c2ccccc2C42CC(C)(C)CC(C)(C)C2)cc1] | 72 |

TABLE 1-continued

| Example No. | Raw materials | | Product | Yield rate % |
|---|---|---|---|---|
| | Naphthol derivative | Propargyl alcohol derivative | | |
| 10 | (structure) | (structure) | (structure) | 71 |
| 11 | (structure) | (structure) | (structure) | 74 |
| 12 | (structure) | (structure) | (structure) | 74 |

TABLE 1-continued

| Example No. | Raw materials — Naphthol derivative | Propargyl alcohol derivative | Product | Yield rate % |
|---|---|---|---|---|
| 13 | | | | 72 |
| 14 | | | | 70 |
| 15 | | | | 73 |

TABLE 2

| Example No. | Elemental analysis values | | | | | | | | ¹H-NMR (NMR) |
| | Experimental values | | | | Calculated values | | | | |
| | C | H | N | O | C | H | N | O | |
|---|---|---|---|---|---|---|---|---|---|
| 2 | 82.03 | 6.66 | 0.00 | 11.31 | 81.99 | 6.52 | 0.00 | 11.50 | δ5.0-9.0 24H<br>δ0.5-4.5 30H |

TABLE 2-continued

| Example No. | Elemental analysis values | | | | | | | | $^1$H-NMR (NMR) |
|---|---|---|---|---|---|---|---|---|---|
| | Experimental values | | | | Calculated values | | | | |
| | C | H | N | O | C | H | N | O | |
| 3 | 79.89 | 6.89 | 1.67 | 11.55 | 79.78 | 6.94 | 1.69 | 11.59 | δ5.0-9.0 19H<br>δ0.5-4.5 38H |
| 4 | 81.08 | 6.99 | 1.73 | 10.20 | 80.99 | 7.05 | 1.78 | 10.18 | δ5.0-9.0 19H<br>δ0.5-4.5 36H |
| 5 | 82.44 | 6.99 | 0.00 | 10.58 | 82.51 | 6.92 | 0.00 | 10.57 | δ5.0-9.0 19H<br>δ0.5-4.5 33H |
| 6 | 84.22 | 6.87 | 0.00 | 8.91 | 84.24 | 6.79 | 0.00 | 8.98 | δ5.0-9.0 21H<br>δ0.5-4.5 27H |
| 7 | 85.02 | 6.71 | 0.00 | 8.27 | 85.01 | 6.61 | 0.00 | 8.39 | δ5.0-9.0 23H<br>δ0.5-4.5 27H |
| 8 | 85.29 | 6.68 | 0.00 | 8.03 | 85.25 | 6.64 | 0.00 | 8.11 | δ5.0-9.0 25H<br>δ0.5-4.5 27H |
| 9 | 81.19 | 6.99 | 1.71 | 10.11 | 81.27 | 6.95 | 1.76 | 10.02 | δ5.0-9.0 20H<br>δ0.5-4.5 35H |
| 10 | 79.80 | 5.91 | 0.00 | 14.29 | 79.86 | 5.96 | 0.00 | 14.18 | δ5.0-9.0 19H<br>δ0.5-4.5 21H |
| 11 | 77.98 | 5.54 | 0.00 | 16.48 | 77.86 | 5.64 | 0.00 | 16.50 | δ5.0-9.0 19H<br>δ0.5-4.5 19H |
| 12 | 79.80 | 6.24 | 1.73 | 12.23 | 79.67 | 6.30 | 1.79 | 12.25 | δ5.0-9.0 19H<br>δ0.5-4.5 30H |
| 13 | 76.27 | 5.52 | 0.00 | — | 76.35 | 5.49 | 0.00 | 8.30 | δ5.0-9.0 19H<br>δ0.5-4.5 23H |
| 14 | 76.32 | 5.97 | 3.52 | 14.19 | 76.32 | 5.89 | 3.56 | 14.23 | δ5.0-9.0 17H<br>δ0.5-4.5 29H |
| 15 | 82.04 | 6.66 | 0.00 | 11.30 | 82.02 | 6.60 | 0.00 | 11.38 | δ5.0-9.0 19H<br>δ0.5-4.5 27H |

Examples 16 to 30

Evaluation of Physical Properties of Photochromic Plastic Lens Produced by Coating Method The chromene compound obtained in Example 1 was mixed with a photopolymerization initiator and polymerizable monomers, the resulting mixture was applied to the surface of a lens substrate, and ultraviolet light was applied to polymerize the coating film on the surface of the lens substrate.

For a photochromic curable composition, a mixture of 50 parts by mass of 2,2-bis(4-methacryloyloxypentaethoxyphenyl)propane, 10 parts by mass of polyethylene glycol diacrylate (average molecular weight of 532), 10 parts by mass of trimethylolpropane trimethacrylate, 10 parts by mass of polyester oligomer hexaacrylate (EB-1830 of Daicel UCB Co., Ltd.) and 10 parts by mass of glycidyl methacrylate as radically polymerizable monomers was used. 1 part by mass of the chromene compound obtained in Example 1 was added to and fully mixed with 90 parts by mass of this mixture of the radically polymerizable monomers, and 0.3 part by mass of CGI1800 {a mixture of 1-hydroxycyclohexylphenyl ketone and bis(2,6-dimethoxybenzoyl)-2,4,4-trimethyl-pentylphosphine oxide (weight ratio of 3:1)} as a photopolymerization initiator, 5 parts by mass of bis(1,2,2,6,6-pentamethyl-4-piperidyl)sebacate as a stabilizer, 3 parts by mass of ethylenebis(oxyethylene)bis[3-(5-tert-butyl-4-hydroxy-m-tolyl)propionate], 7 parts by mass of γ-methacryloyloxypropyl trimethoxysilane as a silane coupling agent and 3 parts by mass of N-methyldiethanolamine were added to and fully mixed with the above mixture to obtain a photochromic curable composition.

Subsequently, about 2 g of the photochromic curable composition obtained by the above method was applied to the surface of a lens substrate (CR39: allyl resin plastic lens; refractive index of 1.50) by using the 1H-DX2 spin coater of MIKASA Co., Ltd. This coated lens was irradiated with light from a metal halide lamp having an output of 120 mW/cm$^2$ in a nitrogen gas atmosphere for 3 minutes to cure the photochromic curable composition. Thus, an optical article (photochromic plastic lens) which was coated with a polymer film containing the cured chromene compound dispersed therein (thickness of polymer film: 40 μm) was manufactured.

The following photochromic properties of the obtained photochromic plastic lens were evaluated. The results obtained by using the chromene compound of Example 1 are shown in Table 3.

[1] Maximum absorption wavelength ($\lambda_{max}$): This is the maximum absorption wavelength after color development obtained by means of the spectrophotometer (MCPD3000 instantaneous multi-channel photodetector) of Otsuka Electronics Co., Ltd. and used as an index of color at the time of color development. The maximum absorption wavelength is connected with color at the time of color development.

[2] Color optical density ($A_0$): This is the difference between absorbance {ε(120)} after 120 seconds of exposure and ε(0) under no exposure at the above maximum absorption wavelength and used as an index of color optical density. It can be said that as this value becomes larger; the photochromic properties become better.

[3] Double peak characteristic ($A_Y/A_B$): This is the ratio of color optical density ($A_Y$:value of $\lambda_{max}$) at a yellow range (having a maximum absorption wavelength at 430 to 530 nm) and color optical density ($A_B$:value of $\lambda_{max}$) at a blue range (having a maximum absorption wavelength at 550 to 650 nm) and used as an index of double peak characteristic.

[4] Fading half period [τ½ (sec.)]: time required for the reduction of the absorbance at the above maximum absorption wavelength of a sample to ½ of {ε(120)–ε(0)} when exposure is stopped after 120 seconds of exposure and used as an index of fading speed. As this time becomes shorter, the fading speed becomes higher.

[5] Absorption end {λ₀}: After the photochromic plastic lens obtained under the above conditions is used as a sample and kept in the dark for one day, the ultraviolet light transmittance (T %) at 300 to 800 nm of the sample is measured with an ultraviolet visible spectrophotometer (UV-2550 of Shimadzu Corporation) at room temperature. A tangent line is drawn on the obtained ultraviolet light absorption curve to ensure that the transmittance (T %) of the ultraviolet light absorption curve passes a point of 50% so as to obtain an absorption wavelength at which the transmittance (T %) of the tangent line becomes 0 as the absorption end (absorption end of the ultraviolet light spectrum) and used as an index of initial coloration. For example, in an optical article such as a spectacle lens, as this value becomes smaller, the initial coloration becomes weaker and the transparency under no exposure becomes higher.

[6] Thermochromism {T₀}: The photochromic plastic lens obtained under the above conditions is used as a sample and its transmittance (T %) at 300 to 800 nm is measured with an ultraviolet visible spectrophotometer (UV-2550 of Shimadzu Corporation) at room temperature. This is a transmittance at a wavelength at which the transmittance at 430 to 650 nm becomes minimal and used as an index of initial coloration. As this value becomes larger, the initial coloration becomes weaker and the transparency under no exposure becomes higher.

[7] Residual rate ($A_{50}/A_0 \times 100$): The deterioration promotion test of the obtained photochromic plastic lens is carried out by using the X25 xenon weather meter of Suga Test Instruments Co., Ltd. for 50 hours. Thereafter, the above color optical density is evaluated before and after the test by measuring the color optical density ($A_0$) before the test and the color optical density ($A_{50}$) after the test to obtain the ratio ($A_{50}/A_0$) of these values as residual rate which is used as an index of color development durability. As the residual rate becomes higher, the color development durability becomes higher.

[8] color development sensitivity [$\epsilon(10)/\epsilon(120)$]: The photochromic plastic lens obtained under the above conditions is used as a sample, and the ratio of color optical density {$\epsilon(120)$} after 120 seconds of exposure to color optical density {$\epsilon(10)$} after 10 seconds of exposure is calculated and used as an index of color development sensitivity. As this value becomes larger, the photochromic plastic lens develops a dark color with a shorter time of exposure.

Photochromic plastic lenses were obtained and their photochromic properties were evaluated in the same manner as described above except that the chromene compounds obtained in Examples 2 to 15 were used. The results are shown in Table 3. In Table 3, compound Nos. 1 to 15 are chromene compounds obtained in Examples Nos. 1 to 15, respectively. For example, the chromene compound obtained in Example 1 is expressed as Compound No. 1.

TABLE 3

| Example No. | Compound No. | $\lambda_{max}$ (nm) | Color optical density $A_0$ | Double peak characteristic $A_Y/A_B$ | Fading half period $\tau^{1/2}$ (sec) | Initial coloration (absorption end) (nm) | Initial coloration (thermochromism) (%) | Residual rate ($A_{50}/A_0$) × 100 | Color development sensitivity $\epsilon(10)/\epsilon(120)$ |
|---|---|---|---|---|---|---|---|---|---|
| 16 | 1 | 457 | 0.60 | 1.21 | 65 | 405 | 89 | 92 | 0.27 |
|  |  | 575 | 0.50 |  | 65 |  | 90 | 92 |  |
| 17 | 2 | 459 | 0.65 | 1.30 | 66 | 413 | 88 | 91 | 0.32 |
|  |  | 573 | 0.50 |  | 66 |  | 89 | 91 |  |
| 18 | 3 | 473 | 0.74 | 1.45 | 67 | 414 | 87 | 87 | 0.32 |
|  |  | 573 | 0.51 |  | 67 |  | 88 | 87 |  |
| 19 | 4 | 477 | 0.89 | 1.75 | 75 | 418 | 85 | 85 | 0.35 |
|  |  | 578 | 0.51 |  | 75 |  | 87 | 85 |  |
| 20 | 5 | 443 | 0.68 | 1.00 | 50 | 411 | 90 | 91 | 0.31 |
|  |  | 580 | 0.68 |  | 51 |  | 90 | 91 |  |
| 21 | 6 | 453 | 0.51 | 1.03 | 55 | 403 | 90 | 90 | 0.26 |
|  |  | 576 | 0.50 |  | 56 |  | 90 | 90 |  |
| 22 | 7 | 455 | 0.56 | 1.10 | 56 | 412 | 90 | 91 | 0.30 |
|  |  | 574 | 0.51 |  | 57 |  | 90 | 91 |  |
| 23 | 8 | 458 | 0.53 | 1.03 | 57 | 408 | 90 | 90 | 0.28 |
|  |  | 579 | 0.51 |  | 57 |  | 90 | 90 |  |
| 24 | 9 | 460 | 0.66 | 1.30 | 66 | 408 | 89 | 92 | 0.29 |
|  |  | 577 | 0.51 |  | 66 |  | 89 | 92 |  |
| 25 | 10 | 453 | 0.72 | 1.20 | 120 | 405 | 82 | 82 | 0.25 |
|  |  | 576 | 0.60 |  | 120 |  | 82 | 82 |  |
| 26 | 11 | 455 | 0.50 | 1.18 | 70 | 405 | 84 | 80 | 0.28 |
|  |  | 576 | 0.42 |  | 70 |  | 84 | 80 |  |
| 27 | 12 | 460 | 0.59 | 1.39 | 68 | 406 | 86 | 89 | 0.28 |
|  |  | 565 | 0.42 |  | 68 |  | 87 | 88 |  |
| 28 | 13 | 457 | 0.60 | 1.00 | 76 | 403 | 87 | 85 | 0.26 |
|  |  | 575 | 0.60 |  | 76 |  | 88 | 85 |  |
| 29 | 14 | 460 | 0.54 | 1.00 | 67 | 420 | 80 | 81 | 0.36 |
|  |  | 573 | 0.54 |  | 67 |  | 80 | 81 |  |
| 30 | 15 | 473 | 0.47 | 1.00 | 60 | 405 | 88 | 80 | 0.27 |
|  |  | 578 | 0.47 |  | 60 |  | 89 | 80 |  |

Comparative Examples 1 to 6

For comparison, photochromic plastic lenses were obtained and their characteristic properties were evaluated in the same manner as in Example 16 except that compounds represented by the following formulas (A) to (F) were used. The results are shown in Table 4.

TABLE 4
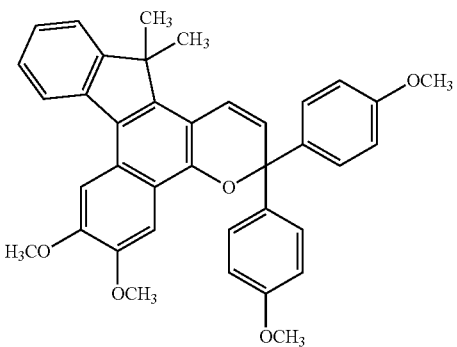 [SMILES: COc1ccc(C2(c3ccc(OC)cc3)C=Cc3c4c(c5cc(OC)c(OC)cc5c3O2)-c2ccccc2C4(C)C)cc1] (A)
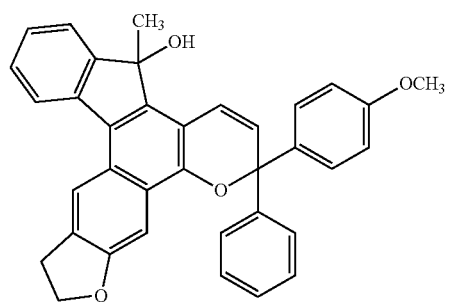 [SMILES: COc1ccc(C2(c3ccccc3)C=Cc3c4c(c5cc6c(cc5c3O2)OCC6)-c2ccccc2C4(C)O)cc1] (B)
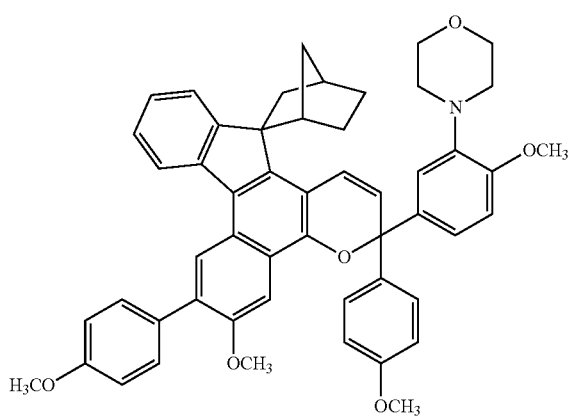 [SMILES: COc1ccc(-c2cc3c4c(c5c(c3cc2OC)OC(c2ccc(OC)cc2)(c2ccc(OC)c(N3CCOCC3)c2)C=C5)C2(CC3CCC2C3)c2ccccc2-4)cc1] (C)
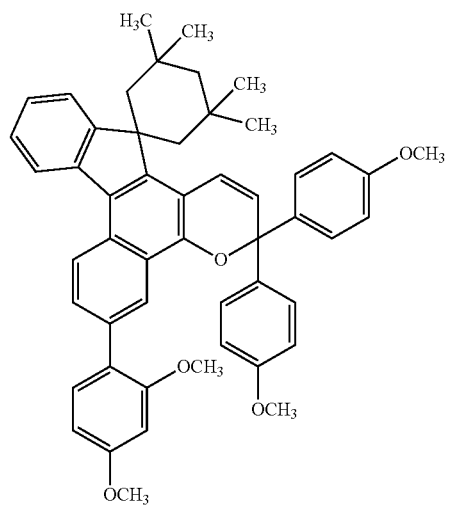 [SMILES: COc1ccc(C2(c3ccc(OC)cc3)C=Cc3c4c(c5ccc(-c6ccc(OC)cc6OC)cc5c3O2)-c2ccccc2C42CC(C)(C)CC(C)(C)C2)cc1] (D)

TABLE 4-continued

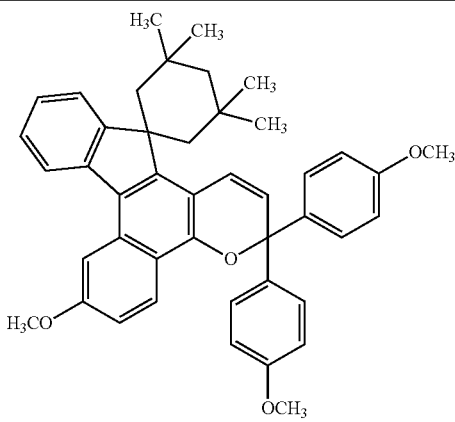

(E)

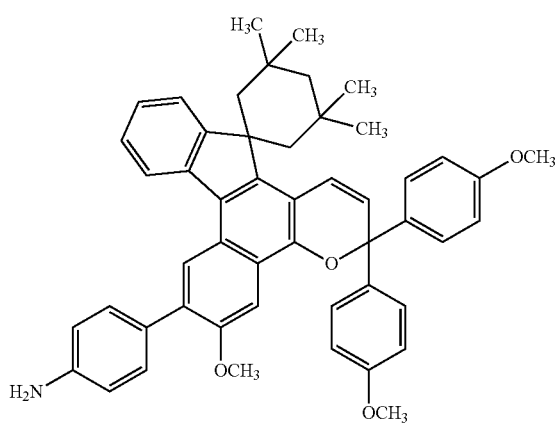 [SMILES: COc1ccc(C2(c3ccc(OC)cc3)C=Cc3c4c(c5cc(-c6ccc(N)cc6)c(OC)cc5c3O2)-c2ccccc2C42CC(C)(C)CC(C)(C)C2)cc1]

(F)

| Comparative Example No. | Compound No. | $\lambda_{max}$ (nm) | Color optical density $A_0$ | Double peak characteristic $A_Y/A_B$ | Fading half period $\tau 1/2$ (sec) | initial coloration (absorption end) (nm) | Initial coloration (thermo-chromism) (%) | Residual rate $(A_{50}/A_0) \times 100$ | Color development sensitivity $\epsilon(10)/\epsilon(120)$ |
|---|---|---|---|---|---|---|---|---|---|
| 1 | A | 457 | 0.69 | 1.56 | 195 | 397 | 67 | 76 | 0.20 |
|   |   | 574 | 0.45 |      | 196 |     | 75 | 77 |      |
| 2 | B | 455 | 0.30 | 0.94 | 83  | 410 | 77 | 35 | 0.28 |
|   |   | 576 | 0.32 |      | 83  |     | 78 | 35 |      |
| 3 | C | 458 | 0.44 | 1.20 | 68  | 422 | 84 | 85 | 0.36 |
|   |   | 568 | 0.37 |      | 68  |     | 86 | 84 |      |
| 4 | D | 433 | 0.50 | 0.80 | 40  | 415 | 90 | 87 | 0.33 |
|   |   | 582 | 0.63 |      | 40  |     | 90 | 87 |      |
| 5 | E | 456 | 0.39 | 0.70 | 92  | 385 | 89 | 89 | 0.20 |
|   |   | 575 | 0.55 |      | 93  |     | 89 | 89 |      |
| 6 | F | 463 | 0.52 | 1.30 | 78  | 428 | 83 | 80 | 0.36 |
|   |   | 580 | 0.40 |      | 78  |     | 84 | 80 |      |

It is understood that Examples 16 to 30 (compounds 1 to 15) which were obtained from the chromene compounds of the present invention exhibit high color optical density, high fading speed, little initial coloration, high repeat durability and high color development sensitivity as well as high double peak characteristic.

The chromene compound of the present invention having high double peak characteristic ($A_Y/A_B$) is preferred because a blue compound having excellent durability can be used for delicate color control. For example, $A_Y/A_B$ is preferably not less than 1.00, more preferably not less than 1.10, much more preferably not less than 1.20, particularly preferably not less than 1.30.

The fading half period $\tau\frac{1}{2}$ is preferably 50 or more to less than 130 seconds, more preferably 50 or more to less than 100 seconds, particular preferably 50 or more to less than 80 seconds.

The transmittance by thermochromism is preferably not less than 80%, more preferably not less than 83%, particularly preferably not less than 85%.

The absorption end is existent at preferably 400 to 420 nm, more preferably 405 to 420 nm, particularly preferably 405 to 415 nm from the viewpoints of initial coloration and color development sensitivity.

Although Comparative Example 1 (compound A) has high double peak characteristic, it has very low fading speed, low repeat durability and low color development sensitivity. In contrast to this, it is understood that Example 27 (compound 10) of the present invention has high fading speed and high repeat durability while retaining double peak characteristic.

Comparative Example 2 (compound B) has low double peak characteristic and also low repeat durability. In contrast to this, it is understood that Example 26 (compound 11) of the present invention has high double characteristic and high repeat durability.

Although Comparative Example 3 (compound C) has high double peak characteristic and excellent repeat durability, it has a problem such as large initial coloration due to the absorption end (it is colored yellow as its absorption end is existent at a visible range). In contrast to this, it is seen that Example 27 (compound 12) of the present invention has little initial coloration while retaining double peak characteristic and repeat durability.

Comparative Example 4 (compound D) has an aryl group at the 6-position but no substituent having a Hammett constant $\sigma_p$ of not more than −0.1 at the 7-position. In this case, high double peak characteristic cannot be obtained.

Although Comparative Example 5 (compound E) has a substituent with a Hammett constant $\sigma_p$ of not more than −0.1 at the 7-position, it does not have an aryl group or a heteroaryl group at the 6-position. In this case, high double peak characteristic cannot be obtained.

Although Comparative Example 6 (Compound F) has high double peak characteristic and excellent repeat durability, it has a problem such as large initial coloration due to the absorption end (it is colored yellow as its absorption end is existent at a visible range). In contrast to this, it is seen that Example 92 (compound 33) of the present invention which will be described hereinafter has little initial coloration due to the absorption end while retaining double peak characteristic and repeat durability.

Examples 31 to 89

Chromene compounds shown in Table 5 were synthesized in the same manner as in Example 1. When the structures of the obtained chromene compounds were analyzed in the same manner as in Example 1, it was confirmed that they were compounds represented by the structural formulas shown in Table 5. Table 6 shows the elemental analysis values and $^1$H-NMR spectral values of the chromene compounds obtained in Examples. In Table 6, compound Nos. 31 to 89 are chromene compounds obtained in Examples 31 to 89, respectively.

TABLE 5

| | Raw materials | |
|---|---|---|
| Example No. | Naphthol derivative | Propargyl alcohol derivative |
| 31 | [structure] | [structure] |

TABLE 5-continued
| 32 | 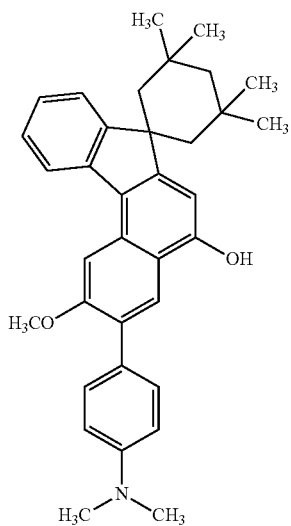 [SMILES: COc1cc2c3c(cc(O)c2cc1-c1ccc(N(C)C)cc1)C1(CC(C)(C)CC(C)(C)C1)c1ccccc1-3] | 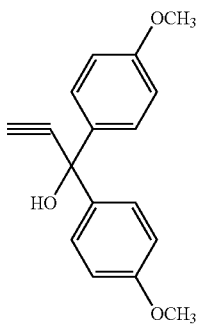 |
| --- | --- | --- |
| 33 | 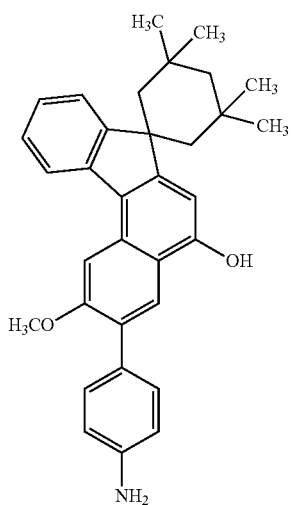 [SMILES: COc1cc2c3c(cc(O)c2cc1-c1ccc(N)cc1)C1(CC(C)(C)CC(C)(C)C1)c1ccccc1-3] | 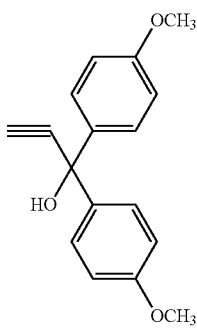 |
| 34 | 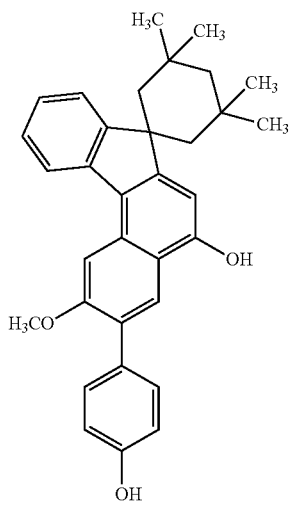 [SMILES: COc1cc2c3c(cc(O)c2cc1-c1ccc(O)cc1)C1(CC(C)(C)CC(C)(C)C1)c1ccccc1-3] | 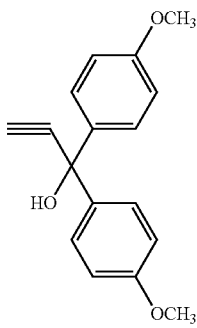 |

TABLE 5-continued
| 35 | 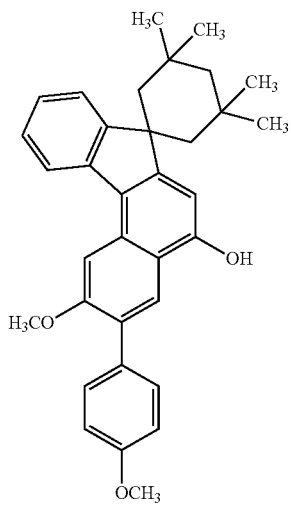 [SMILES: COc1ccc(-c2cc3c(O)cc4c(c3cc2OC)-c2ccccc2C42CC(C)(C)CC(C)(C)C2)cc1] | 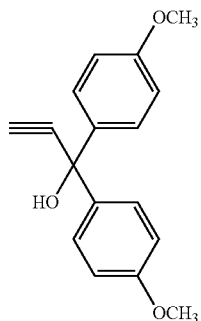 |
|---|---|---|
| 36 | 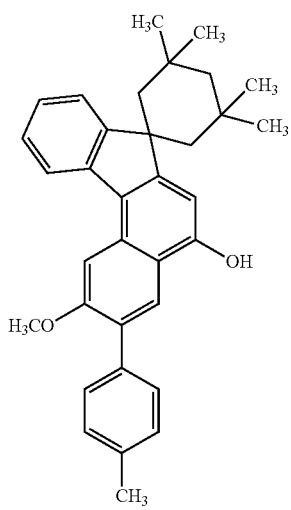 [SMILES: COc1cc2c3c(cc(O)c2cc1-c1ccc(C)cc1)C1(CC(C)(C)CC(C)(C)C1)c1ccccc1-3] | 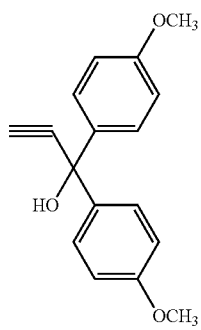 [SMILES: C#CC(O)(c1ccc(OC)cc1)c1ccc(OC)cc1] |
|---|---|---|
| 37 | 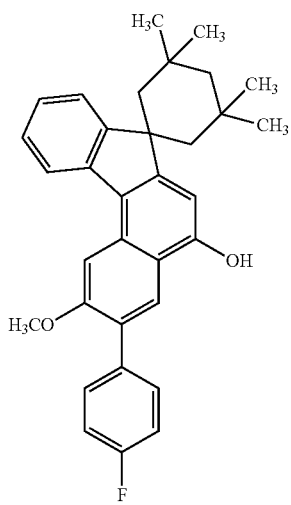 [SMILES: COc1cc2c3c(cc(O)c2cc1-c1ccc(F)cc1)C1(CC(C)(C)CC(C)(C)C1)c1ccccc1-3] | 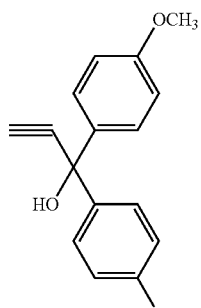 |
|---|---|---|

TABLE 5-continued
| 38 | 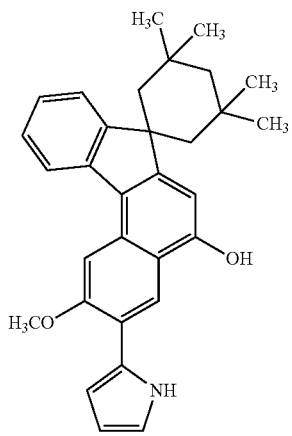 [SMILES: COc1cc2c3c(cc(O)c2cc1-c1ccc[nH]1)C1(CC(C)(C)CC(C)(C)C1)c1ccccc1-3] | 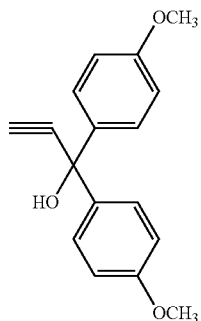 |
| --- | --- | --- |
| 39 | 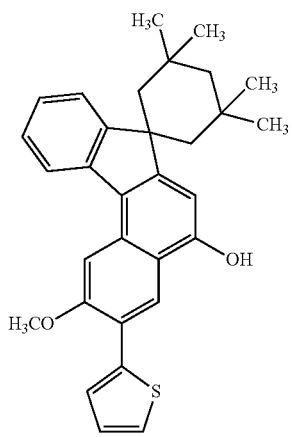 [SMILES: COc1cc2c3c(cc(O)c2cc1-c1cccs1)C1(CC(C)(C)CC(C)(C)C1)c1ccccc1-3] | 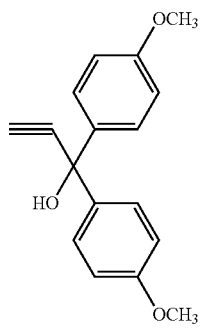 [SMILES: C#CC(O)(c1ccc(OC)cc1)c1ccc(OC)cc1] |
| 40 | 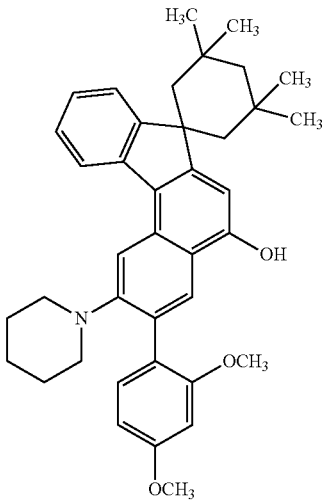 [SMILES: COc1ccc(-c2cc3c(O)cc4c(c3cc2N2CCCCC2)-c2ccccc2C42CC(C)(C)CC(C)(C)C2)c(OC)c1] | 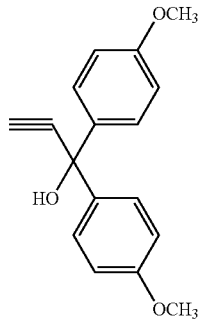 [SMILES: C#CC(O)(c1ccc(OC)cc1)c1ccc(OC)cc1] |

TABLE 5-continued
| 41 | 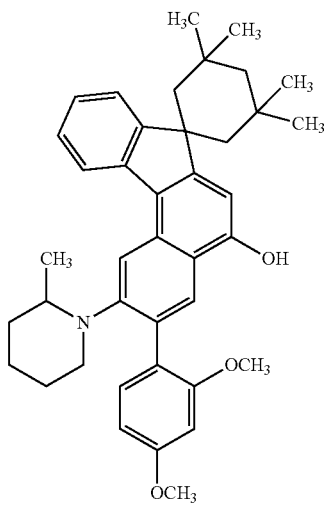 [SMILES: COc1ccc(-c2cc3c(O)cc4c(c3cc2N2CCCCC2C)-c2ccccc2C42CC(C)(C)CC(C)(C)C2)c(OC)c1] | 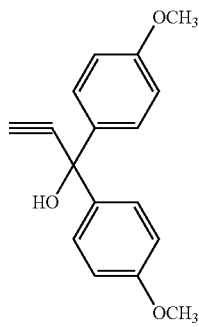 [SMILES: C#CC(O)(c1ccc(OC)cc1)c1ccc(OC)cc1] |
| 42 | 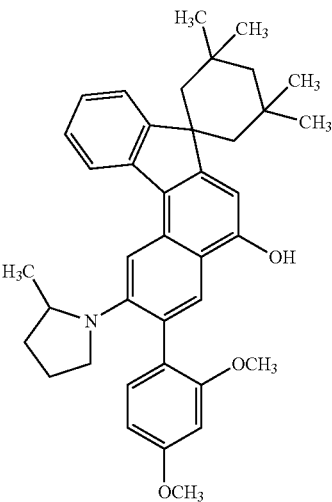 [SMILES: COc1ccc(-c2cc3c(O)cc4c(c3cc2N2CCCC2C)-c2ccccc2C42CC(C)(C)CC(C)(C)C2)c(OC)c1] | 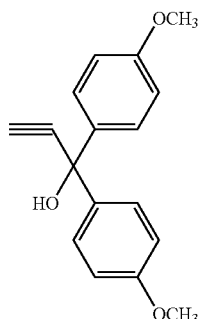 |
| 43 | 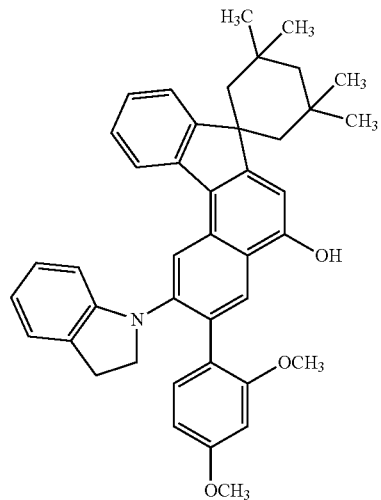 [SMILES: COc1ccc(-c2cc3c(O)cc4c(c3cc2N2CCc3ccccc32)-c2ccccc2C42CC(C)(C)CC(C)(C)C2)c(OC)c1] | 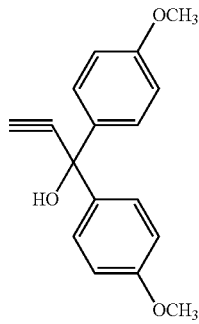 [SMILES: C#CC(O)(c1ccc(OC)cc1)c1ccc(OC)cc1] |

TABLE 5-continued
| 44 | 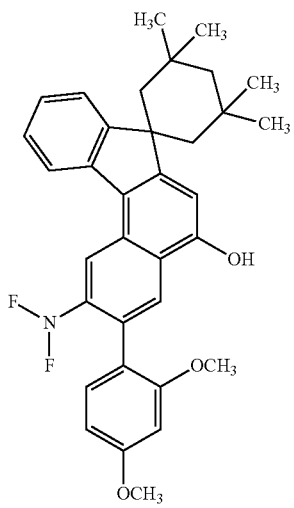 [SMILES: COc1ccc(-c2cc3c(O)cc4c(c3cc2N(F)F)-c2ccccc2C42CC(C)(C)CC(C)(C)C2)c(OC)c1] | 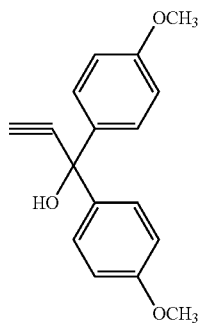 [SMILES: C#CC(O)(c1ccc(OC)cc1)c1ccc(OC)cc1] |
| --- | --- | --- |
| 45 | 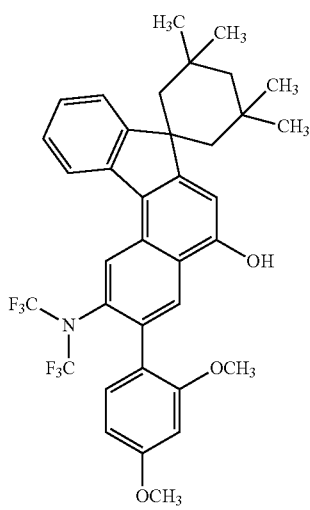 [SMILES: COc1ccc(-c2cc3c(O)cc4c(c3cc2N(C(F)(F)F)C(F)(F)F)-c2ccccc2C42CC(C)(C)CC(C)(C)C2)c(OC)c1] | 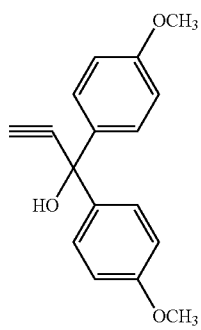 [SMILES: C#CC(O)(c1ccc(OC)cc1)c1ccc(OC)cc1] |
| 46 | 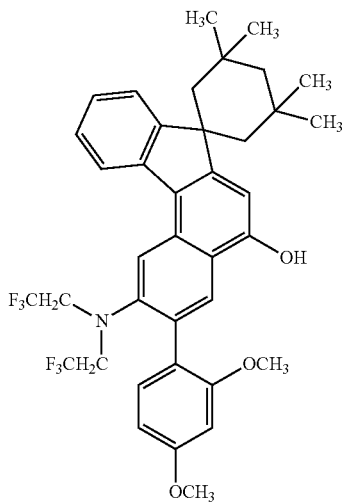 | 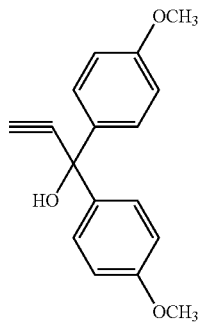 [SMILES: C#CC(O)(c1ccc(OC)cc1)c1ccc(OC)cc1] |

TABLE 5-continued
| 47 | 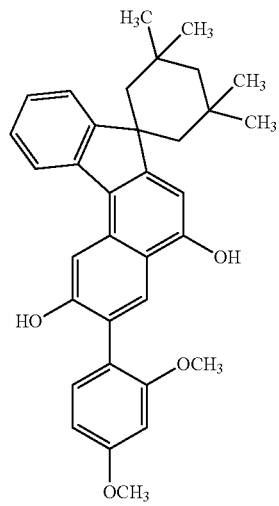 [SMILES: COc1ccc(-c2cc3c(O)cc4c(c3cc2O)-c2ccccc2C42CC(C)(C)CC(C)(C)C2)c(OC)c1] | 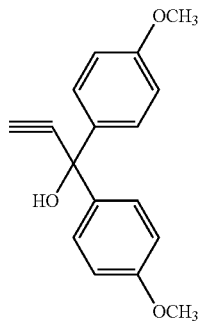 [SMILES: C#CC(O)(c1ccc(OC)cc1)c1ccc(OC)cc1] |
| 48 | 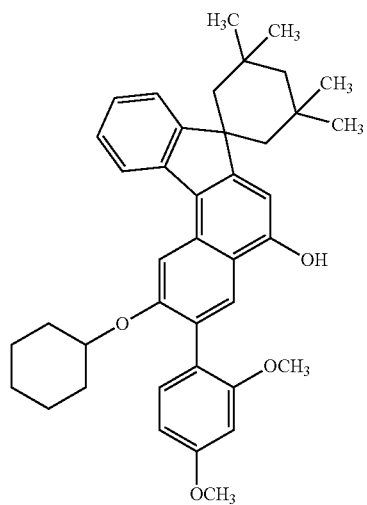 [SMILES: COc1ccc(-c2cc3c(O)cc4c(c3cc2OC2CCCCC2)-c2ccccc2C42CC(C)(C)CC(C)(C)C2)c(OC)c1] | 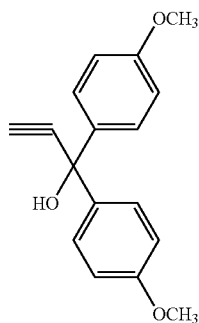 |
| 49 | 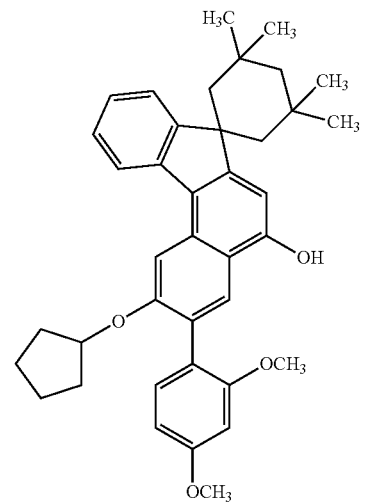 [SMILES: COc1ccc(-c2cc3c(O)cc4c(c3cc2OC2CCCC2)-c2ccccc2C42CC(C)(C)CC(C)(C)C2)c(OC)c1] | 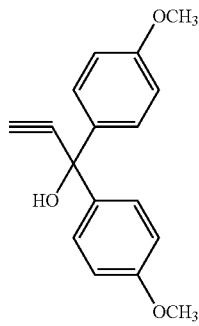 [SMILES: C#CC(O)(c1ccc(OC)cc1)c1ccc(OC)cc1] |

TABLE 5-continued
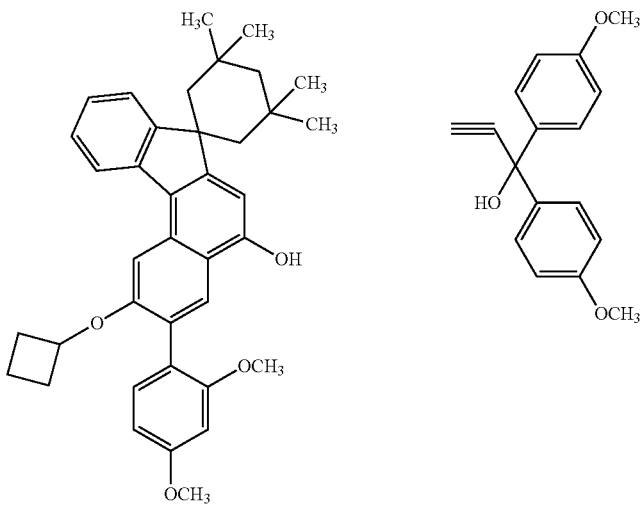
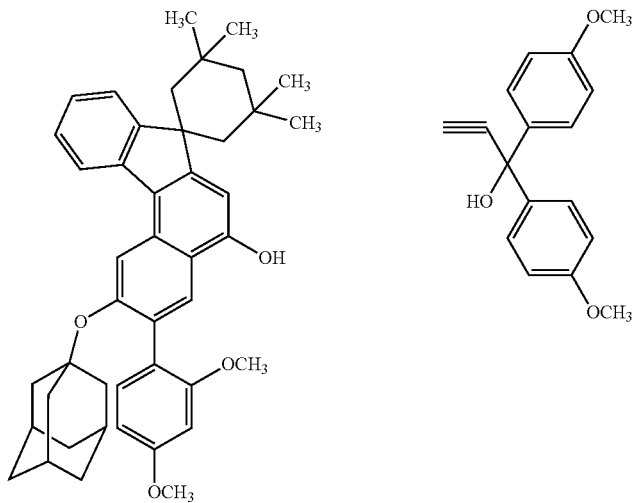
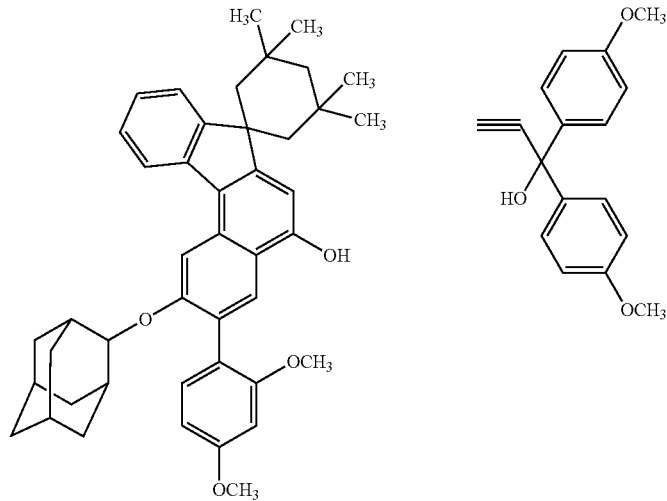

TABLE 5-continued
| 53 | 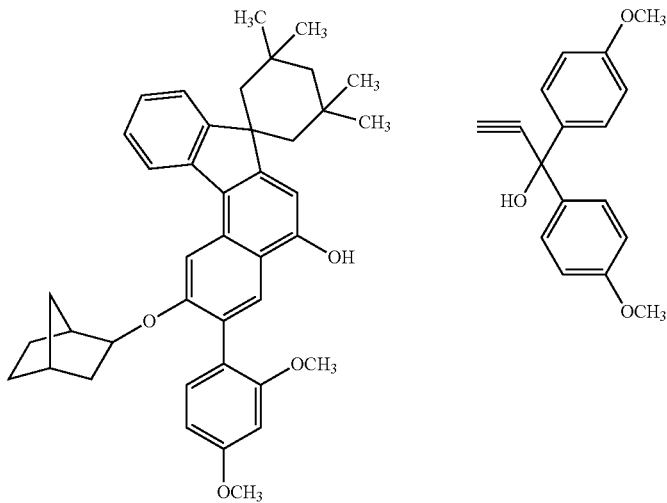 |
| 54 | 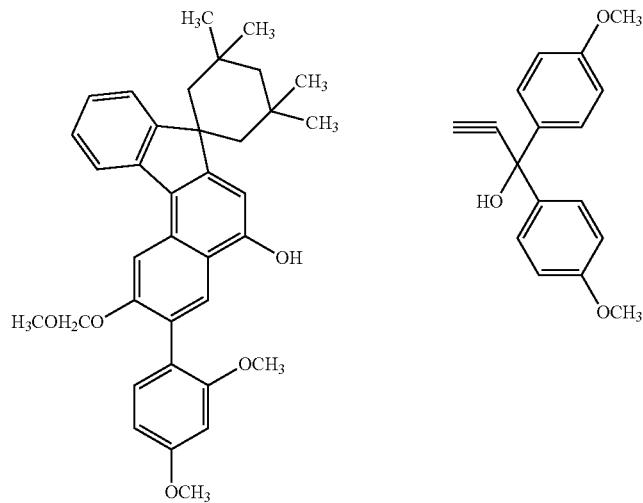 |
| 55 | 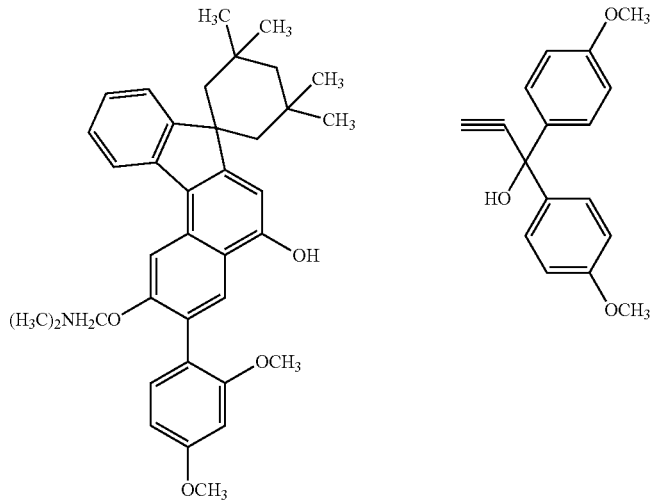 |

TABLE 5-continued
| 56 | 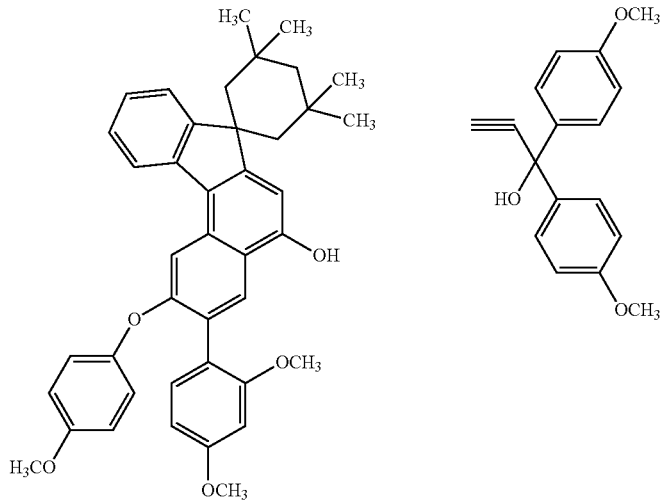 |
| 57 | 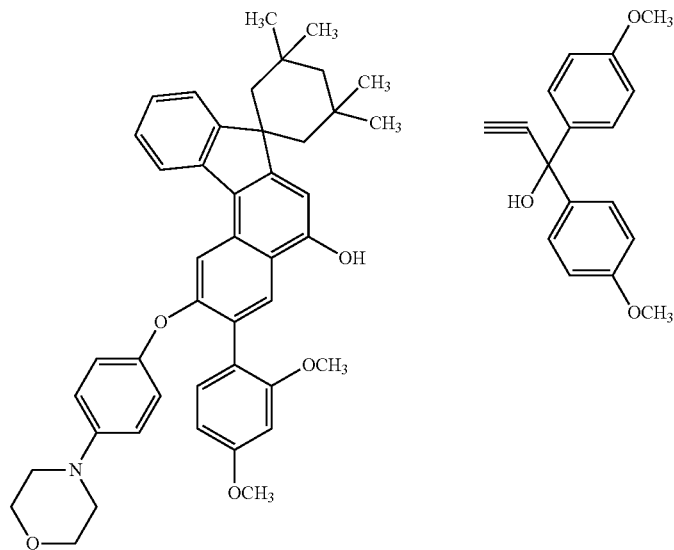 |
| 58 | 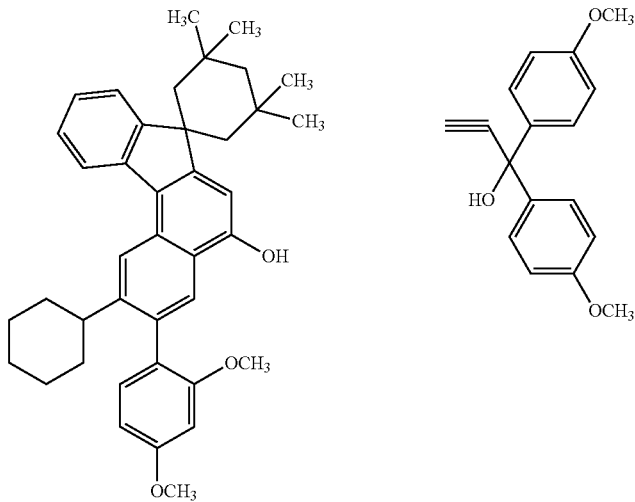 |

TABLE 5-continued
| | | |
|---|---|---|
| 59 | 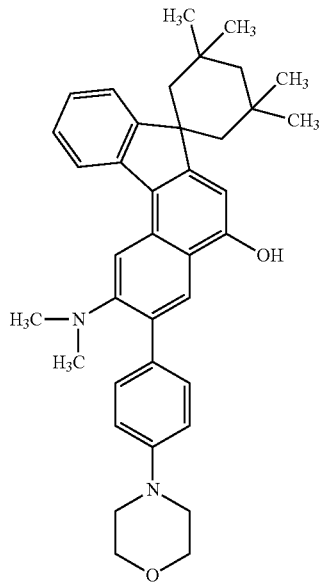 | 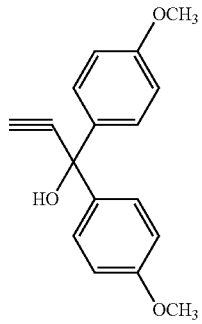 |
| 60 | 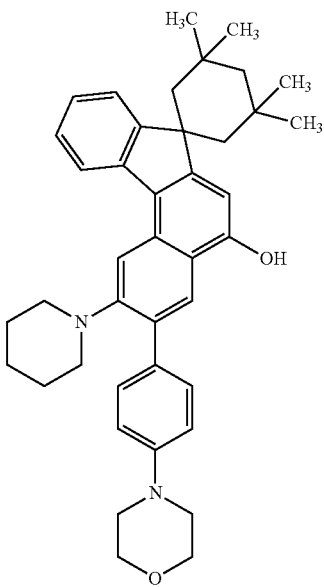 [SMILES: CC1(C)CC(C)(C)CC2(C1)c1ccccc1-c1c2cc(O)c2cc(-c3ccc(N4CCOCC4)cc3)c(N3CCCCC3)cc12] | |

TABLE 5-continued
61 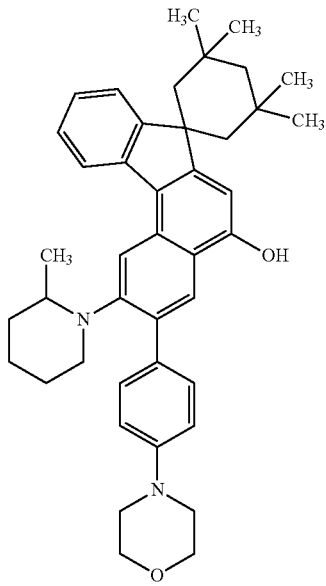 [SMILES: CC1CCCCN1c1cc2c3c(cc(O)c2cc1-c1ccc(N2CCOCC2)cc1)C1(CC(C)(C)CC(C)(C)C1)c1ccccc1-3] 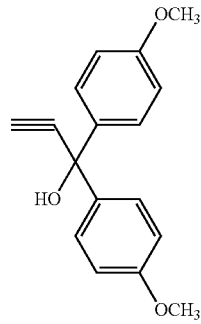
62 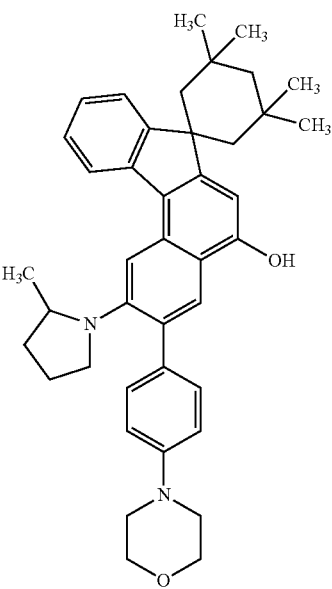 [SMILES: CC1CCCN1c1cc2c3c(cc(O)c2cc1-c1ccc(N2CCOCC2)cc1)C1(CC(C)(C)CC(C)(C)C1)c1ccccc1-3] 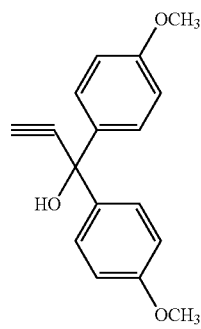

TABLE 5-continued
| 63 | 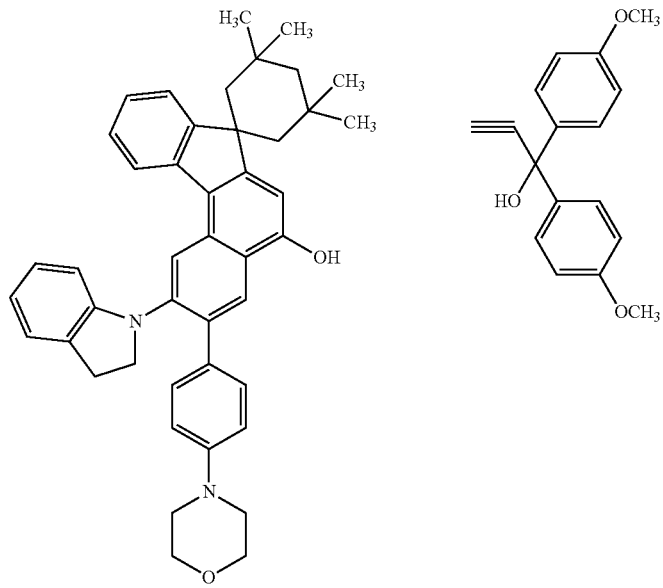 |
| 64 | 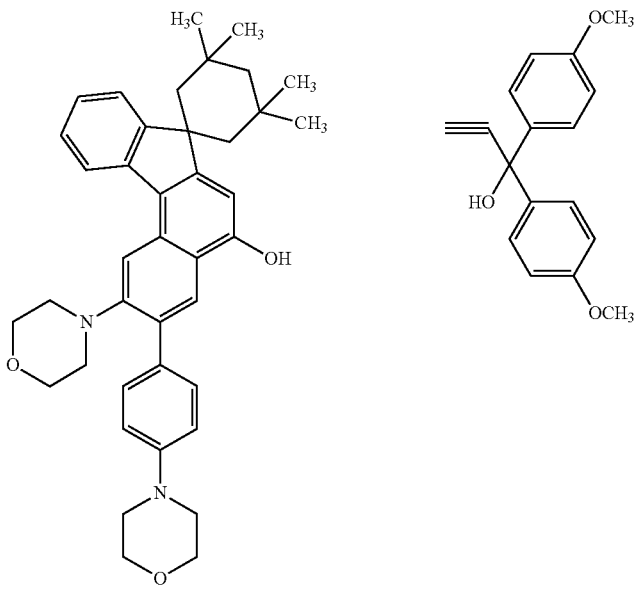 |

TABLE 5-continued
| 65 | 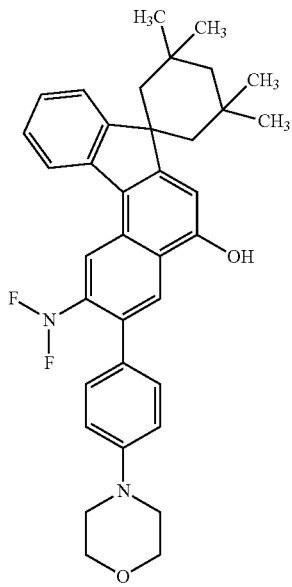 [SMILES: CC1(C)CC(C)(C)CC2(C1)c1ccccc1-c1c2cc(O)c2cc(-c3ccc(N4CCOCC4)cc3)c(N(F)F)cc12] | 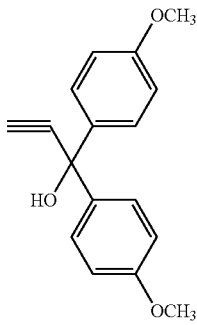 |
| 66 | 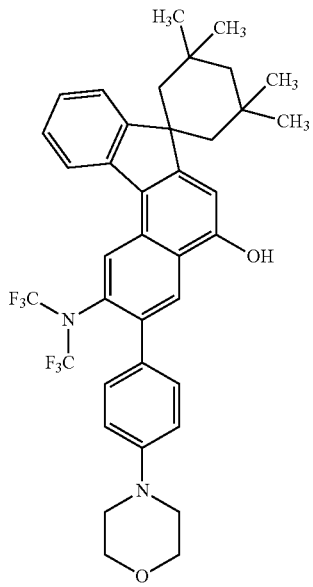 [SMILES: CC1(C)CC(C)(C)CC2(C1)c1ccccc1-c1c2cc(O)c2cc(-c3ccc(N4CCOCC4)cc3)c(N(C(F)(F)F)C(F)(F)F)cc12] | 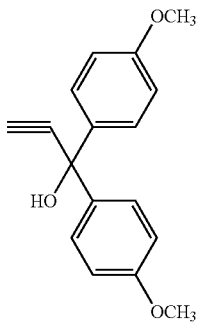 |

TABLE 5-continued
| 67 | 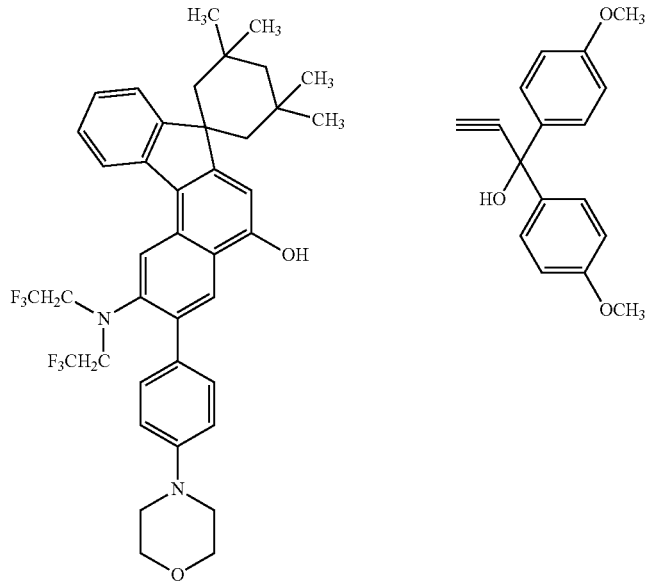 |
| 68 | 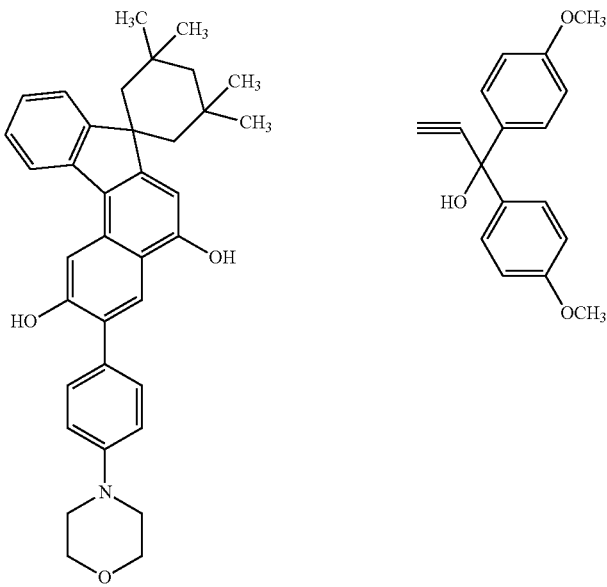 |

TABLE 5-continued
| 69 | 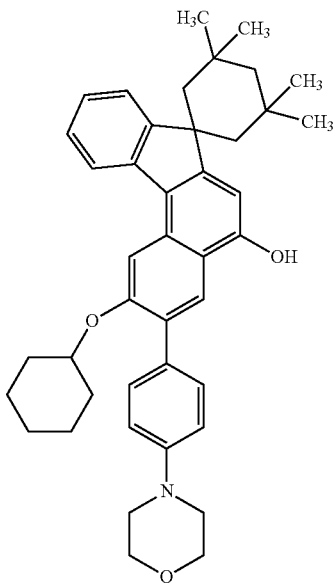 [SMILES: CC1(C)CC(C)(C)CC2(C1)c1ccccc1-c1c2cc(O)c2cc(-c3ccc(N4CCOCC4)cc3)c(OC3CCCCC3)cc12] | 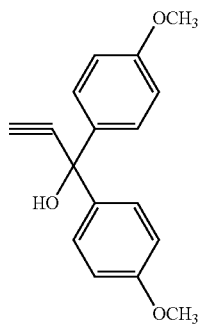 [SMILES: C#CC(O)(c1ccc(OC)cc1)c1ccc(OC)cc1] |
| 70 | 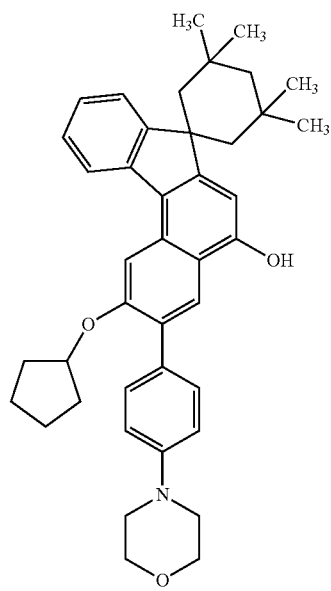 [SMILES: CC1(C)CC(C)(C)CC2(C1)c1ccccc1-c1c2cc(O)c2cc(-c3ccc(N4CCOCC4)cc3)c(OC3CCCC3)cc12] | |

TABLE 5-continued
71 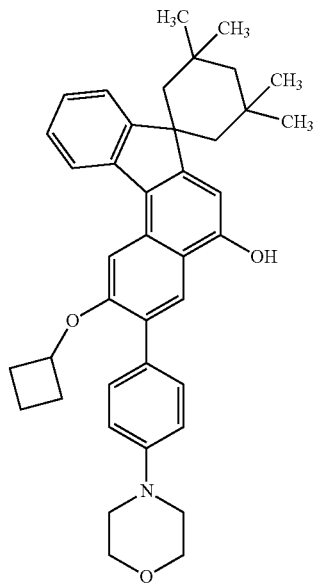 [SMILES: CC1(C)CC(C)(C)CC2(C1)c1ccccc1-c1c2cc(O)c2cc(-c3ccc(N4CCOCC4)cc3)c(OC3CCC3)cc12] 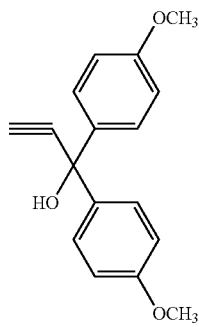 [SMILES: C#CC(O)(c1ccc(OC)cc1)c1ccc(OC)cc1]
72 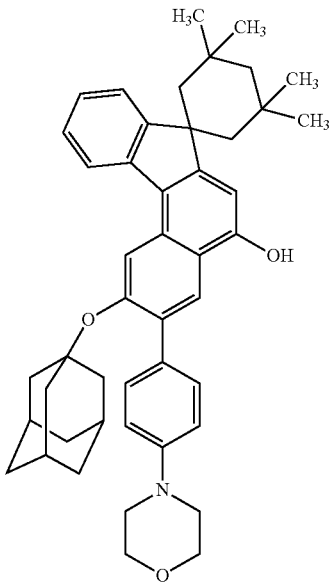 [SMILES: CC1(C)CC(C)(C)CC2(C1)c1ccccc1-c1c2cc(O)c2cc(-c3ccc(N4CCOCC4)cc3)c(OC34CC5CC(CC(C5)C3)C4)cc12] 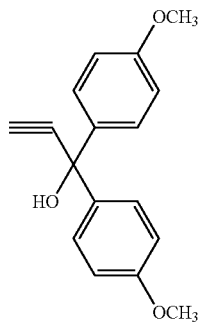 [SMILES: C#CC(O)(c1ccc(OC)cc1)c1ccc(OC)cc1]

TABLE 5-continued
| 73 | 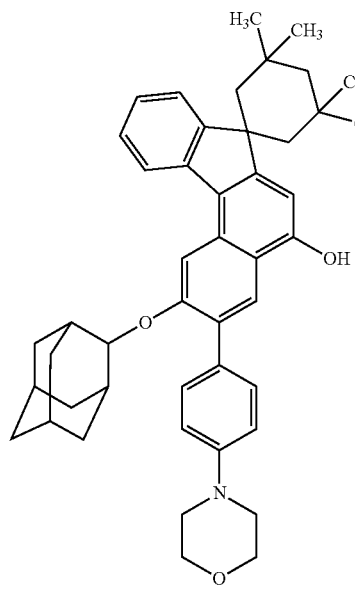 | 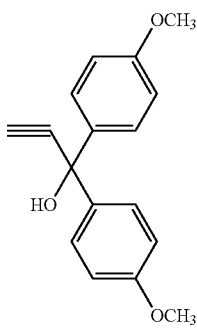 [SMILES: C#CC(O)(c1ccc(OC)cc1)c1ccc(OC)cc1] |
| 74 | 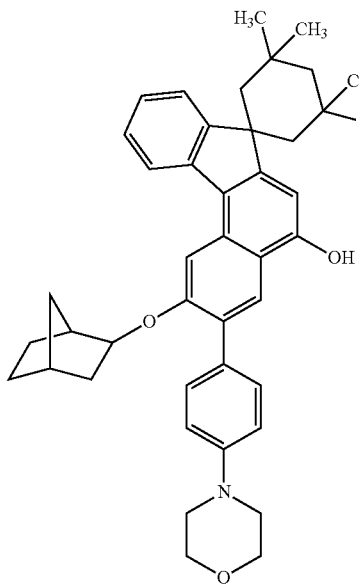 | 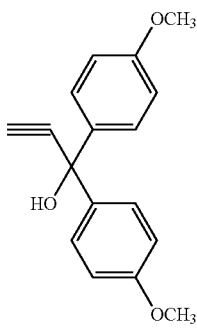 [SMILES: C#CC(O)(c1ccc(OC)cc1)c1ccc(OC)cc1] |

TABLE 5-continued
| 75 | 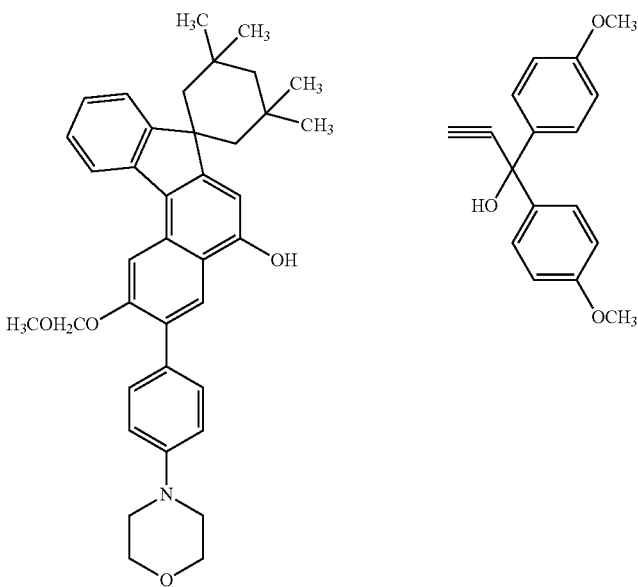 | 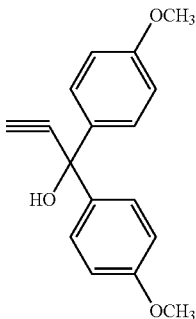 |
| 76 | 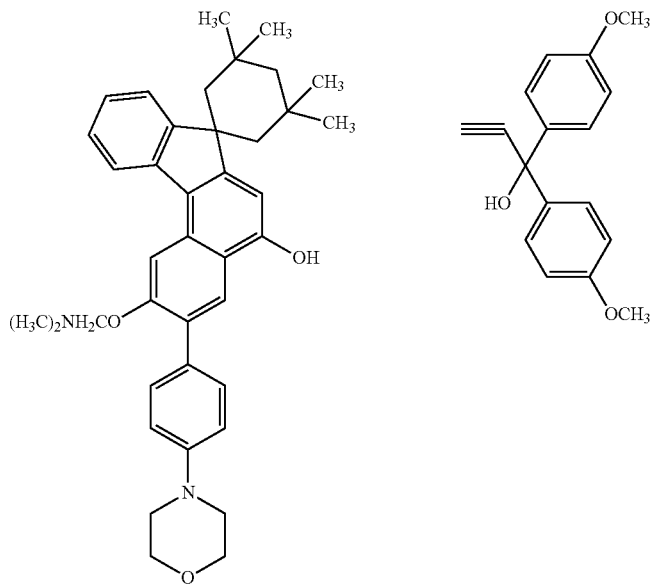 | 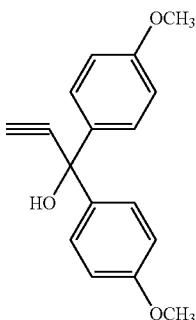 |

TABLE 5-continued
| 77 | 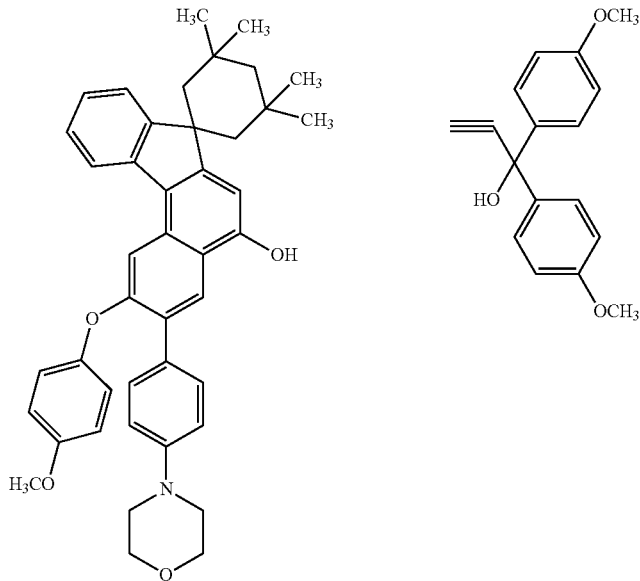 | 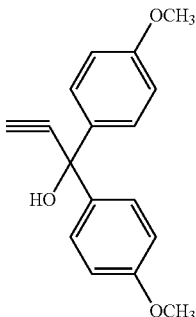 |
| 78 | 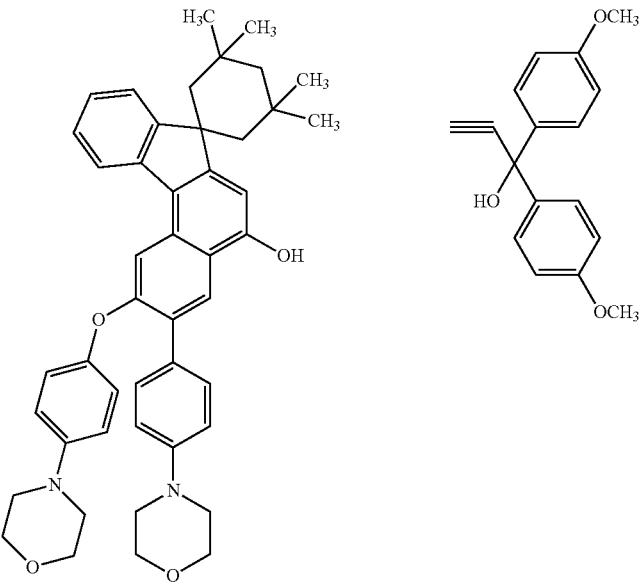 | 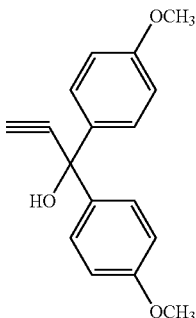 |

TABLE 5-continued
| 79 | 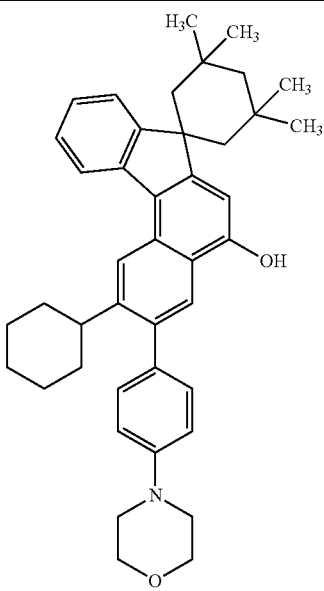 | 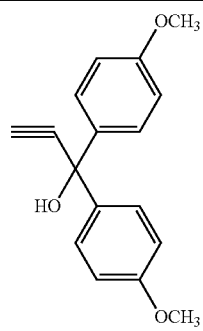 |
| 80 | 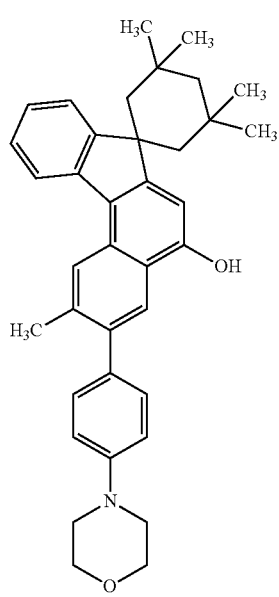 [SMILES: Cc1cc2c3c(cc(O)c2cc1-c1ccc(N2CCOCC2)cc1)C1(CC(C)(C)CC(C)(C)C1)c1ccccc1-3] | 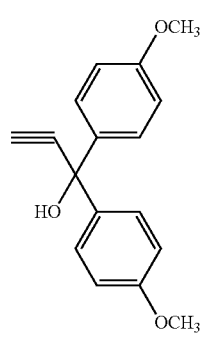 [SMILES: C#CC(O)(c1ccc(OC)cc1)c1ccc(OC)cc1] |
| 81 | 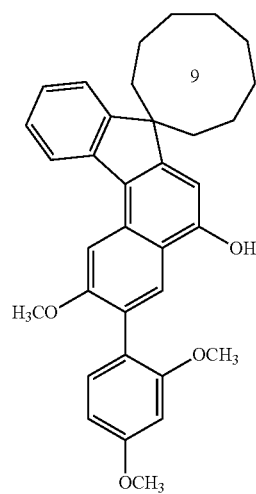 [SMILES: COc1ccc(-c2cc3c(O)cc4c(c3cc2OC)-c2ccccc2C42CCCCCCCC2)c(OC)c1] | 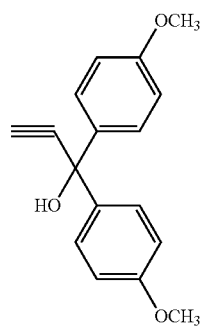 [SMILES: C#CC(O)(c1ccc(OC)cc1)c1ccc(OC)cc1] |

TABLE 5-continued
82 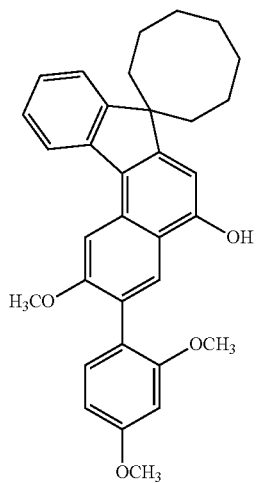 [SMILES: COc1ccc(-c2cc3c(O)cc4c(c3cc2OC)-c2ccccc2C42CCCCCCC2)c(OC)c1] 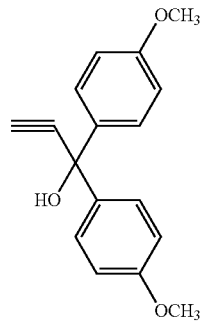
83 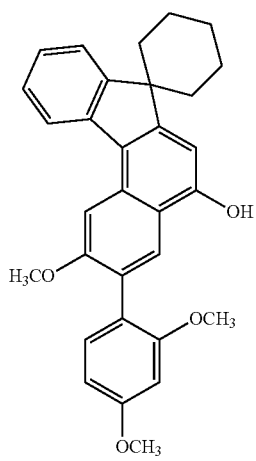 [SMILES: COc1ccc(-c2cc3c(O)cc4c(c3cc2OC)-c2ccccc2C42CCCCC2)c(OC)c1] 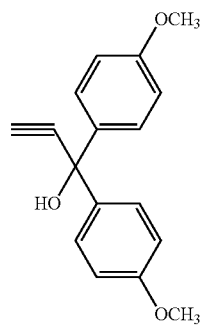 [SMILES: C#CC(O)(c1ccc(OC)cc1)c1ccc(OC)cc1]
84 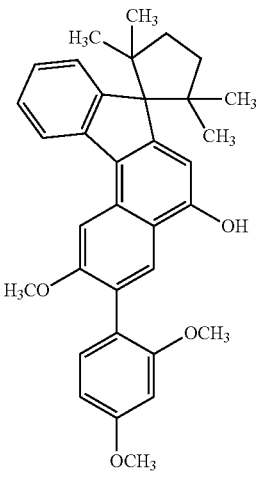 [SMILES: COc1ccc(-c2cc3c(O)cc4c(c3cc2OC)-c2ccccc2C42C(C)(C)CCC2(C)C)c(OC)c1] 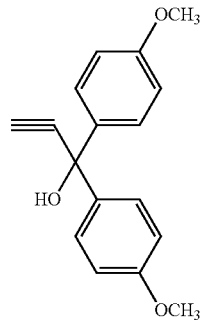 [SMILES: C#CC(O)(c1ccc(OC)cc1)c1ccc(OC)cc1]

TABLE 5-continued
| 85 | 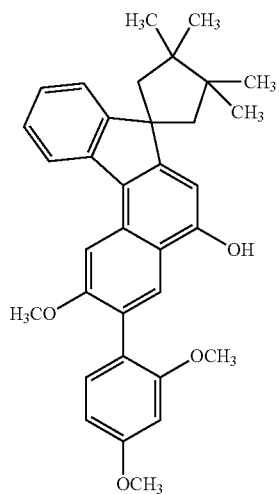 [SMILES: COc1ccc(-c2cc3c(O)cc4c(c3cc2OC)-c2ccccc2C42CC(C)(C)C(C)(C)C2)c(OC)c1] | 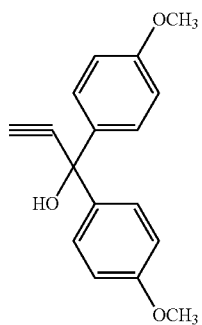 [SMILES: C#CC(O)(c1ccc(OC)cc1)c1ccc(OC)cc1] |
| --- | --- | --- |
| 86 | 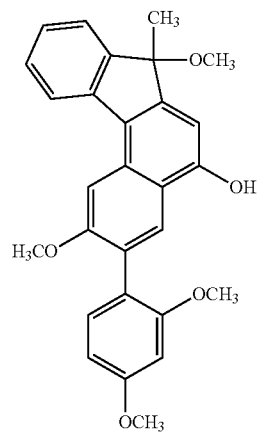 [SMILES: COc1ccc(-c2cc3c(O)cc4c(c3cc2OC)-c2ccccc2C4(C)OC)c(OC)c1] | 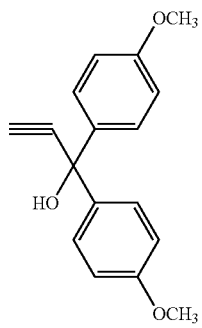 |
| 87 | 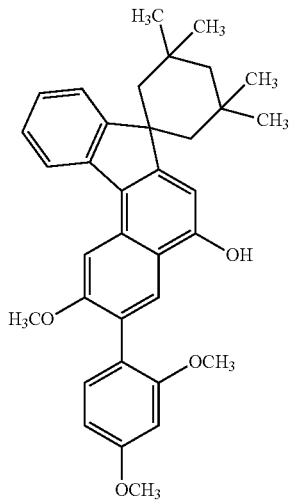 [SMILES: COc1ccc(-c2cc3c(O)cc4c(c3cc2OC)-c2ccccc2C42CC(C)(C)CC(C)(C)C2)c(OC)c1] | 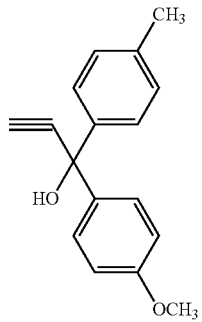 [SMILES: C#CC(O)(c1ccc(C)cc1)c1ccc(OC)cc1] |

TABLE 5-continued
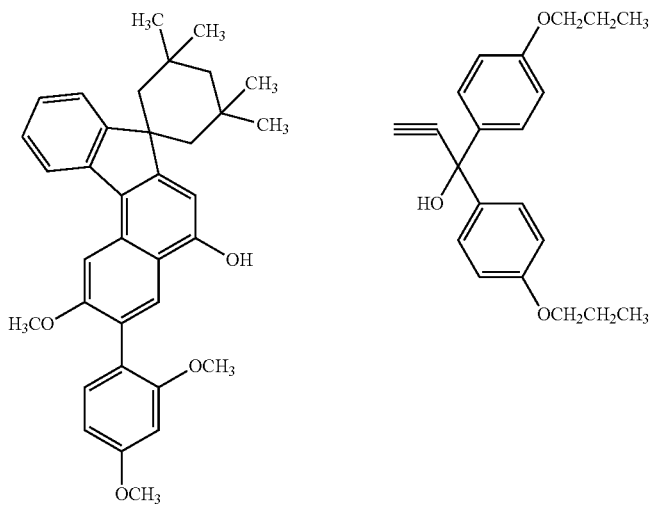
88
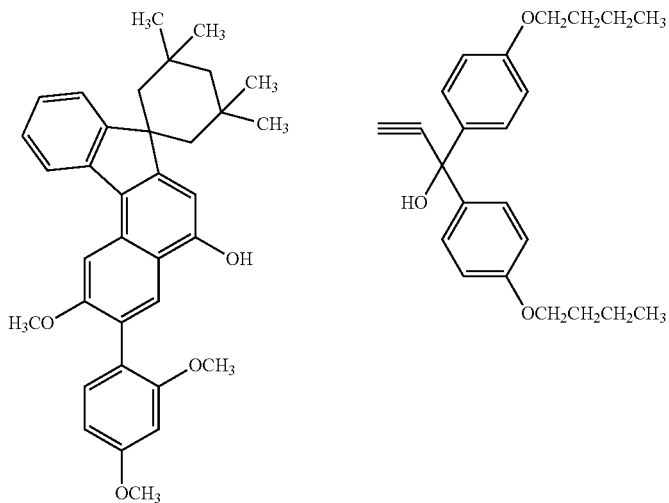
89
| Example No. | Product | Yield rate (%) |
|---|---|---|
| 31 | 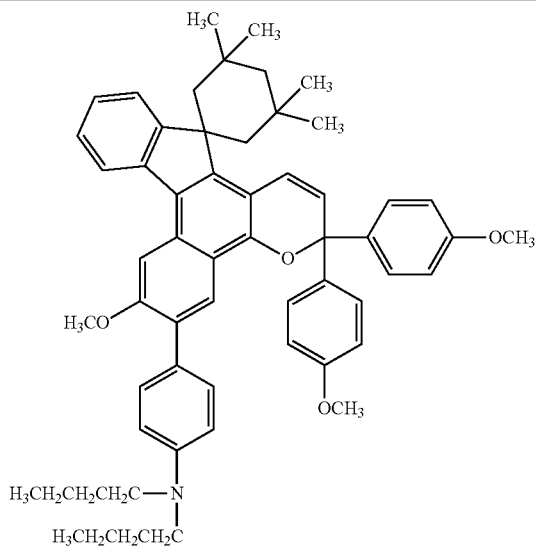 | 67 |

TABLE 5-continued
32 67
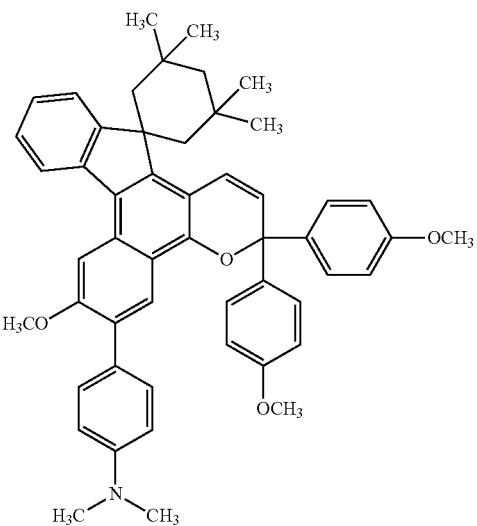 [SMILES: COc1ccc(C2(c3ccc(OC)cc3)C=Cc3c4c(c5cc(OC)c(-c6ccc(N(C)C)cc6)cc5c3O2)-c2ccccc2C42CC(C)(C)CC(C)(C)C2)cc1]
33 55
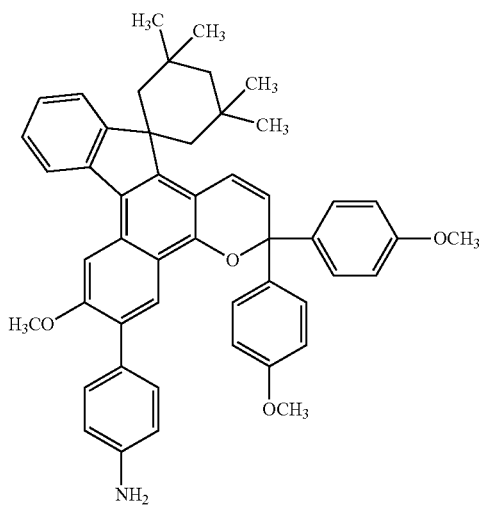
34 56
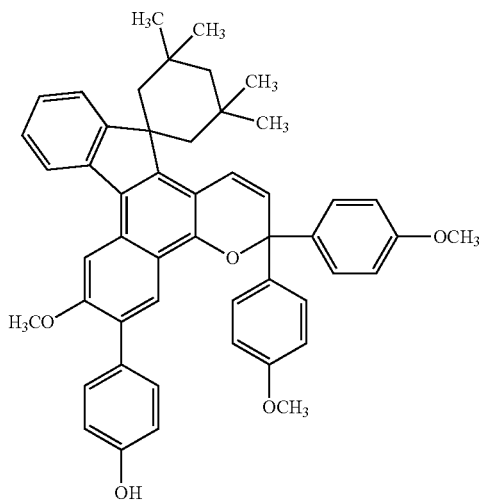 [SMILES: COc1ccc(C2(c3ccc(OC)cc3)C=Cc3c4c(c5cc(OC)c(-c6ccc(O)cc6)cc5c3O2)-c2ccccc2C42CC(C)(C)CC(C)(C)C2)cc1]

TABLE 5-continued
| 35 | 72 |
|---|---|
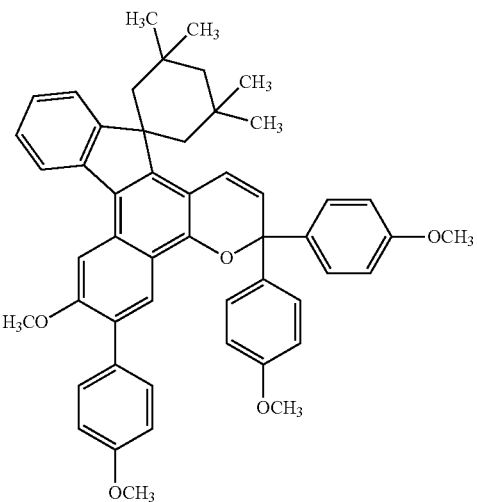 [SMILES: COc1ccc(-c2cc3c4c(c5c(c3cc2OC)-c2ccccc2C52CC(C)(C)CC(C)(C)C2)C=CC(c2ccc(OC)cc2)(c2ccc(OC)cc2)O4)cc1]
| 36 | 67 |
|---|---|
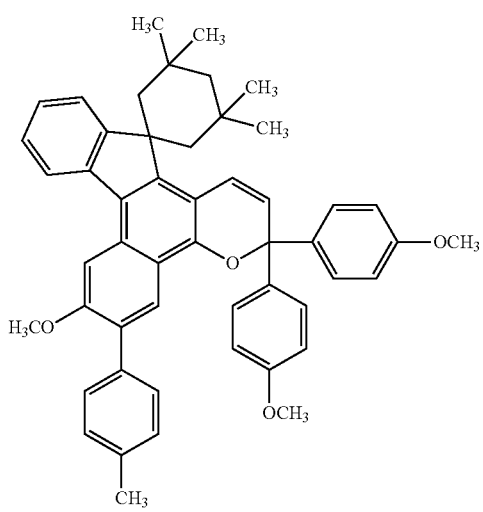 [SMILES: COc1ccc(C2(c3ccc(OC)cc3)C=Cc3c4c(c5cc(OC)c(-c6ccc(C)cc6)cc5c3O2)-c2ccccc2C42CC(C)(C)CC(C)(C)C2)cc1]
| 37 | 66 |
|---|---|
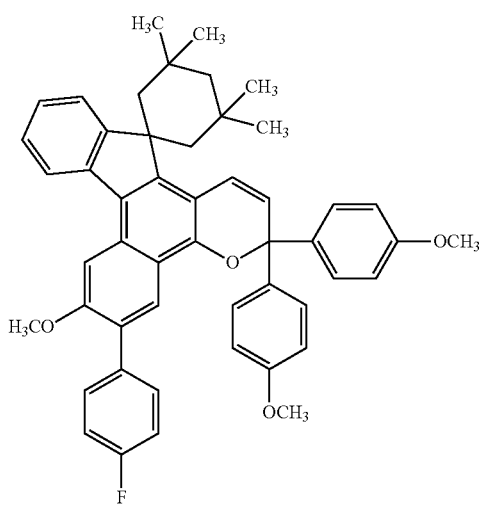 [SMILES: COc1ccc(C2(c3ccc(OC)cc3)C=Cc3c4c(c5cc(OC)c(-c6ccc(F)cc6)cc5c3O2)-c2ccccc2C42CC(C)(C)CC(C)(C)C2)cc1]

TABLE 5-continued
38
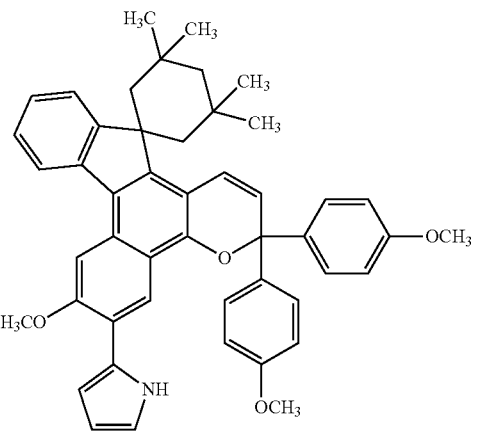 [SMILES: COc1ccc(C2(c3ccc(OC)cc3)C=Cc3c4c(c5cc(OC)c(-c6ccc[nH]6)cc5c3O2)-c2ccccc2C42CC(C)(C)CC(C)(C)C2)cc1]
39
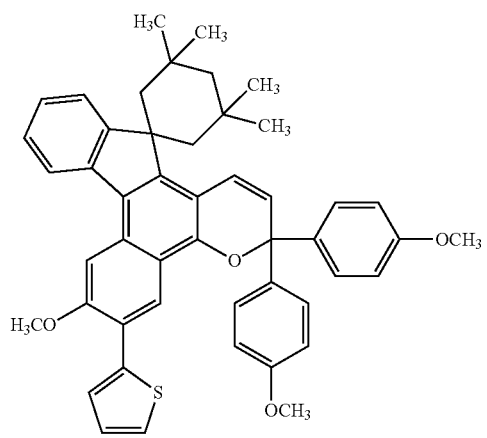 [SMILES: COc1ccc(C2(c3ccc(OC)cc3)C=Cc3c4c(c5cc(OC)c(-c6cccs6)cc5c3O2)-c2ccccc2C42CC(C)(C)CC(C)(C)C2)cc1]
40
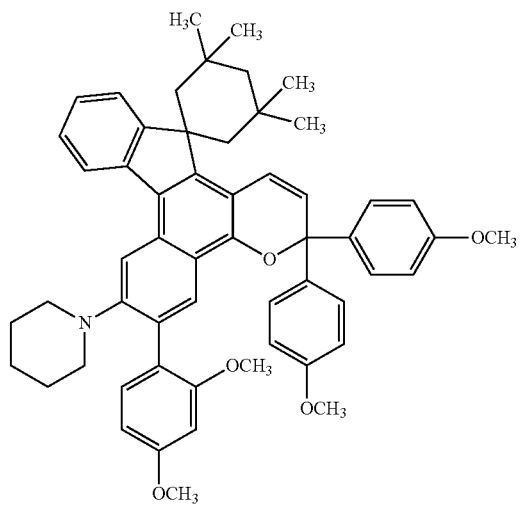
64
63
67

TABLE 5-continued
| 41 | 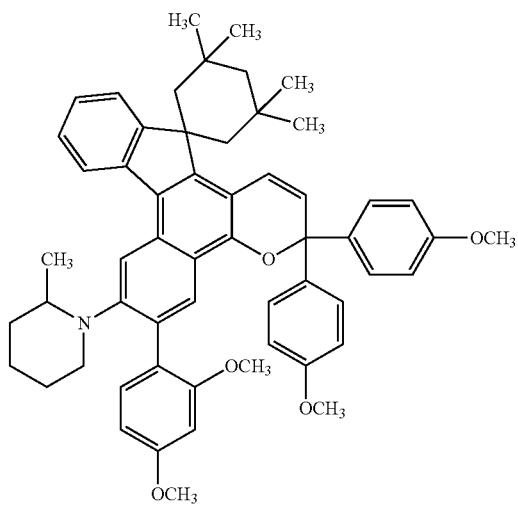 [SMILES: COc1ccc(C2(c3ccc(OC)cc3)C=Cc3c4c(c5cc(N6CCCCC6C)c(-c6ccc(OC)cc6OC)cc5c3O2)-c2ccccc2C42CC(C)(C)CC(C)(C)C2)cc1] | 65 |
| 42 | 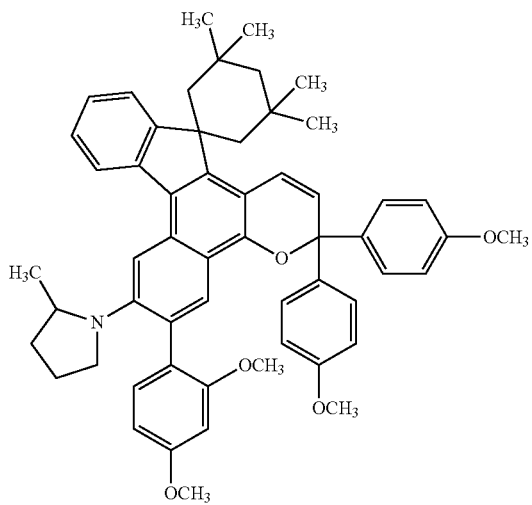 [SMILES: COc1ccc(C2(c3ccc(OC)cc3)C=Cc3c4c(c5cc(N6CCCC6C)c(-c6ccc(OC)cc6OC)cc5c3O2)-c2ccccc2C42CC(C)(C)CC(C)(C)C2)cc1] | 69 |
| 43 | 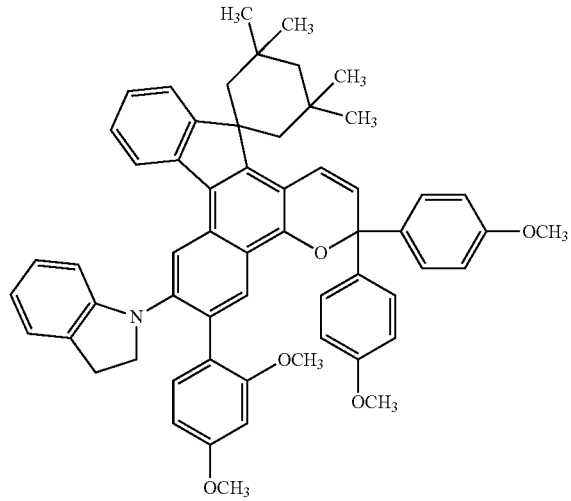 [SMILES: COc1ccc(C2(c3ccc(OC)cc3)C=Cc3c4c(c5cc(N6CCc7ccccc76)c(-c6ccc(OC)cc6OC)cc5c3O2)-c2ccccc2C42CC(C)(C)CC(C)(C)C2)cc1] | 67 |

TABLE 5-continued
| 44 | 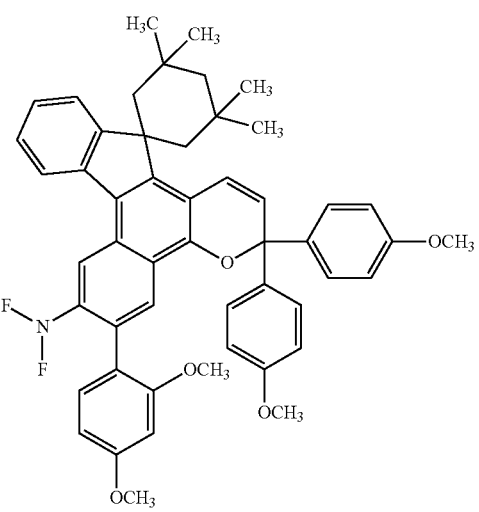 [SMILES: COc1ccc(C2(c3ccc(OC)cc3)C=Cc3c4c(c5cc(N(F)F)c(-c6ccc(OC)cc6OC)cc5c3O2)-c2ccccc2C42CC(C)(C)CC(C)(C)C2)cc1] | 60 |
| 45 | 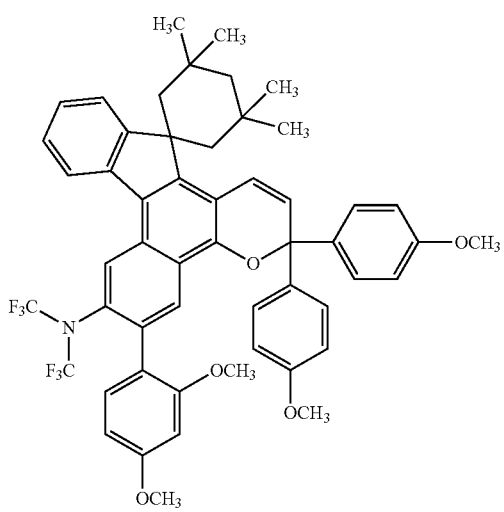 [SMILES: COc1ccc(C2(c3ccc(OC)cc3)C=Cc3c4c(c5cc(N(C(F)(F)F)C(F)(F)F)c(-c6ccc(OC)cc6OC)cc5c3O2)-c2ccccc2C42CC(C)(C)CC(C)(C)C2)cc1] | 63 |
| 46 | 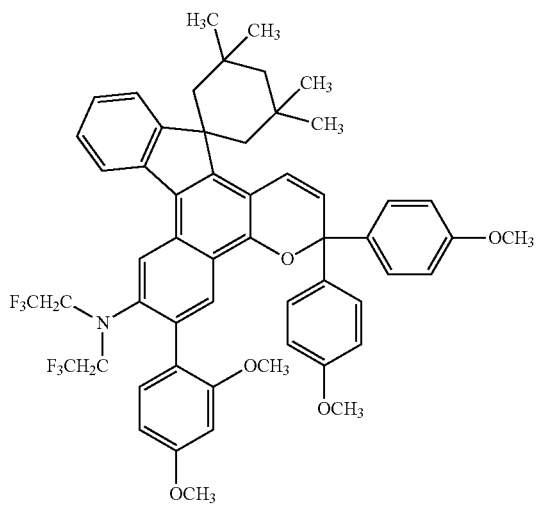 | 62 |

TABLE 5-continued
| 47 | 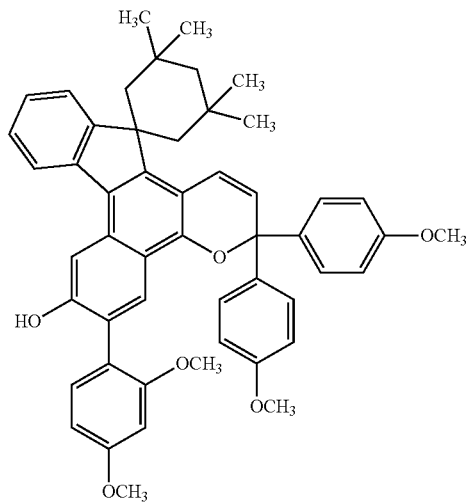 [SMILES: COc1ccc(C2(c3ccc(OC)cc3)C=Cc3c4c(c5cc(O)c(-c6ccc(OC)cc6OC)cc5c3O2)-c2ccccc2C42CC(C)(C)CC(C)(C)C2)cc1] | 54 |
| 48 | 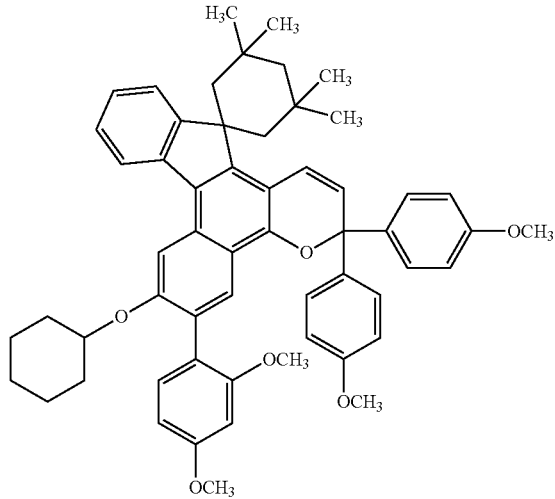 [SMILES: COc1ccc(C2(c3ccc(OC)cc3)C=Cc3c4c(c5cc(OC6CCCCC6)c(-c6ccc(OC)cc6OC)cc5c3O2)-c2ccccc2C42CC(C)(C)CC(C)(C)C2)cc1] | 65 |
| 49 | 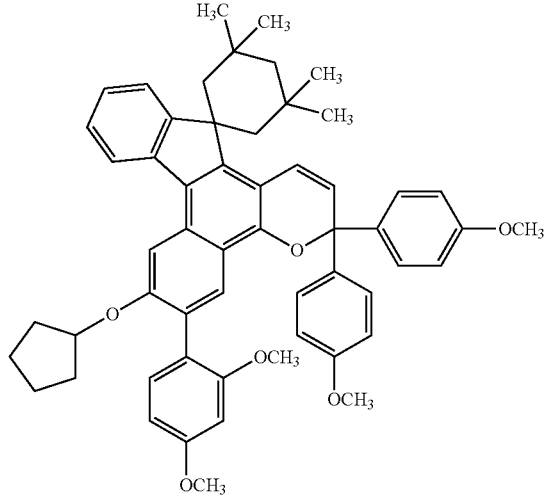 [SMILES: COc1ccc(C2(c3ccc(OC)cc3)C=Cc3c4c(c5cc(OC6CCCC6)c(-c6ccc(OC)cc6OC)cc5c3O2)-c2ccccc2C42CC(C)(C)CC(C)(C)C2)cc1] | 54 |

TABLE 5-continued
50
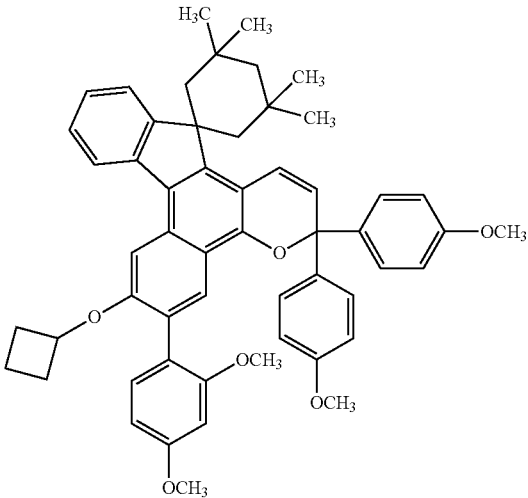 [SMILES: COc1ccc(C2(c3ccc(OC)cc3)C=Cc3c4c(c5cc(OC6CCC6)c(-c6ccc(OC)cc6OC)cc5c3O2)-c2ccccc2C42CC(C)(C)CC(C)(C)C2)cc1]
51
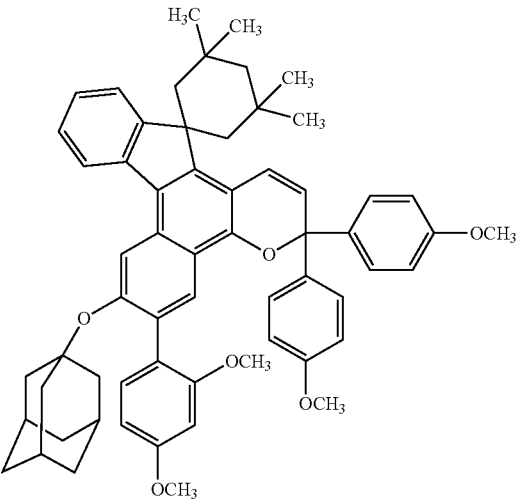 [SMILES: COc1ccc(C2(c3ccc(OC)cc3)C=Cc3c4c(c5cc(OC67CC8CC(CC(C8)C6)C7)c(-c6ccc(OC)cc6OC)cc5c3O2)-c2ccccc2C42CC(C)(C)CC(C)(C)C2)cc1]
52
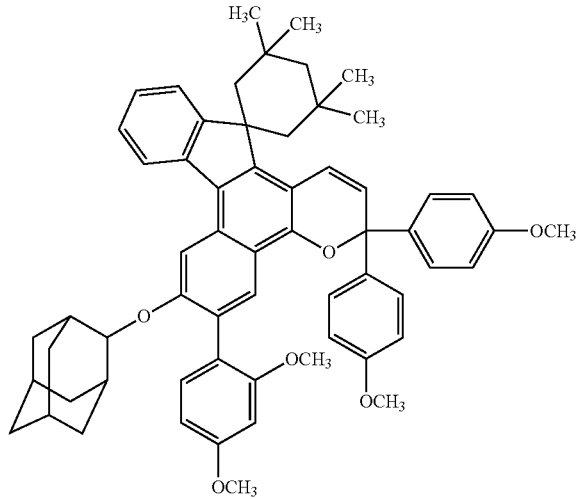 [SMILES: COc1ccc(C2(c3ccc(OC)cc3)C=Cc3c4c(c5cc(OC6C7CC8CC(C7)CC6C8)c(-c6ccc(OC)cc6OC)cc5c3O2)-c2ccccc2C42CC(C)(C)CC(C)(C)C2)cc1]
65
66
67

TABLE 5-continued
53 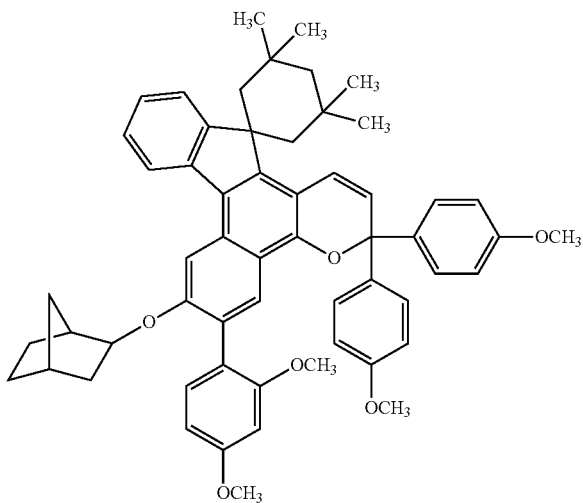 [SMILES: COc1ccc(C2(c3ccc(OC)cc3)C=Cc3c4c(c5cc(OC6CC7CCC6C7)c(-c6ccc(OC)cc6OC)cc5c3O2)-c2ccccc2C42CC(C)(C)CC(C)(C)C2)cc1] 62
54 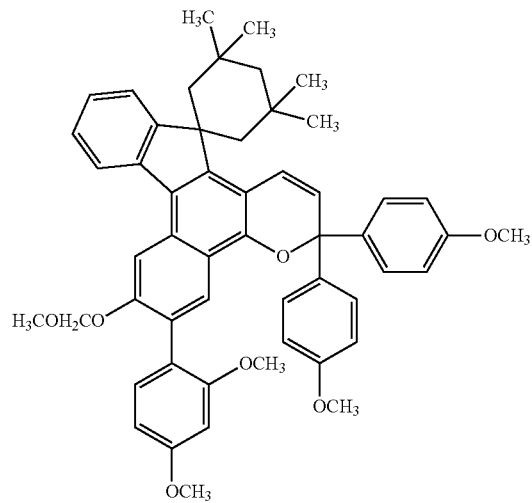 66
55 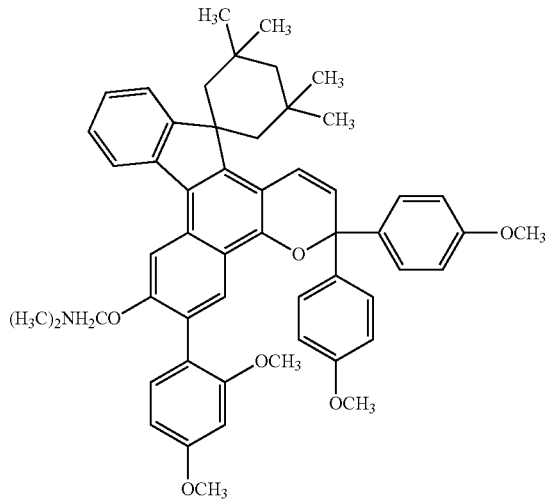 66

TABLE 5-continued
| 56 | 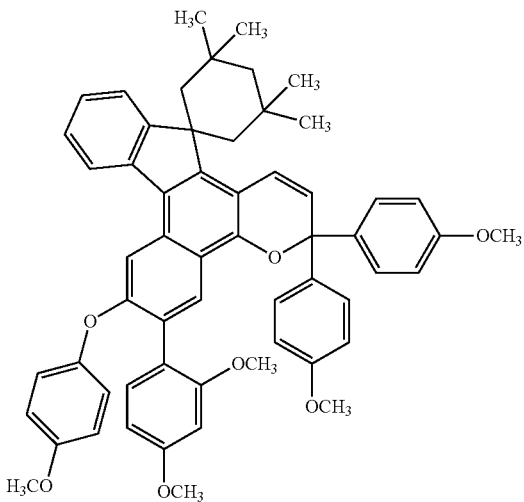 [SMILES: COc1ccc(Oc2cc3c4c(c5c(c3cc2-c2ccc(OC)cc2OC)OC(c2ccc(OC)cc2)(c2ccc(OC)cc2)C=C5)C2(CC(C)(C)CC(C)(C)C2)c2ccccc2-4)cc1] | 65 |
| 57 | 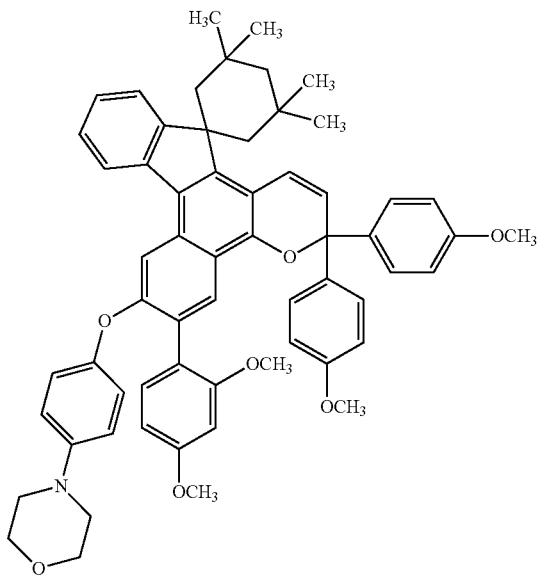 [SMILES: COc1ccc(C2(c3ccc(OC)cc3)C=Cc3c4c(c5cc(Oc6ccc(N7CCOCC7)cc6)c(-c6ccc(OC)cc6OC)cc5c3O2)-c2ccccc2C42CC(C)(C)CC(C)(C)C2)cc1] | 64 |
| 58 | 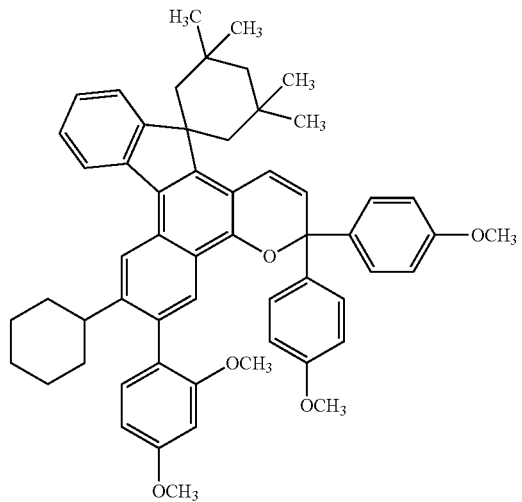 [SMILES: COc1ccc(C2(c3ccc(OC)cc3)C=Cc3c4c(c5cc(C6CCCCC6)c(-c6ccc(OC)cc6OC)cc5c3O2)-c2ccccc2C42CC(C)(C)CC(C)(C)C2)cc1] | 70 |

TABLE 5-continued
59
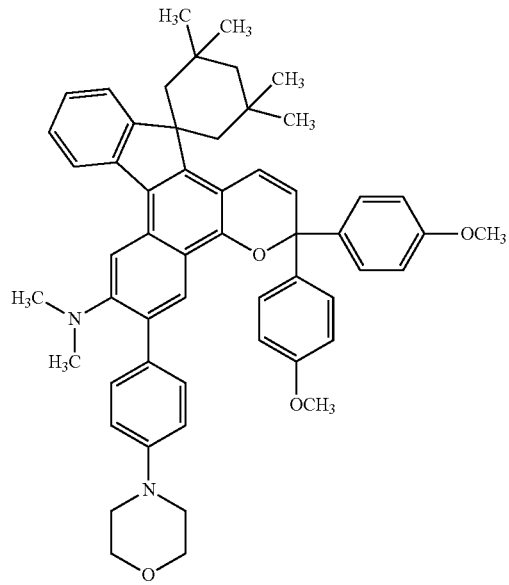 [SMILES: COc1ccc(C2(c3ccc(OC)cc3)C=Cc3c4c(c5cc(N(C)C)c(-c6ccc(N7CCOCC7)cc6)cc5c3O2)-c2ccccc2C42CC(C)(C)CC(C)(C)C2)cc1]
69
60
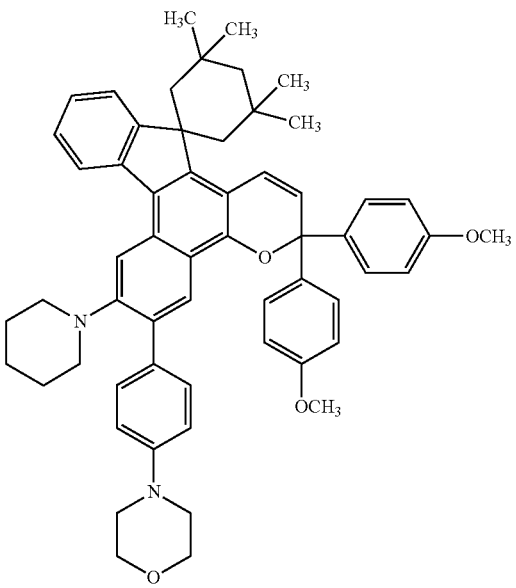 [SMILES: COc1ccc(C2(c3ccc(OC)cc3)C=Cc3c4c(c5cc(N6CCCCC6)c(-c6ccc(N7CCOCC7)cc6)cc5c3O2)-c2ccccc2C42CC(C)(C)CC(C)(C)C2)cc1]
66

TABLE 5-continued
61
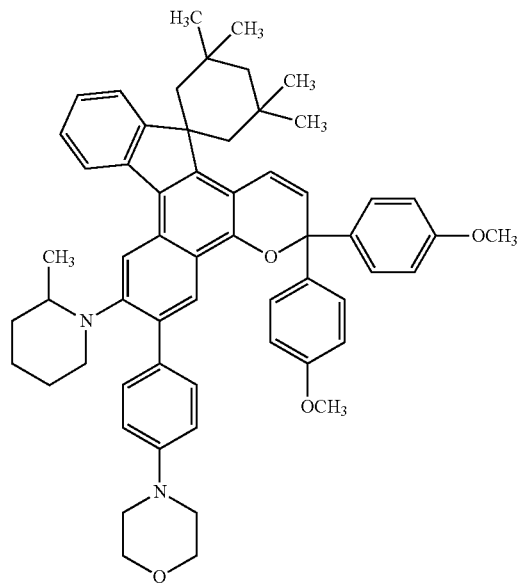 [SMILES: COc1ccc(C2(c3ccc(OC)cc3)C=Cc3c4c(c5cc(N6CCCCC6C)c(-c6ccc(N7CCOCC7)cc6)cc5c3O2)-c2ccccc2C42CC(C)(C)CC(C)(C)C2)cc1]
66
62
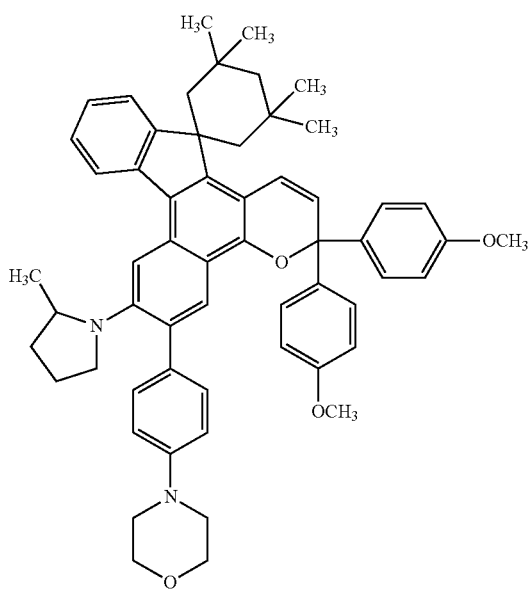 [SMILES: COc1ccc(C2(c3ccc(OC)cc3)C=Cc3c4c(c5cc(N6CCCC6C)c(-c6ccc(N7CCOCC7)cc6)cc5c3O2)-c2ccccc2C42CC(C)(C)CC(C)(C)C2)cc1]
65

TABLE 5-continued
63
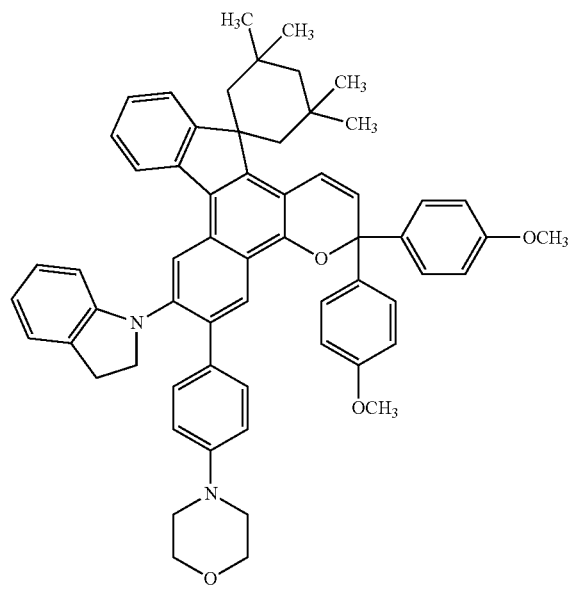 [SMILES: COc1ccc(C2(c3ccc(OC)cc3)C=Cc3c4c(c5cc(N6CCc7ccccc76)c(-c6ccc(N7CCOCC7)cc6)cc5c3O2)-c2ccccc2C42CC(C)(C)CC(C)(C)C2)cc1]
67
64
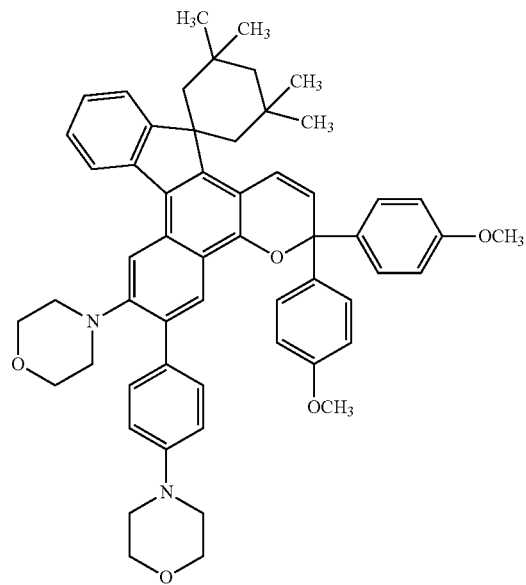 [SMILES: COc1ccc(C2(c3ccc(OC)cc3)C=Cc3c4c(c5cc(N6CCOCC6)c(-c6ccc(N7CCOCC7)cc6)cc5c3O2)-c2ccccc2C42CC(C)(C)CC(C)(C)C2)cc1]
70

TABLE 5-continued
| 65 | 60 |
|---|---|
| 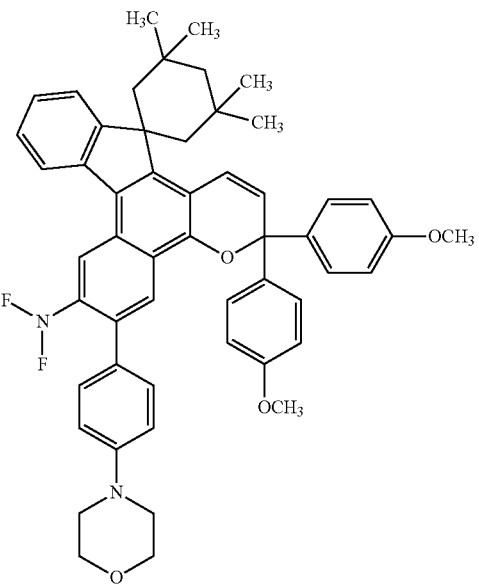 [SMILES: COc1ccc(C2(c3ccc(OC)cc3)C=Cc3c4c(c5cc(N(F)F)c(-c6ccc(N7CCOCC7)cc6)cc5c3O2)-c2ccccc2C42CC(C)(C)CC(C)(C)C2)cc1] | |
| 66 | 63 |
|---|---|
| 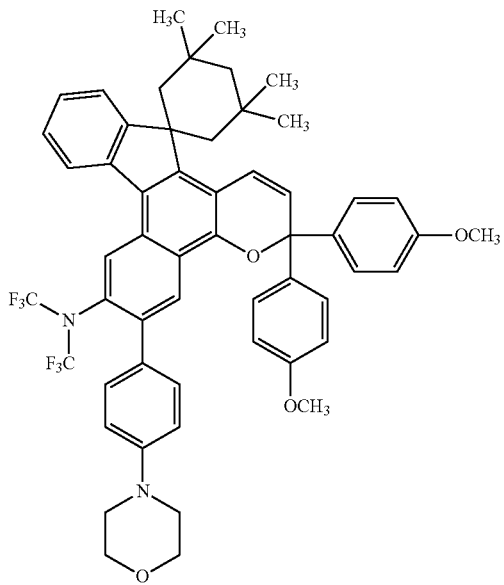 [SMILES: COc1ccc(C2(c3ccc(OC)cc3)C=Cc3c4c(c5cc(N(C(F)(F)F)C(F)(F)F)c(-c6ccc(N7CCOCC7)cc6)cc5c3O2)-c2ccccc2C42CC(C)(C)CC(C)(C)C2)cc1] | |

TABLE 5-continued
67
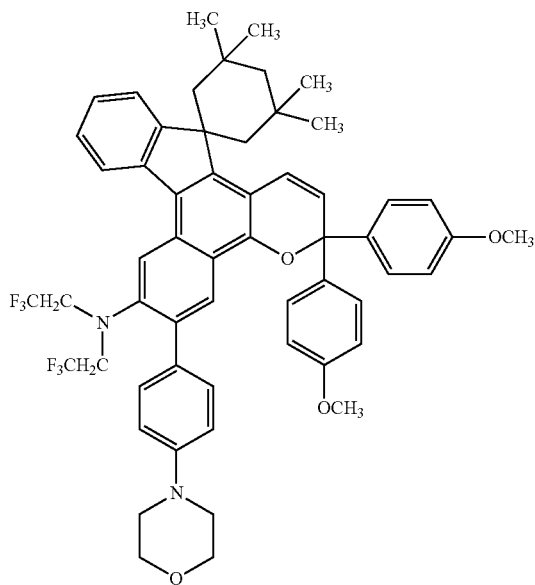
64
68
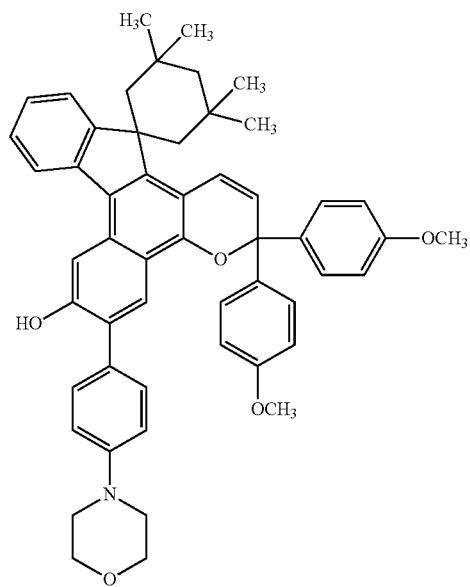
52

TABLE 5-continued
| 69 | | 71 |
|---|---|---|
| | 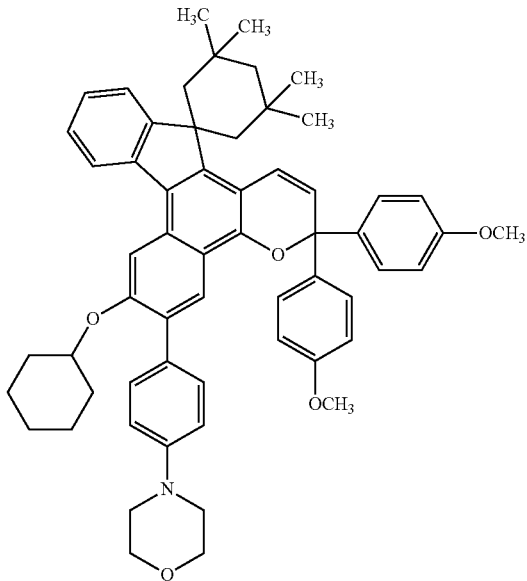 [SMILES: COc1ccc(C2(c3ccc(OC)cc3)C=Cc3c4c(c5cc(OC6CCCCC6)c(-c6ccc(N7CCOCC7)cc6)cc5c3O2)-c2ccccc2C42CC(C)(C)CC(C)(C)C2)cc1] | |
| 70 | | 69 |
|---|---|---|
| | 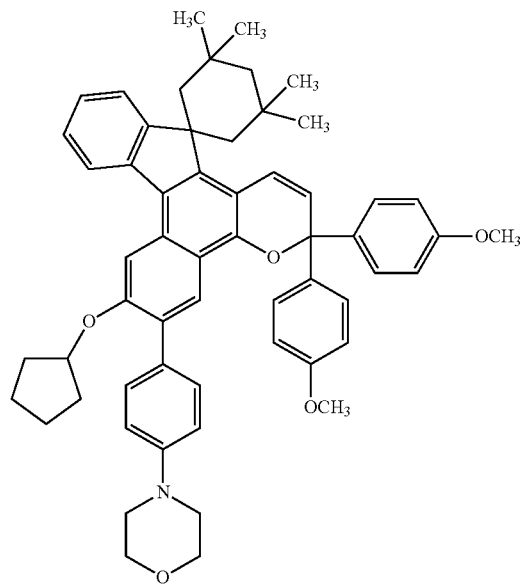 [SMILES: COc1ccc(C2(c3ccc(OC)cc3)C=Cc3c4c(c5cc(OC6CCCC6)c(-c6ccc(N7CCOCC7)cc6)cc5c3O2)-c2ccccc2C42CC(C)(C)CC(C)(C)C2)cc1] | |

TABLE 5-continued
| 71 | 68 |
|----|----|
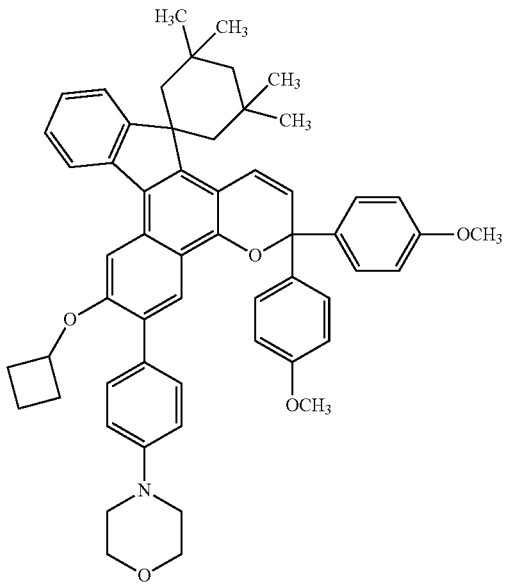 [SMILES: COc1ccc(C2(c3ccc(OC)cc3)C=Cc3c4c(c5cc(OC6CCC6)c(-c6ccc(N7CCOCC7)cc6)cc5c3O2)-c2ccccc2C42CC(C)(C)CC(C)(C)C2)cc1]
| 72 | 69 |
|----|----|
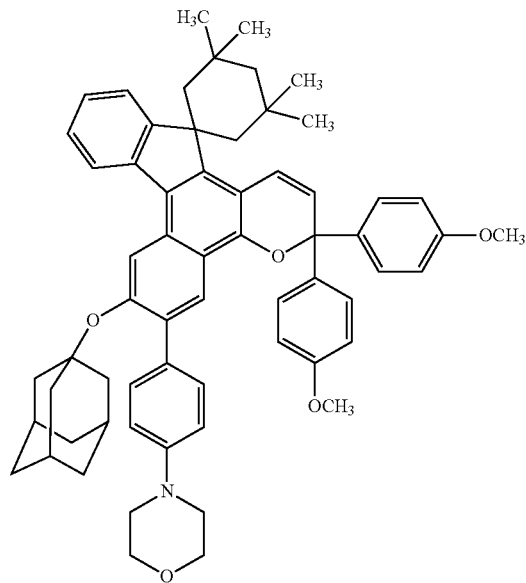 [SMILES: COc1ccc(C2(c3ccc(OC)cc3)C=Cc3c4c(c5cc(OC67CC8CC(CC(C8)C6)C7)c(-c6ccc(N7CCOCC7)cc6)cc5c3O2)-c2ccccc2C42CC(C)(C)CC(C)(C)C2)cc1]

TABLE 5-continued
73 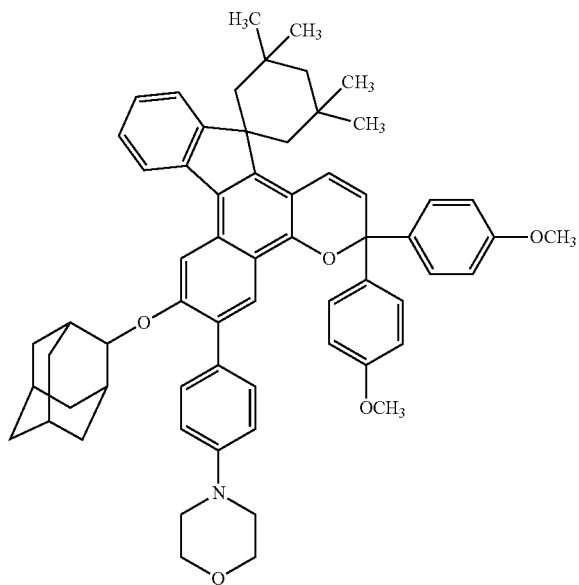 [SMILES: COc1ccc(C2(c3ccc(OC)cc3)C=Cc3c4c(c5cc(OC6C7CC8CC(C7)CC6C8)c(-c6ccc(N7CCOCC7)cc6)cc5c3O2)-c2ccccc2C42CC(C)(C)CC(C)(C)C2)cc1] 66
74 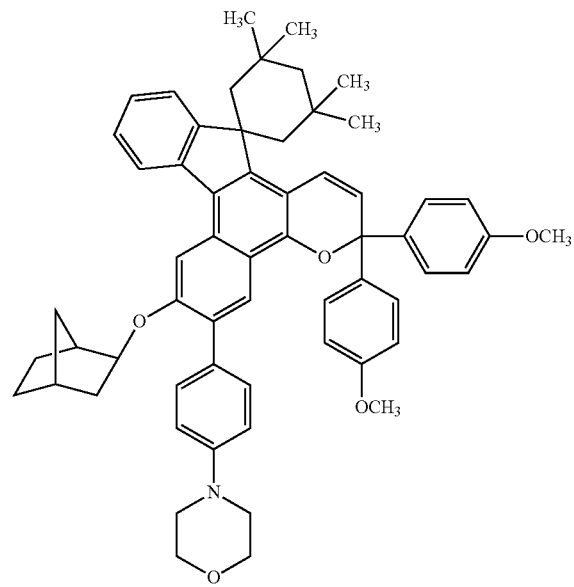 [SMILES: COc1ccc(C2(c3ccc(OC)cc3)C=Cc3c4c(c5cc(OC6CC7CCC6C7)c(-c6ccc(N7CCOCC7)cc6)cc5c3O2)-c2ccccc2C42CC(C)(C)CC(C)(C)C2)cc1] 67

TABLE 5-continued
75
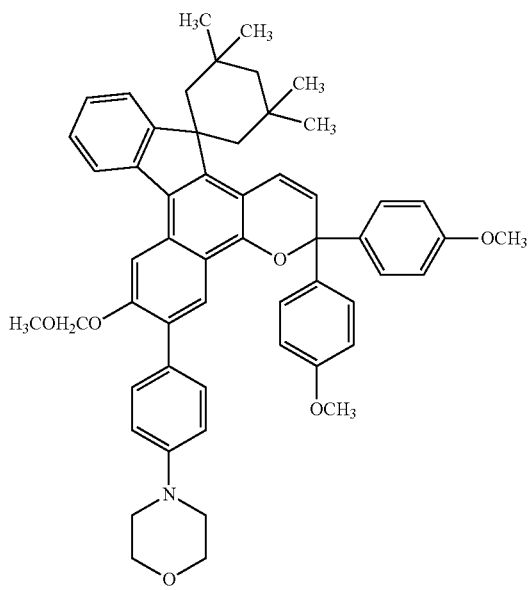
70
76
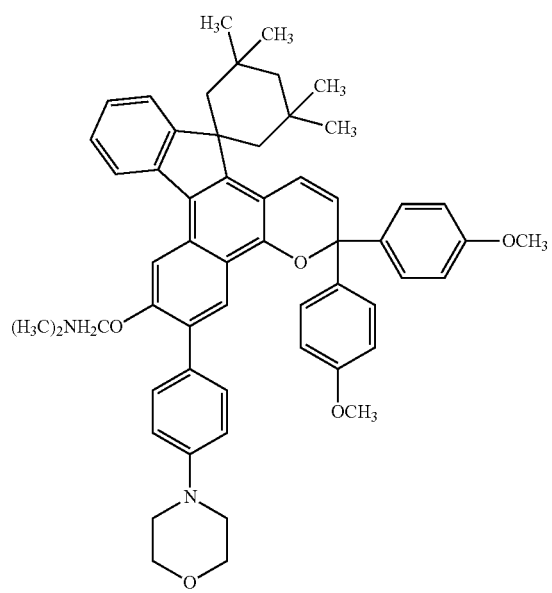
67

TABLE 5-continued
77  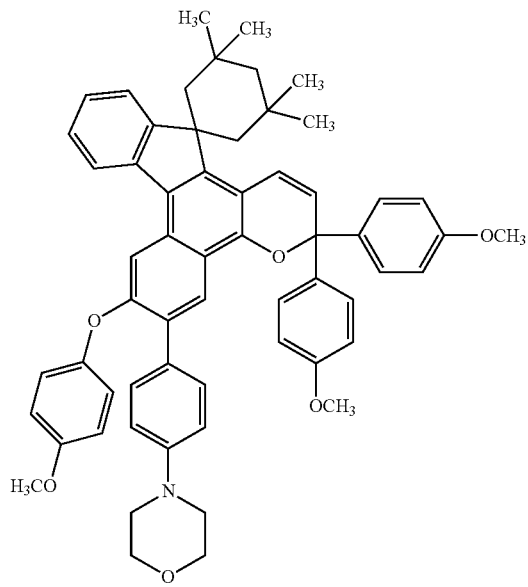 [SMILES: COc1ccc(Oc2cc3c4c(c5c(c3cc2-c2ccc(N3CCOCC3)cc2)OC(c2ccc(OC)cc2)(c2ccc(OC)cc2)C=C5)C2(CC(C)(C)CC(C)(C)C2)c2ccccc2-4)cc1]  66
78  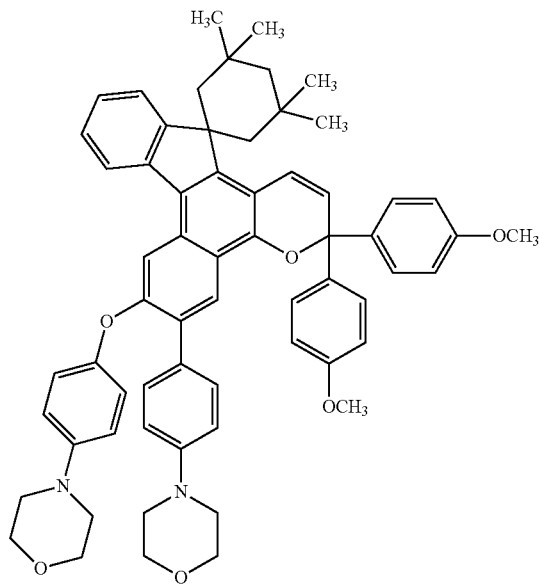 [SMILES: COc1ccc(C2(c3ccc(OC)cc3)C=Cc3c4c(c5cc(Oc6ccc(N7CCOCC7)cc6)c(-c6ccc(N7CCOCC7)cc6)cc5c3O2)-c2ccccc2C42CC(C)(C)CC(C)(C)C2)cc1]  67

TABLE 5-continued
| 79 | 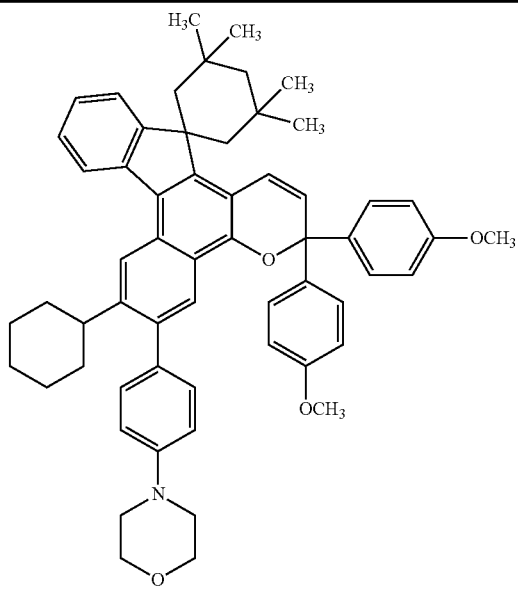 | 71 |
| 80 | 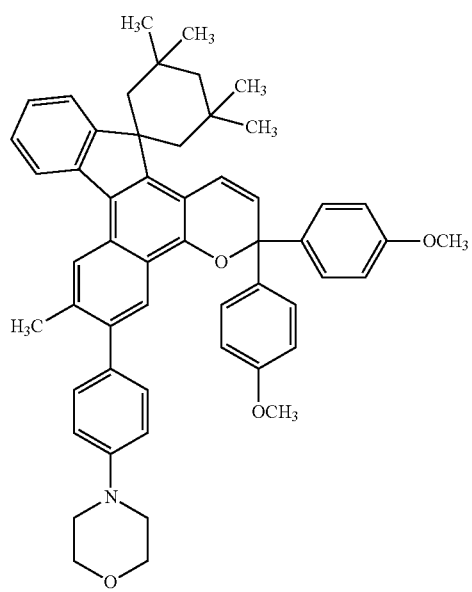 | 70 |
| 81 | 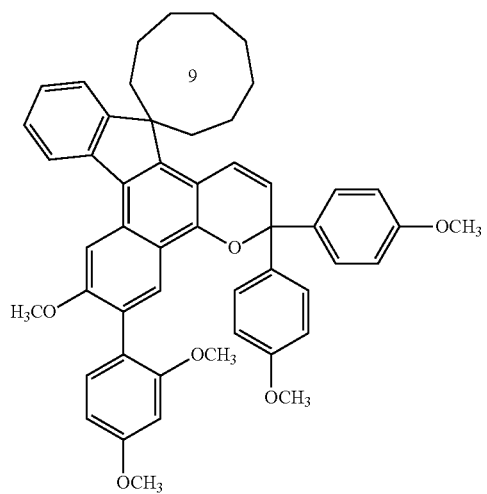 [SMILES: COc1ccc(C2(c3ccc(OC)cc3)C=Cc3c4c(c5cc(OC)c(-c6ccc(OC)cc6OC)cc5c3O2)-c2ccccc2C42CCCCCCCC2)cc1] | 67 |

TABLE 5-continued
82
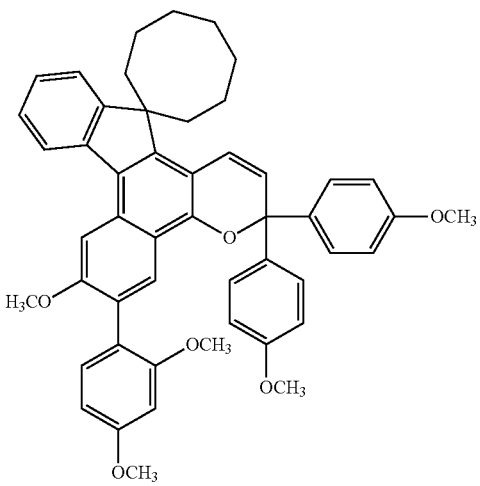 [SMILES: COc1ccc(C2(c3ccc(OC)cc3)C=Cc3c4c(c5cc(OC)c(-c6ccc(OC)cc6OC)cc5c3O2)-c2ccccc2C42CCCCCCC2)cc1]
70
83
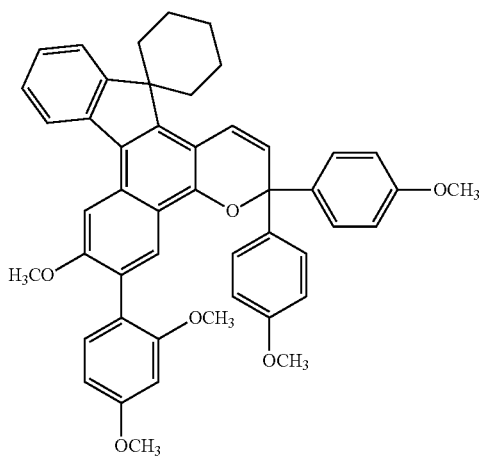 [SMILES: COc1ccc(C2(c3ccc(OC)cc3)C=Cc3c4c(c5cc(OC)c(-c6ccc(OC)cc6OC)cc5c3O2)-c2ccccc2C42CCCCC2)cc1]
68
84
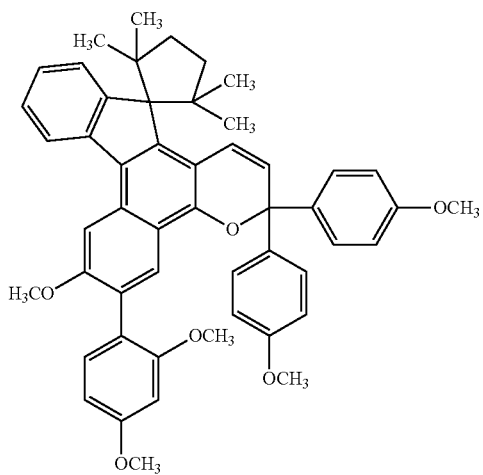 [SMILES: COc1ccc(C2(c3ccc(OC)cc3)C=Cc3c4c(c5cc(OC)c(-c6ccc(OC)cc6OC)cc5c3O2)-c2ccccc2C42C(C)(C)CCC2(C)C)cc1]
69

TABLE 5-continued
85 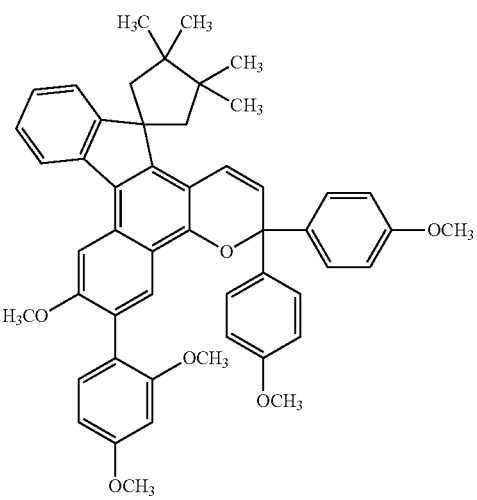 [SMILES: COc1ccc(C2(c3ccc(OC)cc3)C=Cc3c4c(c5cc(OC)c(-c6ccc(OC)cc6OC)cc5c3O2)-c2ccccc2C42CC(C)(C)C(C)(C)C2)cc1] 70
86 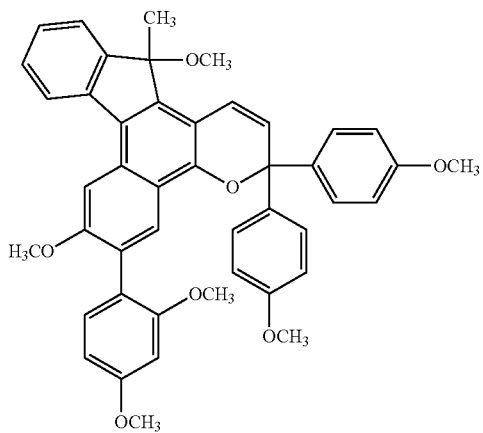 [SMILES: COc1ccc(C2(c3ccc(OC)cc3)C=Cc3c4c(c5cc(OC)c(-c6ccc(OC)cc6OC)cc5c3O2)-c2ccccc2C4(C)OC)cc1] 72
87 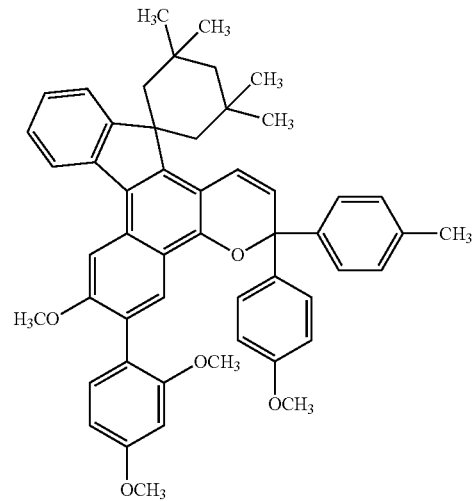 [SMILES: COc1ccc(C2(c3ccc(C)cc3)C=Cc3c4c(c5cc(OC)c(-c6ccc(OC)cc6OC)cc5c3O2)-c2ccccc2C42CC(C)(C)CC(C)(C)C2)cc1] 73

TABLE 5-continued
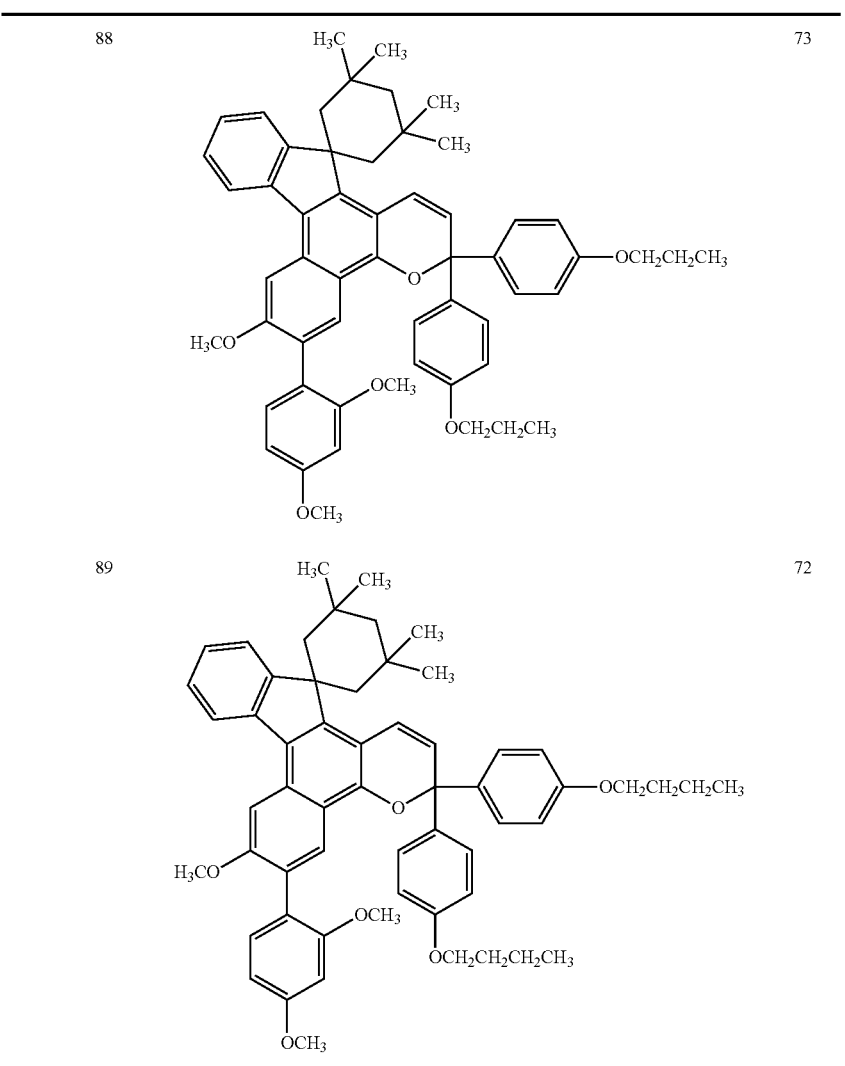
TABLE 6
| | Elemental analysis values | | | | | | | |
|---|---|---|---|---|---|---|---|---|
| | Experimental values | | | | Calculated values | | | |
| Example No. | C | H | N | O | C | H | N | O | ¹H-NMR (NMR) |
| 31 | 82.99 | 7.77 | 1.61 | 7.63 | 82.92 | 7.80 | 1.67 | 7.62 | δ5.0-9.0 20H δ0.5-4.5 45H |
| 32 | 82.68 | 7.09 | 1.81 | 8.42 | 82.62 | 7.07 | 1.85 | 8.47 | δ5.0-9.0 20H δ0.5-4.5 33H |
| 33 | 82.41 | 6.77 | 1.90 | 8.92 | 82.50 | 6.78 | 1.92 | 8.79 | δ5.0-9.0 20H δ0.5-4.5 29H |
| 34 | 82.33 | 6.66 | 0.00 | 11.01 | 82.39 | 6.64 | 0.00 | 10.97 | δ5.0-9.0 20H δ0.5-4.5 28H |
| 35 | 82.55 | 6.77 | 0.00 | 10.68 | 82.45 | 6.78 | 0.00 | 10.77 | δ5.0-9.0 20H δ0.5-4.5 30H |
| 36 | 84.32 | 6.93 | 0.00 | 8.75 | 84.26 | 6.93 | 0.00 | 8.80 | δ5.0-9.0 20H δ0.5-4.5 30H |
| 37 | 82.11 | 6.49 | 0.00 | — | 82.16 | 6.48 | 0.00 | 8.76 | δ5.0-9.0 20H δ0.5-4.5 27H |
| 38 | 82.22 | 6.69 | 1.99 | 9.10 | 82.14 | 6.75 | 2.00 | 9.12 | δ5.0-9.0 19H δ0.5-4.5 28H |
| 39 | 80.11 | 6.55 | 0.00 | — | 80.19 | 6.45 | 0.00 | 8.90 | δ5.0-9.0 19H δ0.5-4.5 27H |
| 40 | 81.44 | 7.29 | 1.72 | 9.55 | 81.42 | 7.20 | 1.70 | 9.68 | δ5.0-9.0 19H δ0.5-4.5 40H |

TABLE 6-continued

| | Elemental analysis values | | | | | | | | |
|---|---|---|---|---|---|---|---|---|---|
| | Experimental values | | | | Calculated values | | | | |
| Example No. | C | H | N | O | C | H | N | O | $^1$H-NMR (NMR) |
| 41 | 81.50 | 7.33 | 1.62 | 9.55 | 81.49 | 7.32 | 1.67 | 9.52 | δ5.0-9.0 19H |
| | | | | | | | | | δ0.5-4.5 42H |
| 42 | 81.44 | 7.31 | 1.67 | 9.58 | 81.42 | 7.20 | 1.70 | 9.68 | δ5.0-9.0 19H |
| | | | | | | | | | δ0.5-4.5 40H |
| 43 | 82.31 | 6.72 | 1.66 | 9.31 | 82.39 | 6.68 | 1.63 | 9.30 | δ5.0-9.0 23H |
| | | | | | | | | | δ0.5-4.5 34H |
| 44 | 77.12 | 6.12 | 1.78 | — | 77.15 | 6.22 | 1.76 | 10.08 | δ5.0-9.0 19H |
| | | | | | | | | | δ0.5-4.5 30H |
| 45 | 71.31 | 5.46 | 1.55 | — | 71.21 | 5.52 | 1.57 | 8.95 | δ5.0-9.0 19H |
| | | | | | | | | | δ0.5-4.5 30H |
| 46 | 71.57 | 5.80 | 1.55 | — | 71.65 | 5.79 | 1.52 | 8.68 | δ5.0-9.0 19H |
| | | | | | | | | | δ0.5-4.5 34H |
| 47 | 80.77 | 6.58 | 0.00 | 12.65 | 80.71 | 6.64 | 0.00 | 12.65 | δ5.0-9.0 19H |
| | | | | | | | | | δ0.5-4.5 31H |
| 48 | 81.43 | 7.12 | 0.00 | 11.45 | 81.40 | 7.19 | 0.00 | 11.41 | δ5.0-9.0 19H |
| | | | | | | | | | δ0.5-4.5 41H |
| 49 | 81.34 | 7.09 | 0.00 | 11.57 | 81.32 | 7.07 | 0.00 | 11.61 | δ5.0-9.0 19H |
| | | | | | | | | | δ0.5-4.5 39H |
| 50 | 81.29 | 6.91 | 0.00 | 11.80 | 81.25 | 6.94 | 0.00 | 11.81 | δ5.0-9.0 19H |
| | | | | | | | | | δ0.5-4.5 37H |
| 51 | 81.99 | 7.23 | 0.00 | 10.78 | 82.03 | 7.22 | 0.00 | 10.75 | δ5.0-9.0 19H |
| | | | | | | | | | δ0.5-4.5 45H |
| 52 | 82.02 | 7.25 | 0.00 | 10.73 | 82.03 | 7.22 | 0.00 | 10.75 | δ5.0-9.0 19H |
| | | | | | | | | | δ0.5-4.5 45H |
| 53 | 81.59 | 7.02 | 0.00 | 11.39 | 81.66 | 7.09 | 0.00 | 11.25 | δ5.0-9.0 19H |
| | | | | | | | | | δ0.5-4.5 41H |
| 54 | 79.33 | 6.69 | 0.00 | 13.98 | 79.27 | 6.78 | 0.00 | 13.95 | δ5.0-9.0 19H |
| | | | | | | | | | δ0.5-4.5 35H |
| 55 | 79.52 | 7.05 | 1.70 | 11.73 | 79.48 | 7.04 | 1.72 | 11.76 | δ5.0-9.0 19H |
| | | | | | | | | | δ0.5-4.5 38H |
| 56 | 80.55 | 6.51 | 0.00 | 12.94 | 80.53 | 6.52 | 0.00 | 12.95 | δ5.0-9.0 23H |
| | | | | | | | | | δ0.5-4.5 33H |
| 57 | 79.59 | 6.66 | 1.50 | 12.25 | 79.62 | 6.68 | 1.52 | 12.17 | δ5.0-9.0 23H |
| | | | | | | | | | δ0.5-4.5 38H |
| 58 | 82.99 | 7.39 | 0.00 | 9.62 | 82.97 | 7.33 | 0.00 | 9.70 | δ5.0-9.0 19H |
| | | | | | | | | | δ0.5-4.5 41H |
| 59 | 81.43 | 7.24 | 3.44 | 7.89 | 81.45 | 7.21 | 3.45 | 7.89 | δ5.0-9.0 20H |
| | | | | | | | | | δ0.5-4.5 38H |
| 60 | 81.88 | 7.34 | 3.23 | 7.55 | 81.85 | 7.34 | 3.29 | 7.52 | δ5.0-9.0 20H |
| | | | | | | | | | δ0.5-4.5 42H |
| 61 | 81.90 | 7.41 | 3.23 | 7.46 | 81.91 | 7.46 | 3.24 | 7.40 | δ5.0-9.0 20H |
| | | | | | | | | | δ0.5-4.5 44H |
| 62 | 81.82 | 7.38 | 3.33 | 7.47 | 81.85 | 7.34 | 3.29 | 7.52 | δ5.0-9.0 20H |
| | | | | | | | | | δ0.5-4.5 42H |
| 63 | 82.69 | 6.88 | 3.21 | 7.22 | 82.77 | 6.83 | 3.16 | 7.23 | δ5.0-9.0 24H |
| | | | | | | | | | δ0.5-4.5 36H |
| 64 | 80.32 | 7.00 | 3.30 | 9.38 | 80.25 | 7.09 | 3.28 | 9.38 | δ5.0-9.0 20H |
| | | | | | | | | | δ0.5-4.5 40H |
| 65 | 77.73 | 6.45 | 3.38 | — | 77.73 | 6.40 | 3.42 | 7.81 | δ5.0-9.0 20H |
| | | | | | | | | | δ0.5-4.5 32H |
| 66 | 71.90 | 5.69 | 3.04 | — | 71.88 | 5.70 | 3.05 | 6.96 | δ5.0-9.0 20H |
| | | | | | | | | | δ0.5-4.5 32H |
| 67 | 72.30 | 5.99 | 2.87 | — | 72.29 | 5.96 | 2.96 | 6.76 | δ5.0-9.0 20H |
| | | | | | | | | | δ0.5-4.5 36H |
| 68 | 81.22 | 6.84 | 1.81 | 10.13 | 81.20 | 6.81 | 1.79 | 10.20 | δ5.0-9.0 20H |
| | | | | | | | | | δ0.5-4.5 33H |
| 69 | 81.89 | 7.32 | 1.61 | 9.18 | 81.82 | 7.33 | 1.62 | 9.24 | δ5.0-9.0 20H |
| | | | | | | | | | δ0.5-4.5 43H |
| 70 | 81.71 | 7.23 | 1.65 | 9.41 | 81.75 | 7.22 | 1.64 | 9.39 | δ5.0-9.0 20H |
| | | | | | | | | | δ0.5-4.5 41H |
| 71 | 81.67 | 7.12 | 1.66 | 9.55 | 81.69 | 7.10 | 1.67 | 9.55 | δ5.0-9.0 20H |
| | | | | | | | | | δ0.5-4.5 39H |
| 72 | 82.44 | 7.38 | 1.55 | 8.63 | 82.41 | 7.35 | 1.53 | 8.71 | δ5.0-9.0 20H |
| | | | | | | | | | δ0.5-4.5 47H |
| 73 | 82.44 | 7.41 | 1.52 | 8.63 | 82.41 | 7.35 | 1.53 | 8.71 | δ5.0-9.0 20H |
| | | | | | | | | | δ0.5-4.5 47H |
| 74 | 82.00 | 7.26 | 1.62 | 9.12 | 82.06 | 7.23 | 1.60 | 9.11 | δ5.0-9.0 20H |
| | | | | | | | | | δ0.5-4.5 43H |
| 75 | 79.76 | 6.97 | 1.66 | 11.61 | 79.78 | 6.94 | 1.69 | 11.59 | δ5.0-9.0 20H |
| | | | | | | | | | δ0.5-4.5 37H |
| 76 | 79.99 | 7.11 | 3.41 | 9.49 | 79.97 | 7.19 | 3.33 | 9.51 | δ5.0-9.0 20H |
| | | | | | | | | | δ0.5-4.5 40H |
| 77 | 80.99 | 6.66 | 1.54 | 10.81 | 80.96 | 6.68 | 1.57 | 10.78 | δ5.0-9.0 24H |
| | | | | | | | | | δ0.5-4.5 35H |

TABLE 6-continued

| | Elemental analysis values | | | | | | | | |
|---|---|---|---|---|---|---|---|---|---|
| | Experimental values | | | | Calculated values | | | | |
| Example No. | C | H | N | O | C | H | N | O | ¹H-NMR (NMR) |
| 78 | 80.05 | 6.78 | 2.89 | 10.28 | 80.06 | 6.82 | 2.96 | 10.16 | δ5.0-9.0 24H<br>δ0.5-4.5 40H |
| 79 | 83.34 | 7.45 | 1.66 | 7.55 | 83.36 | 7.47 | 1.65 | 7.53 | δ5.0-9.0 20H<br>δ0.5-4.5 43H |
| 80 | 83.00 | 7.04 | 1.77 | 8.19 | 82.94 | 7.09 | 1.79 | 8.18 | δ5.0-9.0 20H<br>δ0.5-4.5 35H |
| 81 | 80.77 | 6.67 | 0.00 | 12.56 | 80.71 | 6.64 | 0.00 | 12.65 | δ5.0-9.0 19H<br>δ0.5-4.5 31H |
| 82 | 80.65 | 6.39 | 0.00 | 12.96 | 80.62 | 6.49 | 0.00 | 12.89 | δ5.0-9.0 19H<br>δ0.5-4.5 29H |
| 83 | 80.44 | 6.21 | 0.00 | 13.35 | 80.42 | 6.19 | 0.00 | 13.39 | δ5.0-9.0 19H<br>δ0.5-4.5 25H |
| 84 | 80.74 | 6.66 | 0.00 | 12.60 | 80.71 | 6.64 | 0.00 | 12.65 | δ5.0-9.0 19H<br>δ0.5-4.5 31H |
| 85 | 80.67 | 6.68 | 0.00 | 12.65 | 80.71 | 6.64 | 0.00 | 12.65 | δ5.0-9.0 19H<br>δ0.5-4.5 31H |
| 86 | 78.00 | 5.87 | 0.00 | 16.13 | 78.01 | 5.82 | 0.00 | 16.17 | δ5.0-9.0 19H<br>δ0.5-4.5 21H |
| 87 | 82.54 | 6.97 | 0.00 | 10.49 | 82.51 | 6.92 | 0.00 | 10.57 | δ5.0-9.0 19H<br>δ0.5-4.5 33H |
| 88 | 81.11 | 7.32 | 0.00 | 11.57 | 81.13 | 7.29 | 0.00 | 11.58 | δ5.0-9.0 19H<br>δ0.5-4.5 41H |
| 89 | 81.24 | 7.54 | 0.00 | 11.22 | 81.27 | 7.53 | 0.00 | 11.20 | δ5.0-9.0 19H<br>δ0.5-4.5 45H |

Examples 90 to 148

Photochromic plastic lenses were manufactured and their characteristic properties were evaluated in the same manner as in Example 16 except that the compounds obtained in Examples 31 to 89 were used as chromene compounds. The results are shown in Table 7. In Table 7, compound Nos. 31 to 89 are chromene compounds obtained in Examples 31 to 89, respectively.

TABLE 7

| Example No. | Compound No. | $\lambda_{max}$ (nm) | Color optical density $A_0$ | Double peak characteristic $A_F/A_B$ | Fading half period $\tau_{1/2}$ (sec) | Initial coloration (absorption end) (nm) | Initial coloration (thermo-chromism) (%) | Residual rate $(A_{50}/A_0) \times 100$ | Color development sensitivity $\epsilon(10)/\epsilon(120)$ |
|---|---|---|---|---|---|---|---|---|---|
| 90 | 31 | 470<br>582 | 0.68<br>0.50 | 1.36 | 71<br>71 | 409 | 87<br>88 | 90<br>90 | 0.29 |
| 91 | 32 | 465<br>581 | 0.69<br>0.51 | 1.35 | 67<br>67 | 408 | 87<br>88 | 92<br>92 | 0.28 |
| 92 | 33 | 463<br>580 | 0.67<br>0.50 | 1.34 | 78<br>78 | 411 | 85<br>86 | 80<br>80 | 0.30 |
| 93 | 34 | 458<br>576 | 0.64<br>0.51 | 1.25 | 76<br>76 | 409 | 89<br>89 | 82<br>82 | 0.29 |
| 94 | 35 | 456<br>574 | 0.60<br>0.50 | 1.20 | 65<br>65 | 404 | 90<br>90 | 92<br>92 | 0.27 |
| 95 | 36 | 455<br>573 | 0.58<br>0.50 | 1.16 | 60<br>60 | 404 | 90<br>90 | 92<br>92 | 0.26 |
| 96 | 37 | 452<br>570 | 0.49<br>0.51 | 0.96 | 51<br>51 | 403 | 90<br>90 | 90<br>90 | 0.26 |
| 97 | 38 | 470<br>580 | 0.50<br>0.50 | 1.00 | 58<br>58 | 406 | 89<br>89 | 81<br>81 | 0.27 |
| 98 | 39 | 471<br>578 | 0.48<br>0.48 | 1.00 | 59<br>59 | 405 | 89<br>89 | 80<br>80 | 0.27 |
| 99 | 40 | 477<br>578 | 0.88<br>0.50 | 1.76 | 75<br>75 | 418 | 84<br>86 | 84<br>84 | 0.35 |
| 100 | 41 | 470<br>574 | 0.70<br>0.51 | 1.37 | 73<br>73 | 418 | 85<br>86 | 85<br>85 | 0.34 |
| 101 | 42 | 469<br>575 | 0.67<br>0.50 | 1.34 | 70<br>70 | 417 | 87<br>88 | 85<br>85 | 0.34 |
| 102 | 43 | 467<br>575 | 0.64<br>0.49 | 1.31 | 68<br>68 | 418 | 87<br>88 | 85<br>85 | 0.35 |
| 103 | 44 | 460<br>574 | 0.67<br>0.50 | 1.31 | 67<br>68 | 409 | 88<br>89 | 85<br>85 | 0.29 |
| 104 | 45 | 459<br>574 | 0.63<br>0.51 | 1.24 | 66<br>66 | 406 | 89<br>89 | 88<br>88 | 0.28 |
| 105 | 46 | 463<br>574 | 0.72<br>0.51 | 1.41 | 69<br>69 | 412 | 88<br>88 | 91<br>91 | 0.30 |

TABLE 7-continued

| Example No. | Compound No. | $\lambda_{max}$ (nm) | Color optical density $A_0$ | Double peak characteristic $A_Y/A_B$ | Fading half period $\tau^{1/2}$ (sec) | Initial coloration (absorption end) (nm) | Initial coloration (thermo-chromism) (%) | Residual rate $(A_{50}/A_0) \times 100$ | Color development sensitivity $\epsilon(10)/\epsilon(120)$ |
|---|---|---|---|---|---|---|---|---|---|
| 106 | 47 | 465 | 0.68 | 1.33 | 96 | 415 | 82 | 79 | 0.30 |
|  |  | 574 | 0.51 |  | 96 |  | 83 | 80 |  |
| 107 | 48 | 459 | 0.59 | 1.22 | 65 | 408 | 89 | 86 | 0.28 |
|  |  | 573 | 0.48 |  | 65 |  | 89 | 86 |  |
| 108 | 49 | 459 | 0.60 | 1.28 | 69 | 409 | 89 | 86 | 0.29 |
|  |  | 573 | 0.47 |  | 69 |  | 89 | 86 |  |
| 109 | 50 | 459 | 0.59 | 1.23 | 68 | 408 | 89 | 86 | 0.29 |
|  |  | 573 | 0.48 |  | 68 |  | 89 | 86 |  |
| 110 | 51 | 468 | 0.71 | 1.45 | 74 | 412 | 89 | 89 | 0.30 |
|  |  | 575 | 0.49 |  | 74 |  | 90 | 89 |  |
| 111 | 52 | 463 | 0.65 | 1.30 | 72 | 409 | 89 | 87 | 0.28 |
|  |  | 575 | 0.50 |  | 72 |  | 90 | 87 |  |
| 112 | 53 | 459 | 0.62 | 1.24 | 68 | 409 | 88 | 86 | 0.29 |
|  |  | 573 | 0.50 |  | 68 |  | 89 | 86 |  |
| 113 | 54 | 455 | 0.54 | 1.02 | 64 | 408 | 90 | 91 | 0.29 |
|  |  | 573 | 0.53 |  | 64 |  | 90 | 91 |  |
| 114 | 55 | 463 | 0.69 | 1.41 | 67 | 412 | 88 | 88 | 0.30 |
|  |  | 575 | 0.49 |  | 67 |  | 89 | 88 |  |
| 115 | 56 | 458 | 0.67 | 1.34 | 66 | 414 | 89 | 90 | 0.32 |
|  |  | 575 | 0.47 |  | 66 |  | 89 | 90 |  |
| 116 | 57 | 460 | 0.68 | 1.39 | 66 | 414 | 88 | 88 | 0.32 |
|  |  | 575 | 0.49 |  | 66 |  | 89 | 88 |  |
| 117 | 58 | 445 | 0.69 | 1.03 | 50 | 412 | 90 | 88 | 0.32 |
|  |  | 579 | 0.67 |  | 51 |  | 90 | 88 |  |
| 118 | 59 | 480 | 0.98 | 1.88 | 75 | 421 | 83 | 81 | 0.37 |
|  |  | 573 | 0.51 |  | 75 |  | 85 | 81 |  |
| 119 | 60 | 474 | 0.96 | 1.88 | 74 | 421 | 84 | 88 | 0.36 |
|  |  | 577 | 0.51 |  | 74 |  | 86 | 88 |  |
| 120 | 61 | 473 | 0.77 | 1.54 | 75 | 421 | 85 | 85 | 0.36 |
|  |  | 571 | 0.50 |  | 75 |  | 86 | 85 |  |
| 121 | 62 | 472 | 0.74 | 1.45 | 72 | 420 | 87 | 85 | 0.36 |
|  |  | 574 | 0.51 |  | 72 |  | 88 | 85 |  |
| 122 | 63 | 470 | 0.70 | 1.40 | 71 | 420 | 87 | 85 | 0.36 |
|  |  | 574 | 0.50 |  | 71 |  | 88 | 85 |  |
| 123 | 64 | 475 | 0.81 | 1.59 | 67 | 417 | 87 | 87 | 0.35 |
|  |  | 575 | 0.51 |  | 67 |  | 88 | 87 |  |
| 124 | 65 | 463 | 0.73 | 1.43 | 68 | 412 | 87 | 85 | 0.31 |
|  |  | 574 | 0.51 |  | 68 |  | 88 | 85 |  |
| 125 | 66 | 462 | 0.69 | 1.35 | 67 | 409 | 87 | 88 | 0.30 |
|  |  | 573 | 0.51 |  | 67 |  | 88 | 88 |  |
| 126 | 67 | 466 | 0.79 | 1.55 | 70 | 415 | 86 | 90 | 0.32 |
|  |  | 574 | 0.51 |  | 70 |  | 87 | 90 |  |
| 127 | 68 | 468 | 0.77 | 1.51 | 100 | 418 | 80 | 79 | 0.33 |
|  |  | 573 | 0.51 |  | 102 |  | 82 | 79 |  |
| 128 | 69 | 462 | 0.65 | 1.33 | 69 | 411 | 89 | 85 | 0.31 |
|  |  | 575 | 0.49 |  | 69 |  | 89 | 85 |  |
| 129 | 70 | 462 | 0.66 | 1.35 | 70 | 411 | 89 | 85 | 0.30 |
|  |  | 575 | 0.49 |  | 70 |  | 89 | 85 |  |
| 130 | 71 | 462 | 0.65 | 1.33 | 69 | 411 | 89 | 85 | 0.30 |
|  |  | 575 | 0.49 |  | 69 |  | 89 | 85 |  |
| 131 | 72 | 470 | 0.78 | 1.56 | 75 | 415 | 89 | 89 | 0.33 |
|  |  | 573 | 0.50 |  | 75 |  | 90 | 89 |  |
| 132 | 73 | 465 | 0.72 | 1.41 | 72 | 412 | 89 | 87 | 0.32 |
|  |  | 575 | 0.51 |  | 72 |  | 90 | 87 |  |
| 133 | 74 | 462 | 0.68 | 1.36 | 71 | 412 | 88 | 86 | 0.31 |
|  |  | 575 | 0.50 |  | 71 |  | 89 | 87 |  |
| 134 | 75 | 458 | 0.59 | 1.09 | 67 | 411 | 90 | 91 | 0.31 |
|  |  | 575 | 0.54 |  | 68 |  | 90 | 91 |  |
| 135 | 76 | 466 | 0.76 | 1.52 | 70 | 415 | 86 | 87 | 0.32 |
|  |  | 575 | 0.50 |  | 70 |  | 87 | 87 |  |
| 136 | 77 | 461 | 0.70 | 1.39 | 67 | 417 | 88 | 90 | 0.35 |
|  |  | 573 | 0.50 |  | 67 |  | 89 | 90 |  |
| 137 | 78 | 463 | 0.71 | 1.42 | 68 | 417 | 88 | 88 | 0.35 |
|  |  | 572 | 0.50 |  | 68 |  | 89 | 88 |  |
| 138 | 79 | 448 | 0.76 | 1.15 | 52 | 415 | 90 | 88 | 0.33 |
|  |  | 578 | 0.66 |  | 52 |  | 90 | 88 |  |
| 139 | 80 | 447 | 0.77 | 1.12 | 54 | 414 | 89 | 89 | 0.33 |
|  |  | 580 | 0.69 |  | 54 |  | 90 | 89 |  |
| 140 | 81 | 457 | 0.75 | 1.20 | 105 | 405 | 87 | 90 | 0.25 |
|  |  | 575 | 0.62 |  | 105 |  | 88 | 90 |  |
| 141 | 82 | 457 | 0.82 | 1.22 | 108 | 405 | 87 | 90 | 0.25 |
|  |  | 575 | 0.67 |  | 108 |  | 88 | 90 |  |
| 142 | 83 | 457 | 0.83 | 1.22 | 151 | 405 | 85 | 90 | 0.22 |
|  |  | 575 | 0.68 |  | 151 |  | 86 | 90 |  |

TABLE 7-continued

| Example No. | Compound No. | $\lambda_{max}$ (nm) | Color optical density $A_0$ | Double peak characteristic $A_Y/A_B$ | Fading half period $\tau^{1/2}$ (sec) | Initial coloration (absorption end) (nm) | Initial coloration (thermochromism) (%) | Residual rate $(A_{50}/A_0) \times 100$ | Color development sensitivity $\epsilon(10)/\epsilon(120)$ |
|---|---|---|---|---|---|---|---|---|---|
| 143 | 84 | 457 | 0.55 | 1.20 | 66 | 404 | 89 | 87 | 0.26 |
|  |  | 576 | 0.46 |  | 66 |  | 90 | 87 |  |
| 144 | 85 | 456 | 0.54 | 1.20 | 67 | 404 | 89 | 87 | 0.27 |
|  |  | 577 | 0.45 |  | 67 |  | 90 | 87 |  |
| 145 | 86 | 456 | 0.50 | 1.18 | 71 | 405 | 84 | 82 | 0.27 |
|  |  | 575 | 0.42 |  | 71 |  | 85 | 82 |  |
| 146 | 87 | 449 | 0.75 | 1.25 | 105 | 405 | 88 | 85 | 0.25 |
|  |  | 577 | 0.60 |  | 105 |  | 88 | 85 |  |
| 147 | 88 | 457 | 0.59 | 1.20 | 67 | 405 | 89 | 91 | 0.27 |
|  |  | 575 | 0.49 |  | 67 |  | 90 | 91 |  |
| 148 | 89 | 457 | 0.58 | 1.21 | 68 | 405 | 89 | 91 | 0.27 |
|  |  | 575 | 0.48 |  | 68 |  | 90 | 91 |  |

Examples of the naphthol compound are given below.

Example 149

90.0 g (381.8 mmol) of a benzene compound represented by the above formula (8) was dissolved in 450 ml of dichloromethane and cooled to 0° C. 148.8 g (1145.4 mmol) of oxalyl chloride and 4 ml of N,N-dimethylformamide were added dropwise to this solution. After the addition, the resulting mixture was heated to 25° C. and stirred for 2 hours. After the reaction, the solvent and an excess of oxalyl chloride were distilled off under reduced pressure. The obtained residue was dissolved in 450 ml of tetrahydrofuran and cooled to −50° C. 172 ml (343.6 mmol) of phenyl magnesium bromide (2.0 M diethyl ether solution) was added dropwise to this solution. After the addition, the resulting mixture was heated to 25° C. and stirred for 4 hours. After the reaction, 200 ml of toluene was added, the reaction product was washed in water, the solvent was removed, and the obtained product was purified by reslurrying with methanol to obtain a benzophenone derivative represented by the following formula (22) as 73.3 g (248.1 mmol, yield rate of 65%) of a white solid.

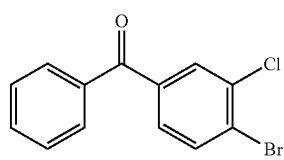

(22)

The benzophenone derivative of the above formula (22) and 67.7 g (372.1 mmol) of 2,4-dimethoxyphenylboronic acid were dissolved in 370 ml of 1,2-dimethoxyethane, and 37 ml of ethanol and 790 ml of a 10% sodium carbonate aqueous solution were added to this solution. The obtained solution was deaerated in a nitrogen gas stream, 0.287 g (0.248 mmol) of tetrakis(triphenylphosphine)palladium was added and refluxed for 3 hours. After the reaction, 400 ml of toluene was added, the reaction product was washed in water, the solvent was removed, and the obtained product was purified by reslurrying with methanol to obtain a compound represented by the following formula (23) as 91.9 g (243.1 mmol, yield rate of 98%) of a white solid.

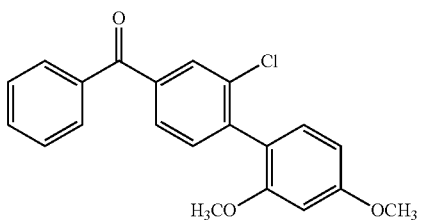

(23)

The compound of the above formula (23), 93.4 g (972.4 mmol) of sodium-t-butoxide, 5.5 g (24.3 mmol) of palladium acetate, 14.7 g (72.9 mmol) of tri-t-butyl phosphine and 63.6 g (729.3 mmol) of morpholine were dissolved in 920 ml of toluene and refluxed for 3 hours. After the reaction, the reaction product was washed in water, the solvent was removed, and the obtained product was purified by reslurrying with methanol to obtain a compound represented by the following formula (24) as 60.8 g (150.7 mmol, yield rate of 62%) of a white solid.

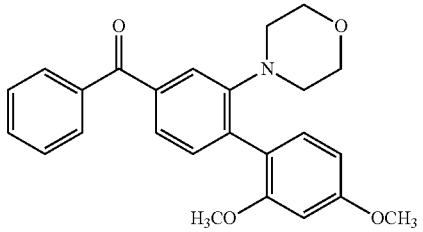

(24)

The compound of the above formula (24) and 30.2 g (173.3 mmol) of diethyl succinate were dissolved in 200 ml of tetrahydrofuran and heated to 55° C. A tetrahydrofuran solution (425 ml) of 19.4 g (173.3 mmol) of potassium-t-butoxide was added dropwise to this solution and stirred for 1 hour. After the reaction, 200 ml of toluene was added, the reaction product was washed with concentrated hydrochloride acid and then with water, and the solvent was removed to obtain a compound represented by the following formula (25) as 80.1 g (150.7 mmol, yield rate of 100%) of orange oil.

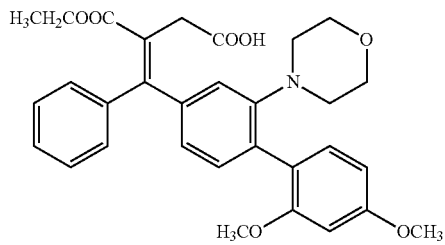

The compound of the above formula (25), 12.4 g (150.7 mmol) of sodium acetate and 76.9 g (75f0.4 mmol) of acetic anhydride were dissolved in 200 ml of toluene and refluxed for 3 hours. After the reaction, the reaction product was washed in water, the solvent was removed, and the obtained product was purified by recrystallization with ethyl acetate and acetonitrile to obtain a compound represented by the following formula (26) as 18.4 g (33.2 mmol, yield rate of 22%) of an orange solid.

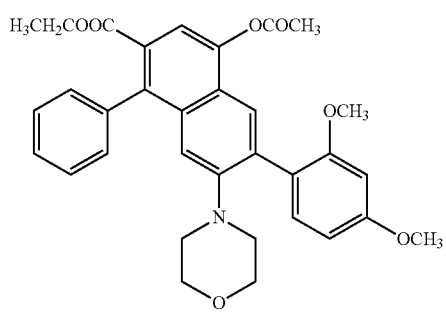

The compound of the above formula (26) was dispersed into 75 ml of methanol. 80 ml of an aqueous solution of 8.0 g (199.2 mmol) of sodium hydroxide was added to this solution and refluxed for 3 hours. After the reaction, the reaction product was washed with concentrated hydrochloric acid and then with water, the solvent was removed, and the obtained product was purified by reslurrying with toluene to obtain a carboxylic acid derivative represented by the following formula (27) as 15.1 g (31.2 mmol, yield rate of 94%) of a yellow solid.

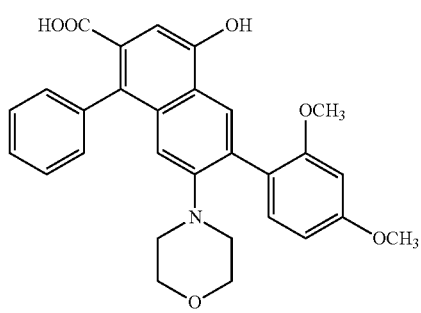

The carboxylic acid derivative of the above formula (27) and 8.7 g (68.6 mmol) of benzyl chloride were dissolved in 150 ml of N,N-dimethylformamide. 10.8 g (78.0 mmol) of potassium carbonate was added to this solution, heated to 60° C. and stirred for 3 hours. After the reaction, 200 ml of toluene was added, the reaction product was washed in water, and the solvent was removed to obtain a compound represented by the following formula (28) as 20.3 g (30.6 mmol, yield rate of 98%) of a yellow solid.

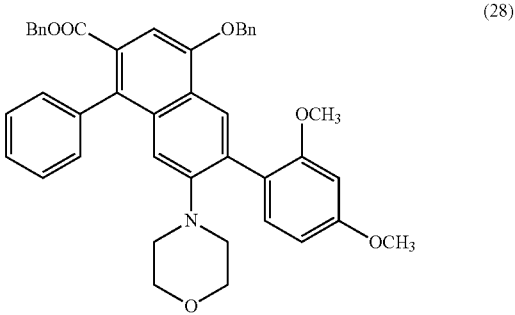

The compound of the above formula (28) was dispersed into 200 ml of isopropyl alcohol. 184 ml of an aqueous solution of 36.7 g (918.0 mmol) of sodium hydroxide was added to this solution and refluxed for 3 hours. After the reaction, 300 ml of ethyl acetate was added, the reaction product was washed with concentrated hydrochloric acid and then with water, the solvent was removed, and the obtained product was purified by reslurrying with toluene to obtain a carboxylic acid derivative represented by the following formula (29) as 17.2 g (30.0 mmol, yield rate of 98%) of a yellow solid.

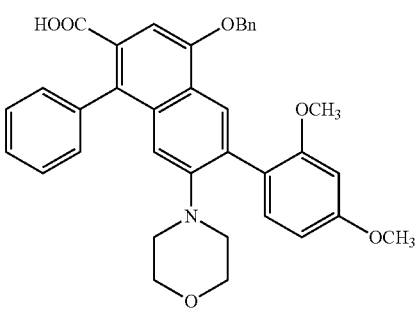

The compound of the above formula (29) was dispersed into 180 ml of toluene. 9.1 g (90.0 mmol) of triethylamine and 10.7 g (39.0 mmol) of diphenylphosphorylazide were added to this solution and stirred at room temperature for 2 hours. 6.9 g (150.0 mmol) of ethanol was added to this solution to carry out a reaction at 70° C. for 2 hours. 86 ml of ethanol was added to this solution, and then 16.8 g (300.0 mmol) of potassium hydroxide was added and refluxed for 3 hours. After the reaction, ethanol was distilled off at normal pressure, tetrahydrofuran was added, the reaction solution was washed in water, and the solvent was removed to obtain a compound represented by the following formula (30) as 14.4 g (26.4 mmol, yield rate of 88%) of a yellow solid.

(30)

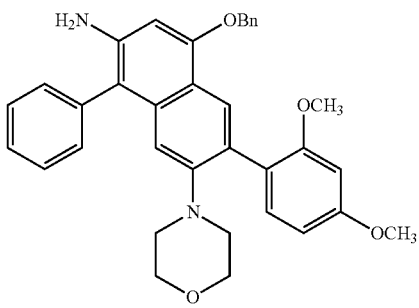

The compound of the above formula (30) was dispersed into 150 ml of acetonitrile, and 113.3 g (130.7 mmol) of a 6% hydrochloric acid aqueous solution was added and cooled to 0 to 5° C. 8.2 g (39.6 mmol) of a 33% sodium nitrite aqueous solution was added to this solution and stirred for 30 minutes. 21.9 g (132.0 mmol) of a 50% potassium iodide aqueous solution was added to this solution and stirred at room temperature for 6 hours. After the reaction, toluene was added, the reaction product was washed in water, the solvent was removed, and the obtained product was purified by column chromatography to obtain a compound represented by the following formula (31) as 12.5 g (19.0 mmol, yield rate of 72%) of a yellow solid.

(31)

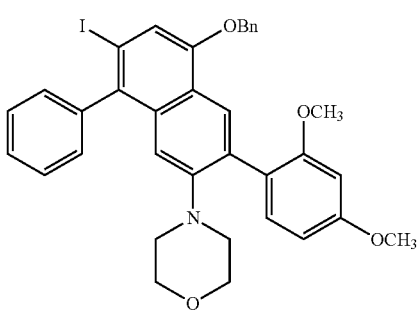

The compound of the above formula (31) was dispersed into 375 ml of toluene and cooled to −50° C. 13.1 ml (20.9 mmol) of n-butyl lithium (1.6 M hexane solution) was added dropwise to this solution and stirred for 30 minutes. 7.3 g of a toluene solution of 3.7 g (23.8 mmol) of 3,3,5,5-tetramethylcyclohexanone was added dropwise to this solution and stirred at 0° C. for 3 hours. After the reaction, toluene was added, the reaction product was washed in water, the solvent was removed, and the obtained product was purified by reslurrying with methanol to obtain a compound represented by the following formula (32) as 7.5 g (11.0 mmol, yield rate of 58%) of a yellow solid.

(32)

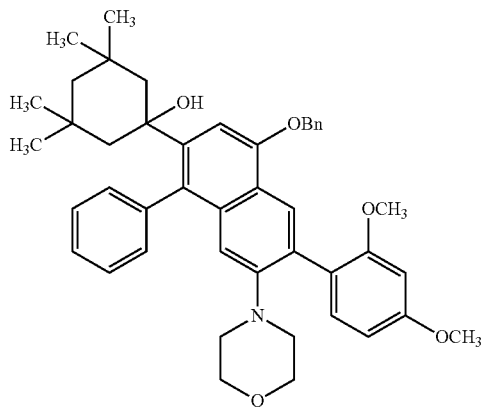

The compound of the above formula (32) was dissolved in 150 ml of tetrahydrofuran, and 2.8 g (44.0 mmol) of ammonium formate and 2.3 g of 5% palladium carbide were added and stirred at room temperature for 8 hours. After the reaction, 50 ml of toluene was added, the reaction product was washed in water, the solvent was distilled off, and the obtained product was purified by reslurrying with toluene to obtain a compound represented by the following formula (33) as 6.0 g (10.1 mmol, yield rate of 92%) of a yellow solid.

(33)

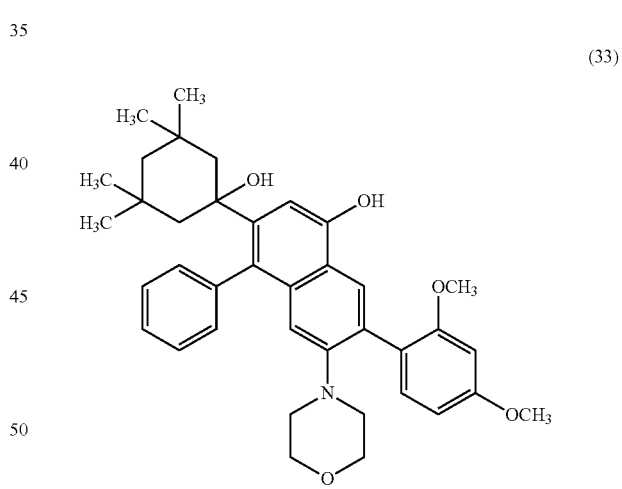

The compound of the above formula (33) was dissolved in 120 ml of toluene and heated to 90° C. 57.6 g (303.0 mmol) of p-toluenesulfonic acid monohydrate was added to this solution and refluxed for 4 hours. After the reaction, the reaction product was washed in water, the solvent was removed, and the obtained product was purified by column chromatography to obtain a naphthol compound represented by the following formula (34) as 4.4 g (7.6 mmol, yield rate of 75%) of a white solid.

(34)

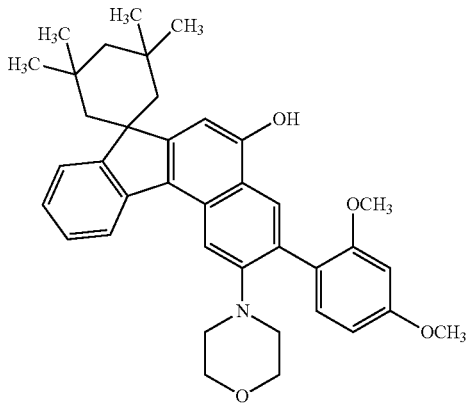

The elemental analysis values of this product were 78.96% of C, 7.54% of H, 2.38% of N and 11.12% of O which were almost equal to the calculated values of $C_{38}H_{43}NO_4$ (C: 79.00%, H: 7.50%, N: 2.42%, O: 11.08%).

When the proton nuclear magnetic resonance spectrum of the product was measured, it showed a 32H peak based on an alkyl group at δ of around 0.5 to 4.5 ppm and 11H peaks based on a hydroxyl group and an aromatic proton at δ of around 5.0 to 9.0 ppm Further, when the $^{13}C$-nuclear magnetic resonance spectrum was measured, it showed a peak based on the carbon of an aromatic ring at δ of around 110 to 160 ppm and a peak based on the carbon of an alkyl group at δ of around 20 to 80 ppm.

It was confirmed from these results that the isolated product was a compound represented by the above formula (34).

This compound is a naphthol compound used in the above Example 3.

Examples 150 to 219

Naphthol compounds shown in the tables below were synthesized in the same manner as in Example 149. When the structures of the obtained products were analyzed by using the same structure confirming means as in Example 149, it was confirmed that they were naphthol compounds used in Examples shown in Table 7. Table 8 shows the elemental analysis values, calculated values obtained from the structural formulas of the compounds and characteristic $^1$H-NMR spectra of these compounds.

TABLE 8

| Example No. | Example No. of chromene compounds* | Elemental analysis values | | | | | | | | $^1$H-NMR (NMR) |
|---|---|---|---|---|---|---|---|---|---|---|
| | | Experimental values | | | | Calculated values | | | | |
| | | C | H | N | O | C | H | N | O | |
| 150 | 1 | 80.34 | 7.51 | 0.00 | 12.15 | 80.43 | 7.33 | 0.00 | 12.24 | δ5.0-9.0 16H δ0.5-4.5 24H |
| 151 | 2 | 82.09 | 6.87 | 0.00 | 11.04 | 82.16 | 6.89 | 0.00 | 10.94 | δ5.0-9.0 16H δ0.5-4.5 24H |
| 152 | 4 | 80.77 | 7.86 | 2.79 | 8.78 | 80.71 | 7.71 | 2.61 | 8.96 | δ5.0-9.0 11H δ0.5-4.5 30H |
| 153 | 5 | 83.01 | 7.54 | 0.00 | 9.45 | 82.97 | 7.56 | 0.00 | 9.47 | δ5.0-9.0 11H δ0.5-4.5 25H |
| 154 | 6 | 85.57 | 7.36 | 0.00 | 7.07 | 85.68 | 7.41 | 0.00 | 6.92 | δ5.0-9.0 13H δ0.5-4.5 21H |
| 155 | 7 | 86.64 | 7.16 | 0.00 | 6.20 | 86.68 | 7.08 | 0.00 | 6.24 | δ5.0-9.0 15H δ0.5-4.5 21H |
| 156 | 8 | 86.87 | 7.05 | 0.00 | 6.08 | 86.95 | 7.11 | 0.00 | 5.94 | δ5.0-9.0 17H δ0.5-4.5 21H |
| 157 | 9 | 81.07 | 7.53 | 2.49 | 8.91 | 81.13 | 7.54 | 2.56 | 8.76 | δ5.0-9.0 11H δ0.5-4.5 30H |
| 158 | 10 | 78.77 | 6.16 | 0.00 | 15.07 | 78.85 | 6.14 | 0.00 | 15.01 | δ5.0-9.0 11H δ0.5-4.5 15H |
| 159 | 11 | 75.87 | 5.69 | 0.00 | 18.44 | 75.68 | 5.65 | 0.00 | 18.67 | δ5.0-9.0 11H δ0.5-4.5 13H |
| 160 | 12 | 83.14 | 6.38 | 0.00 | 10.48 | 83.01 | 6.29 | 0.00 | 10.70 | δ5.0-9.0 12H δ0.5-4.5 17H |
| 161 | 13 | 73.98 | 5.49 | 0.00 | — | 73.83 | 5.42 | 0.00 | 6.15 | δ5.0-9.0 11H δ0.5-4.5 17H |
| 162 | 14 | 74.77 | 5.68 | 3.05 | 16.50 | 74.83 | 5.65 | 2.91 | 16.61 | δ5.0-9.0 8H δ0.5-4.5 19H |
| 163 | 15 | 82.24 | 7.22 | 0.00 | 10.54 | 82.27 | 7.13 | 0.00 | 10.61 | δ5.0-9.0 11H δ0.5-4.5 21H |
| 164 | 31 | 83.44 | 8.79 | 2.39 | 5.38 | 83.49 | 8.71 | 2.37 | 5.42 | δ5.0-9.0 12H δ0.5-4.5 39H |
| 165 | 32 | 83.28 | 7.82 | 2.68 | 6.22 | 83.13 | 7.77 | 2.77 | 6.33 | δ5.0-9.0 12H δ0.5-4.5 27H |
| 166 | 33 | 82.74 | 7.41 | 2.99 | 6.86 | 82.98 | 7.39 | 2.93 | 6.70 | δ5.0-9.0 12H δ0.5-4.5 23H |
| 167 | 34 | 82.66 | 7.29 | 0.00 | 10.05 | 82.81 | 7.16 | 0.00 | 10.03 | δ5.0-9.0 12H δ0.5-4.5 22H |
| 168 | 35 | 82.79 | 7.46 | 0.00 | 9.75 | 82.89 | 7.37 | 0.00 | 9.74 | δ5.0-9.0 12H δ0.5-4.5 24H |
| 169 | 36 | 85.61 | 7.79 | 0.00 | 6.60 | 85.67 | 7.61 | 0.00 | 6.71 | δ5.0-9.0 12H δ0.5-4.5 24H |
| 170 | 37 | 82.39 | 7.04 | 0.00 | — | 82.47 | 6.92 | 0.00 | 6.66 | δ5.0-9.0 12H δ0.5-4.5 21H |

TABLE 8-continued

| Example No. | Example No. of chromene compounds* | Elemental analysis values | | | | | | | | ¹H-NMR (NMR) |
|---|---|---|---|---|---|---|---|---|---|---|
| | | Experimental values | | | | Calculated values | | | | |
| | | C | H | N | O | C | H | N | O | |
| 171 | 38 | 82.59 | 7.38 | 3.21 | 6.92 | 82.45 | 7.37 | 3.10 | 7.09 | δ5.0-9.0 11H δ0.5-4.5 22H |
| 172 | 39 | 79.51 | 6.69 | 0.00 | — | 79.45 | 6.88 | 0.00 | 6.83 | δ5.0-9.0 11H δ0.5-4.5 21H |
| 173 | 40 | 81.39 | 7.90 | 2.46 | 8.25 | 81.35 | 7.88 | 2.43 | 8.34 | δ5.0-9.0 11H δ0.5-4.5 34H |
| 174 | 41 | 81.45 | 8.11 | 2.45 | 7.99 | 81.46 | 8.03 | 2.37 | 8.14 | δ5.0-9.0 11H δ0.5-4.5 36H |
| 175 | 42 | 81.42 | 7.95 | 2.36 | 8.27 | 81.35 | 7.88 | 2.43 | 8.34 | δ5.0-9.0 11H δ0.5-4.5 34H |
| 176 | 43 | 82.64 | 7.09 | 2.21 | 8.06 | 82.72 | 7.11 | 2.30 | 7.87 | δ5.0-9.0 15H δ0.5-4.5 28H |
| 177 | 44 | 75.01 | 6.54 | 2.46 | — | 75.12 | 6.49 | 2.58 | 8.83 | δ5.0-9.0 11H δ0.5-4.5 24H |
| 178 | 45 | 67.20 | 5.51 | 2.34 | — | 67.18 | 5.48 | 2.18 | 7.46 | δ5.0-9.0 11H δ0.5-4.5 24H |
| 179 | 46 | 67.99 | 5.89 | 2.04 | — | 67.95 | 5.85 | 2.09 | 7.15 | δ5.0-9.0 11H δ0.5-4.5 28H |
| 180 | 47 | 80.14 | 7.09 | 0.00 | 12.77 | 80.28 | 7.13 | 0.00 | 12.58 | δ5.0-9.0 12H δ0.5-4.5 24H |
| 181 | 48 | 81.26 | 7.99 | 0.00 | 10.75 | 81.32 | 7.85 | 0.00 | 10.83 | δ5.0-9.0 11H δ0.5-4.5 35H |
| 182 | 49 | 81.16 | 7.87 | 0.00 | 10.97 | 81.21 | 7.69 | 0.00 | 11.10 | δ5.0-9.0 11H δ0.5-4.5 33H |
| 183 | 50 | 80.98 | 7.44 | 0.00 | 11.58 | 81.10 | 7.52 | 0.00 | 11.37 | δ5.0-9.0 11H δ0.5-4.5 31H |
| 184 | 51 | 82.35 | 7.81 | 0.00 | 9.84 | 82.21 | 7.84 | 0.00 | 9.96 | δ5.0-9.0 11H δ0.5-4.5 39H |
| 185 | 52 | 82.16 | 7.97 | 0.00 | 9.87 | 82.21 | 7.84 | 0.00 | 9.96 | δ5.0-9.0 11H δ0.5-4.5 39H |
| 186 | 53 | 81.55 | 7.81 | 0.00 | 10.64 | 81.69 | 7.69 | 0.00 | 10.62 | δ5.0-9.0 11H δ0.5-4.5 35H |
| 187 | 54 | 78.26 | 7.40 | 0.00 | 14.34 | 78.23 | 7.29 | 0.00 | 14.47 | δ5.0-9.0 11H δ0.5-4.5 35H |
| 188 | 55 | 78.45 | 7.71 | 2.54 | 11.30 | 78.55 | 7.66 | 2.48 | 11.31 | δ5.0-9.0 11H δ0.5-4.5 32H |
| 189 | 56 | 79.94 | 6.94 | 0.00 | 13.12 | 80.10 | 6.89 | 0.00 | 13.01 | δ5.0-9.0 15H δ0.5-4.5 27H |
| 190 | 57 | 78.78 | 7.10 | 2.25 | 11.87 | 78.89 | 7.07 | 2.09 | 11.94 | δ5.0-9.0 15H δ0.5-4.5 32H |
| 191 | 58 | 83.45 | 8.14 | 0.00 | 8.41 | 83.58 | 8.07 | 0.00 | 8.35 | δ5.0-9.0 11H δ0.5-4.5 35H |
| 192 | 59 | 81.24 | 7.99 | 5.13 | 5.64 | 81.39 | 7.91 | 5.00 | 5.71 | δ5.0-9.0 12H δ0.5-4.5 32H |
| 193 | 60 | 81.84 | 8.12 | 4.75 | 5.29 | 81.96 | 8.05 | 4.66 | 5.33 | δ5.0-9.0 12H δ0.5-4.5 36H |
| 194 | 61 | 81.96 | 8.31 | 4.67 | 5.06 | 82.04 | 8.20 | 4.56 | 5.20 | δ5.0-9.0 12H δ0.5-4.5 38H |
| 195 | 62 | 82.03 | 7.97 | 4.54 | 5.46 | 81.96 | 8.05 | 4.66 | 5.33 | δ5.0-9.0 12H δ0.5-4.5 36H |
| 196 | 63 | 83.21 | 7.42 | 4.37 | 5.00 | 83.24 | 7.30 | 4.41 | 5.04 | δ5.0-9.0 16H δ0.5-4.5 30H |
| 197 | 64 | 79.82 | 7.65 | 4.71 | 7.82 | 79.70 | 7.69 | 4.65 | 7.96 | δ5.0-9.0 12H δ0.5-4.5 34H |
| 198 | 65 | 76.06 | 6.81 | 5.01 | — | 76.03 | 6.74 | 4.93 | 5.63 | δ5.0-9.0 12H δ0.5-4.5 26H |
| 199 | 66 | 68.31 | 5.82 | 4.31 | — | 68.25 | 5.73 | 4.19 | 4.79 | δ5.0-9.0 12H δ0.5-4.5 26H |
| 200 | 67 | 68.85 | 6.15 | 4.04 | — | 68.95 | 6.08 | 4.02 | .59 | δ5.0-9.0 12H δ0.5-4.5 30H |
| 201 | 68 | 80.99 | 7.42 | 2.71 | 8.88 | 81.02 | 7.37 | 2.62 | 8.99 | δ5.0-9.0 13H δ0.5-4.5 26H |
| 202 | 69 | 81.78 | 8.10 | 2.19 | 7.93 | 81.91 | 8.02 | 2.27 | 7.79 | δ5.0-9.0 12H δ0.5-4.5 37H |

TABLE 8-continued

| Example No. | Example No. of chromene compounds* | Elemental analysis values | | | | | | | | ¹H-NMR (NMR) |
|---|---|---|---|---|---|---|---|---|---|---|
| | | Experimental values | | | | Calculated values | | | | |
| | | C | H | N | O | C | H | N | O | |
| 203 | 70 | 81.93 | 7.91 | 2.46 | 7.70 | 81.83 | 7.87 | 2.33 | 7.98 | δ5.0-9.0 12H δ0.5-4.5 35H |
| 204 | 71 | 81.87 | 7.90 | 2.41 | 7.82 | 81.73 | 7.72 | 2.38 | 8.17 | δ5.0-9.0 12H δ0.5-4.5 33H |
| 205 | 72 | 82.69 | 7.95 | 1.99 | 7.37 | 82.72 | 8.00 | 2.10 | 7.19 | δ5.0-9.0 12H δ0.5-4.5 41H |
| 206 | 73 | 82.79 | 8.05 | 2.07 | 7.09 | 82.72 | 8.00 | 2.10 | 7.19 | δ5.0-9.0 12H δ0.5-4.5 41H |
| 207 | 74 | 82.39 | 7.91 | 2.34 | 7.36 | 82.26 | 7.87 | 2.23 | 7.64 | δ5.0-9.0 12H δ0.5-4.5 37H |
| 208 | 75 | 79.10 | 7.46 | 2.51 | 10.93 | 79.00 | 7.50 | 2.42 | 11.08 | δ5.0-9.0 12H δ0.5-4.5 31H |
| 209 | 76 | 79.34 | 7.89 | 4.86 | 7.91 | 79.29 | 7.85 | 4.74 | 8.12 | δ5.0-9.0 12H δ0.5-4.5 34H |
| 210 | 77 | 80.64 | 7.14 | 2.24 | 9.98 | 80.72 | 7.09 | 2.19 | 10.00 | δ5.0-9.0 16H δ0.5-4.5 29H |
| 211 | 78 | 79.54 | 7.29 | 3.97 | 9.20 | 79.51 | 7.25 | 4.03 | 9.21 | δ5.0-9.0 16H δ0.5-4.5 34H |
| 212 | 79 | 84.21 | 8.16 | 2.46 | 5.17 | 84.10 | 8.23 | 2.34 | 5.33 | δ5.0-9.0 12H δ0.5-4.5 37H |
| 213 | 80 | 83.56 | 7.85 | 2.75 | 5.84 | 83.58 | 7.77 | 2.63 | 6.02 | δ5.0-9.0 12H δ0.5-4.5 29H |
| 214 | 81 | 80.21 | 7.25 | 0.00 | 12.54 | 80.28 | 7.13 | 0.00 | 12.58 | δ5.0-9.0 11H δ0.5-4.5 25H |
| 215 | 82 | 80.04 | 6.91 | 0.00 | 13.05 | 80.13 | 6.93 | 0.00 | 12.94 | δ5.0-9.0 11H δ0.5-4.5 23H |
| 216 | 83 | 79.68 | 6.64 | 0.00 | 13.68 | 79.80 | 6.48 | 0.00 | 13.72 | δ5.0-9.0 11H δ0.5-4.5 19H |
| 217 | 84 | 80.25 | 7.21 | 0.00 | 12.54 | 80.28 | 7.13 | 0.00 | 12.58 | δ5.0-9.0 11H δ0.5-4.5 25H |
| 218 | 85 | 80.26 | 7.16 | 0.00 | 12.58 | 80.28 | 7.13 | 0.00 | 12.58 | δ5.0-9.0 11H δ0.5-4.5 25H |
| 219 | 86 | 76.14 | 5.79 | 0.00 | 18.07 | 76.00 | 5.92 | 0.00 | 18.08 | δ5.0-9.0 11H δ0.5-4.5 15H |

*Examples of chromene compounds produced by using the naphthol compounds of Examples.

Examples 220 to 222

Photochromic plastic lenses were manufactured and their characteristic properties were evaluated in the same manner as in Example 18 except that the chromene compound (chromene compound No. 1) of Example 1 of the present invention was mixed with each of the following chromene compounds (35), (36) and (37) in a ratio shown in Table 9. The results are shown in Table 11.

TABLE 9

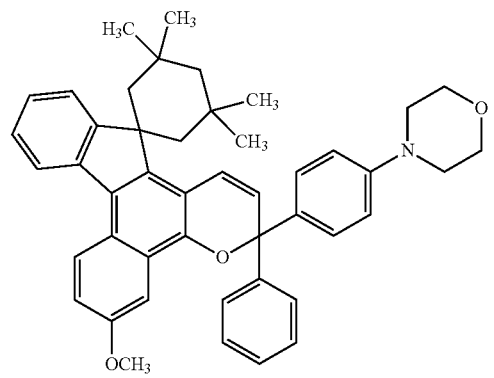 [SMILES: COc1ccc2c3c(c4c(c2c1)OC(c1ccccc1)(c1ccc(N2CCOCC2)cc1)C=C4)C1(CC(C)(C)CC(C)(C)C1)c1ccccc1-3]

(35)

TABLE 9-continued

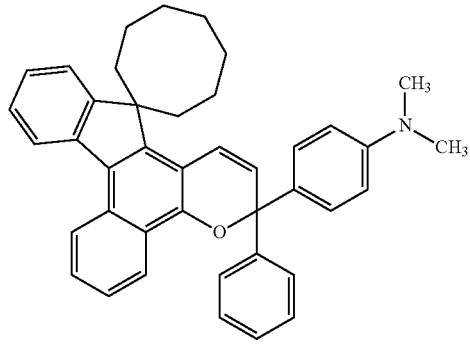 [SMILES: CN(C)c1ccc(C2(c3ccccc3)C=Cc3c4c(c5ccccc5c3O2)-c2ccccc2C42CCCCCCC2)cc1]

(36)

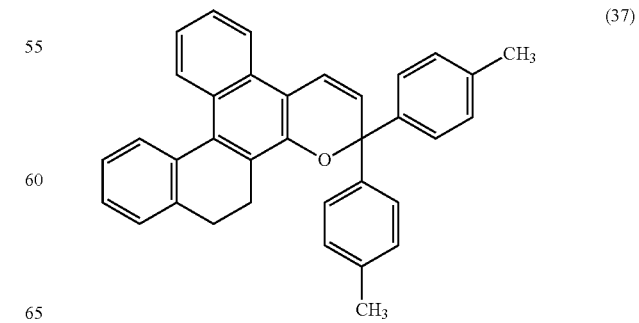

(37)

TABLE 9-continued

| Example No. | Photochromic compound | | | | |
|---|---|---|---|---|---|
| | Compound No. | 1 | 54 | 55 | 56 | Color |
| 220 | Amount | 2.0 | 0.2 | — | — | gray |
| 221 | (parts by | 2.5 | — | 0.4 | — | gray |
| 222 | mass) | 2.0 | — | 0.1 | 0.2 | brown |

TABLE 10

| Example No. | $\lambda_{max}$ (nm) | Color optical density $A_0$ | Double peak characteristic $A_Y/A_B$ | Fading half period $\tau\frac{1}{2}$ (sec) | Initial coloration (absorption end) (nm) | Initial coloration (thermochromism) (%) | Residual rate $(A_{50}/A_0) \times 100$ | Color development sensitivity $\epsilon(10)/\epsilon(120)$ |
|---|---|---|---|---|---|---|---|---|
| 220 | 463 | 1.01 | 1.03 | 66 | 411 | 89 | 90 | 0.29 |
| | 576 | 0.98 | | 66 | | 89 | 91 | |
| 221 | 457 | 1.09 | 1.00 | 68 | 410 | 89 | 90 | 0.28 |
| | 578 | 1.09 | | 68 | | 89 | 89 | |
| 222 | 456 | 1.08 | 1.54 | 68 | 408 | 88 | 89 | 0.28 |
| | 578 | 0.70 | | 68 | | 89 | 89 | |

As shown in Table 10, the photochromic plastic lenses which were obtained by curing the chromene compositions of the present invention had a transmittance by thermochromism of not less than 88%. Further, as its absorption end is existent at 405 to 415 nm, they had little initial coloration and high color development sensitivity.

EFFECT OF THE INVENTION

The chromene compound of the present invention develops a color of a neutral tint and has little initial coloration, high color development sensitivity, high color optical density and a high fading speed even when it is dispersed into a solution or a polymer solid matrix as well as excellent durability.

Therefore, a photochromic lens manufactured by using the chromene compound of the present invention exhibits such excellent photochromic properties that it develops a dark color of a neutral tint swiftly when it moves outside and returns to its original color swiftly when it returns inside from outside and has high durability that it can be used for a long time.

The invention claimed is:

1. A chromene compound having a skeleton represented by the following formula (2):

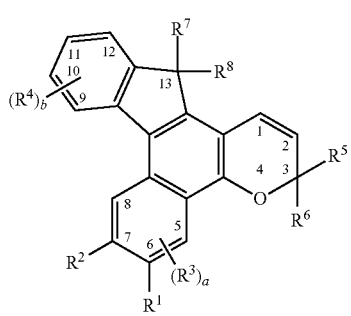

(2)

wherein $R^1$ is an aryl group or a heteroaryl group, and $R^2$ is an electron donor group having a Hammett constant $\sigma_p$ of not more than −0.1, $R^3$ and $R^4$ are each independently a hydroxyl group, alkyl group, haloalkyl group, cycloalkyl group, alkoxy group, amino group, heterocyclic group having a ring member nitrogen atom and bonded to a benzene ring bonded thereto via the nitrogen atom, cyano group, nitro group, formyl group, hydroxycarbonyl group, alkylcarbonyl group, alkoxycarbonyl group, halogen atom, aralkyl group, aralkoxy group, aryl group or aryloxy group, $R^5$ and $R^6$ are each independently an aryl group, heteroaryl group, alkyl group, or a group represented by the following formula (3):

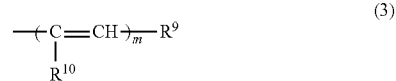

(3)

wherein $R^9$ is an aryl group or heteroaryl group, $R^{10}$ is a hydrogen atom, alkyl group or halogen atom, and m is an integer of 1 to 3, group represented by the following formula (4):

(4)

wherein $R^{11}$ is an aryl group or heteroaryl group, and n is an integer of 1 to 3, $R^5$ and $R^6$ may be bonded together to form an aliphatic hydrocarbon ring together with the carbon atom bonded thereto, $R^7$ and $R^8$ are each independently a hydrogen atom, hydroxyl group, alkyl group, haloalkyl group, cycloalkyl group, alkoxy group, amino group, heterocyclic group having a ring member nitrogen atom and bonded to the 13-position carbon atom via the nitrogen atom, cyano group, nitro group, formyl group, hydroxycarbonyl group, alkylcarbonyl group, alkoxycarbonyl group, halogen atom, aralkyl group, aralkoxy group, aryl group or aryloxy group, $R^7$ and $R^8$ may be bonded together to form an aliphatic ring having 3 to 20 ring member carbon atoms, condensed polycyclic ring having an aromatic ring or an aromatic hetero ring condensed to the aliphatic ring, hetero ring having 3 to 20 ring member atoms, or condensed polycyclic ring having an aromatic ring or an aromatic hetero ring condensed to the hetero ring, together with the 13-position carbon atom bonded thereto, "a" is an integer of 0 to 2, and b is an integer of 0 to 4, with the proviso that when "a" is 2, two $R^3$'s may be the same or different and when b is 2 to 4, a plurality of $R^4$'s may be the same or different.

2. The chromene compound according to claim 1, wherein $R^1$ is an aryl group having 6 to 14 carbon atom, a heteroaryl group having 4 to 12 carbon atoms, or an aryl group having 6 to 14 carbon atoms or a heteroaryl group having 4 to 12 carbon atoms substituted by at least one substituent selected from the group consisting of hydroxyl group, alkyl group, haloalkyl group, cycloalkyl group, alkoxy group, amino group, heterocyclic group having a ring member nitrogen atom and bonded to a benzene ring bonded thereto via the nitrogen atom, cyano group, nitro group, formyl group, hydroxycarbonyl group, alkylcarbonyl group, alkoxycarbonyl group, halogen atom, aralkyl group, aryl group and aryloxy group.

3. A photochromic curable composition comprising the chromene compound of claim 2 and a polymerizable monomer.

4. A photochromic optical article having a polymer molded product containing the chromene compound of claim 2 dispersed in the polymer molded product as a constituent member.

5. The chromene compound according to claim 1, wherein $R^2$ is a hydroxyl group, alkyl group, cycloalkyl group, alkoxy group, aryloxy group, amino group or heterocyclic group having a ring member nitrogen atom and bonded to the 7-position carbon atom via the nitrogen atom.

6. A photochromic curable composition comprising the chromene compound of claim 5 and a polymerizable monomer.

7. A photochromic optical article having a polymer molded product containing the chromene compound of claim 5 dispersed in the polymer molded product as a constituent member.

8. The chromene compound according to claim 1, wherein $R^7$ and $R^8$ are bonded together to form an aliphatic hydrocarbon ring together with the 13-position carbon atom, and the aliphatic hydrocarbon ring has 3 to 20 ring member carbon atoms and may have at least one substituent selected from the group consisting of alky group, haloalkyl group, cycloalkyl group, alkoxy group, amino group, aralkyl group, aryl group and halogen atom.

9. The chromene compound according to claim 8, wherein the aliphatic hydrocarbon ring is a cyclohexane ring substituted by an alkyl group having 1 to 4 carbon atoms.

10. A photochromic curable composition comprising the chromene compound of claim 9 and a polymerizable monomer.

11. A photochromic optical article having a polymer molded product containing the chromene compound of claim 9 dispersed in the polymer molded product as a constituent member.

12. A photochromic curable composition comprising the chromene compound of claim 8 and a polymerizable monomer.

13. A photochromic optical article having a polymer molded product containing the chromene compound of claim 8 dispersed in the polymer molded product as a constituent member.

14. An optical article having an optical substrate all or part of at least one surface of which is coated with a polymer film containing the chromene compound of claim 1 dispersed in the polymer film as a constituent member.

15. A photochromic curable composition comprising the chromene compound of claim 1 and a polymerizable monomer.

16. A photochromic optical article having a polymer molded product containing the chromene compound of claim 1 dispersed in the polymer molded product as a constituent member.

* * * * *